(12) United States Patent
Yukawa et al.

(10) Patent No.: US 12,188,025 B2
(45) Date of Patent: Jan. 7, 2025

(54) GENUS HYDROGENOPHILUS BACTERIUM TRANSFORMANT

(71) Applicants: Utilization of Carbon Dioxide Institute Co., Ltd., Tokyo (JP); The University of Tokyo, Tokyo (JP)

(72) Inventors: Hideaki Yukawa, Tokyo (JP); Naoto Ohtani, Tokyo (JP); Masaharu Ishii, Tokyo (JP)

(73) Assignees: Utilization of Carbon Dioxide Institute Co., Ltd., Tokyo (JP); The University of Tokyo, Tokyo (JP)

(*) Notice: Subject to any disclaimer, the term of this patent is extended or adjusted under 35 U.S.C. 154(b) by 0 days.

(21) Appl. No.: 18/316,224

(22) Filed: May 11, 2023

(65) Prior Publication Data

US 2023/0340504 A1  Oct. 26, 2023

Related U.S. Application Data

(62) Division of application No. 17/047,757, filed as application No. PCT/JP2018/024073 on Jun. 25, 2018, now Pat. No. 11,697,817.

(30) Foreign Application Priority Data

Apr. 27, 2018  (JP) .................. 2018-086100

(51) Int. Cl.
| C12N 9/06 | (2006.01) |
| C12N 15/74 | (2006.01) |
| C12P 7/06 | (2006.01) |
| C12P 7/16 | (2006.01) |
| C12P 13/06 | (2006.01) |

(52) U.S. Cl.
CPC ............. *C12N 15/74* (2013.01); *C12P 7/06* (2013.01); *C12P 7/16* (2013.01); *C12Y 101/01001* (2013.01); *C12Y 401/01001* (2013.01)

(58) Field of Classification Search
CPC ..... C12N 15/11; C12N 15/111; C12N 15/113; C12N 15/74; C12N 9/0012
See application file for complete search history.

(56) References Cited

U.S. PATENT DOCUMENTS

| 5,559,016 | A | 9/1996 | Katsumata et al. |
| 2004/0072312 | A1 | 4/2004 | Yukawa |
| 2011/0097775 | A1 | 4/2011 | Green et al. |
| 2011/0287499 | A1 | 11/2011 | Brown et al. |
| 2012/0115196 | A1 | 5/2012 | Yukawa et al. |
| 2014/0256904 | A1* | 9/2014 | Schaffer ............... C08G 69/08 435/129 |
| 2014/0273128 | A1 | 9/2014 | Coleman et al. |

FOREIGN PATENT DOCUMENTS

| JP | H06-277082 A | 10/1994 |
| WO | 01/96573 A1 | 12/2001 |
| WO | 2009/122192 A1 | 10/2009 |
| WO | 2010/113832 A1 | 10/2010 |

OTHER PUBLICATIONS

Lucas et al., UniProt database, accession No. A0A0E0TGY0, May 2015.*
Atsumi et al., "Non-fermentative pathways for synthesis of branched-chain higher alcohols as biofuels," Nature, 451: 86-89 (2008).
Atsumi et al., "Engineering the isobutanol biosynthetic pathway in *Escherichia coli* by comparison of three aldehyde reductase/alcohol dehydrogenase genes," Applied and Environmental Microbiology, 85: 651-657 (2010).
Li et al., "Engineering Bacillus subtilis for isobutanol production by heterologous Ehrlich pathway construction and the biosynthetic 2-ketoisovalerate precursor pathway overexpression," Applied and Environmental Microbiology, 91: 577-589 (2011).
Jeon et al., "Isobutanol production from an engineered Shewanella oneidensis MR-1," Bioprocess Biosyst. Eng., 38: 2147-2154 (2015).
Atsumi et al., "Direct photosynthetic recycling of carbon dioxide to isobutyraldehyde," Nature Biotechnology, 27 (12): 1177-1180 (2009).
Lu et al., "Studies on the production of branched-chain alcohols in engineered Ralstonia eutropha," Applied Microbiology and Biotechnology, 96: 283-297 (2012).
Lin et al., "Isobutanol production at elevated temperatures in thermophilic Geobacillus thermoglucosidasius," Metabolic Engineering, 24:1-8 (2014).
Liu et al., "Coexpression of pyruvate decarboxylase and alcohol dehydrogenase genes in Lactobacillus brevis, " FEMS Microbiol. Lett. 274: 291-297 (2007).
Talarico et al., "Construction and expression of an ethanol production operon in Gram-positive bacteria," Microbiology, 151: 4023-4031 (2005).

(Continued)

*Primary Examiner* — Maryam Monshipouri
(74) *Attorney, Agent, or Firm* — Morgan, Lewis & Bockius LLP

(57) ABSTRACT

A transformant obtained by introducing a DNA of (a1), (a2), or (a3) below, and (b) an alcohol dehydrogenase gene, into a bacterium of the genus *Hydrogenophilus*, can efficiently produce isobutanol utilizing carbon dioxide as a sole carbon source.

(a1) DNA which consists of a base sequence of SEQ ID NO: 1;

(a2) DNA which consists of a base sequence having 90% or more identity with SEQ ID NO: 1, the DNA encoding a polypeptide having 2-keto-acid decarboxylase activity;

(a3) DNA which hybridizes with a DNA consisting of a base sequence complementary to SEQ ID NO: 1 under stringent conditions, and which encodes a polypeptide having 2-keto-acid decarboxylase activity.

19 Claims, No Drawings
Specification includes a Sequence Listing.

(56) References Cited

OTHER PUBLICATIONS

Deng et al., "Ethanol Synthesis by Genetic Engineering in Cyanobacteria," Applied and Environmental Microbiology, 65 (2): 523-528 (1999).
Luan et al., "Combinatory strategy for characterizing and understanding the ethanol synthesis pathway in cyanobacteria cell factories," Biotechnology for Biofuels, 8: 184 (2015).
Keller et al., "Ethanol production by the hyperthermophilic archaeon Pyrococcus furiosus by expression of bacterial bifunctional alcohol dehydrogenases," Microbial Biotechnology, 10: 1535-1545 (2017).
Chung et al., "Cellulosic ethanol production via consolidated bioprocessing at 75 degrees Celsius by engineered Caldicellulosiruptor bescii," Biotechnology for Biofuels, 8: 163 (2015).
Wada et al., "Alanine production in an H+-ATPase– and lactate dehydrogenase-defective mutant of *Escherichia coli* expressing alanine dehydrogenase," Applied Microbiology and Biotechnology, 76: 819-825 (2007).
Lee et al., "Aerobic production of alanine by *Escherichia coli* aceF ldhA mutants expressing the Bacillus sphaericus alaD gene," Applied Microbiology and Biotechnology, 65: 56-60 (2004).
Uhlenbusch et al., "Expression of an L-Alanine Dehydrogenase Gene in Zymomonas mobilis and Excretion of L-Alanine," Applied and Environmental Microbiology, 57 (5): 1360-1366 (1991).
Hols et al., "Conversion of Lactococcus lactis from homolactic to homoalanine fermentation through metabolic engineering," Nature Biotechnology, 17: 588-592 (1999).
Jojima et al., "Engineering of sugar metabolism of Corynebacterium glutamicum for pdocution of amino acid L-alanine under oxygen deprivation," Applied Microbiology Biotechnology, 87: 159-165 (2010).
Journal of Mitsubishi Research Institute No. 34 1999 (see partial English translation).
Holland-Staley et al., "Aerobic Activity of *Escherichia coli* Alcohol Dehydrogenase Is Determined by a Single Amino Acid," Journal of Bacteriology, 182 (21): 6049-6054 (2000).
Goto et al., "Isolation and Culture Conditions of Thermophilic Hydrogen Bacteria," Agricultural and Biological Chemistry, 41 (4): 685-690 (1977).
Database GenBank, [online], Accession No. WP_013146672, Multispecies: alanine dehydrogenase [Geobacillus] (2019) (https://www.ncbi.nlm.nih.gov/protein/WP_013146672.1).
International Search Report issued in corresponding International Patent Application No. PCT/JP2018/024073 dated Sep. 11, 2018.
Majidian et al., "Metabolic engineering of microorganisms for biofuel production," Renewable and Sustainable Energy Reviews, 82: 3863-3885 (2018).
Chen et al., J Ind Microbiol Biotechnol, 42, 1473-1479, 2015.

* cited by examiner

SEQUENCE LISTING

```
Sequence total quantity: 111
SEQ ID NO: 1           moltype = DNA  length = 1647
FEATURE                Location/Qualifiers
misc_feature           1..1647
                       note = DNA coding a 2-keto-acid decarboxylase of
                       Lactococcus lactis
source                 1..1647
                       mol_type = other DNA
                       organism = synthetic construct
SEQUENCE: 1
atgtataccg tcggcgacta cctgctggat cgcctgcacg agctgggcat cgaggagatc   60
ttcggcgtcc cgggcgatta caatctgcag ttcctggatc agatcatctc gcgcaaggac  120
atgaaatggg tggcaatgc gaacgaactg aacgcctcgt acatggcgga tggctacgcg   180
cggaccaaga aggccgccgc cttcctgacc accttcggcg tcggcgaact gtcggcggtc  240
aatggcctgg cgggctccta cgcggaaaat ctgcccgtcg tcgagatcgt gggctcccg   300
acgtcgaagg tgcagaacga aggcaagttc gtgcaccaca cgctggccga cggcgacttc  360
aagcacttca tgaaaatgca tgagcccgtc accgccgcgc ggacgctgct gacggccgag  420
aacgccacgg tggaaatcga ccgggtcctg tcggcgctgc tgaaagagcg caagccggtc  480
tatatcaatc tgccggtgga cgtggccgcc gcgaaagcgg aaaagccctc cctgccgctg  540
aaaaaggaga attcgacctc gaatacgagc gaccaggaga tcctgaacaa gatccaggaa  600
agcctgaaaa acgcgaagaa gccgatcgtc atcaccggcc acgaaatcat ctcgttcggc  660
ctggagaaga ccgtctcgca gttcatctcc aagaccaagc tgccgatcac gacgctgaac  720
ttcggcaagt cgtccgtcga cgaagccctc cccagcttcc tgggcatcta caacggcaaa  780
ctgtccgagc ccaacctgaa agagttcgtc gagtcggcgg attttcatcct gatgctgggc  840
gtcaagctga ccgatagctc gaccggcgcg ttcacccatc acctgaacga gaacaagatg  900
atctcgctga atatcgacga aggcaaaatc ttcaacgagt cgatccagaa cttcgatttc  960
gaaagctga tctcctcgct gctggacctg agcgagatcg aatacaaggg caagtatatc 1020
gacaaaaagc aagaagactt cgtcccgagc aacgccctgc tgagccagga ccggctgtgg 1080
caggccgtcg aaaacctgac ccagtcgaat gaaaccatcg tcgcggagca gggcacctcg 1140
ttcttcggcg ccagctcgat cttcctgaag ccgaagtccc acttcatcgg ccagccgctg 1200
tgggctcca tcggctatac cttcccggcg ccctgggca gccagatcgc cgacaaggaa 1260
agccgccatc tgctgttcat cggcgacggc tcgctgcagc tgaccgtgca tgaactgggc 1320
ctggccatcc gcgagaagat caaccccatc tgcttcatca tcaataacga cggctacacc 1380
gtggagcggg aaatccacgg ccccaaccag agctacaacg acatcccgat gtggaattac 1440
tcgaaactgc ccgagtcgtt cggcgcgacc gaggaacggg tggtgtccaa gatcgtccgc 1500
accgagaatg agttcgtcag cgtgatgaag aagcccagg cggacccgaa ccgcatgtat 1560
tggatcgaac tgatcctggc gaaggaagac gcccccaagg tcctgaagaa gatgggcaag 1620
ctgttcgcgg agcagaacaa gagctaa                                     1647

SEQ ID NO: 2           moltype = DNA  length = 1011
FEATURE                Location/Qualifiers
source                 1..1011
                       mol_type = genomic DNA
                       organism = Klebsiella pneumoniae
SEQUENCE: 2
atgaaggcag ctgttgttac ccacgaccat caggttaacg tcacggaaaa aacgctgcgc   60
ccgctggaat acgcgaagc gctgttgaaa atggaatgct gcggcgtgtg tcatactgac  120
ctgcacgtga aaaacggcga tttttggcgat aaaaccggca tcattctcag ccatgaaggg  180
atcggggtgg tacaaaaagt cggcccgggc gtcacctccc tgaagccggg cgaccgcgcc  240
agcgtggcgt ggttcttcga aggctgcggc cactgcgatt actgtaacag cggcaacgag  300
acgctctgcc gctcggtgaa aaacgccggc tataccgtcg atggcggcat ggcggaagag  360
tgcatcgtca ccgccaacta gcgggtaaaa gttccggacg gcctcgactc cgccgccgcc  420
agcagcatca cctgcgcggg cgtcaccacc tacaaagcgg tcaaggtctc ccacatcaaa  480
ccgggccagt ggatcgccat ctacggcctc ggcgggttgg gtaacctcgc gctgcagtat  540
gcgaagaatg tctttaacgc caaagtgatc gctatcgacg tcaacgacgg acagctggag  600
ctggcggcct cgatgggcgc cgacctgacc atcaactccc gcaatgaaga tgcggcgaaa  660
gtgattcagg aaaaaaccgg cggcgcccac gctgcggtag taaccgcggt ggccaaagcg  720
gcctttaact cggcggtgga tgccgttcgc gccggtggcc gcgtggtcgc ggtgggcctg  780
ccgccggagc cgatgagcct cgatattccg cgtctggtgc tggacggcat cgaggtggtc  840
ggttcgctgg tcggcacccg tcaggatctg gtggaagcct tccagtttgc cgccgaaggc  900
aaagtagtgc cgaaagtcac cctgcgtccg ctggaagata tcaacgctat cttcaaagag  960
atggagcaag gtcagatccg cggccgtatg gttatcgatc tgcgtagcta a           1011

SEQ ID NO: 3           moltype = DNA  length = 1011
FEATURE                Location/Qualifiers
source                 1..1011
                       mol_type = genomic DNA
                       organism = Geobacillus thermocatenulatus
SEQUENCE: 3
atgaaagccg ccgttgttca aaattcaaa caaaaacttc aaattgaaga agtggagaaa   60
ccaaaactag gtatggcga agtgcttgtg aaaattgaag cttgtggcgt ctgccataccc  120
gatttgcatg cggcccatgg agattggcca gtaaaaccga aacttccgct tattcctggt  180
catgaggag taggaatcgt tgttgaggtc ggcgaggtga gtgaaatcaat caaaaattgac  240
gatcgtgttg gcattccatg gttatactcg gcatgcggtg aatgtgaata ttgttaagc   300
ggtcaagaaa cactttgtcc acatcaatta aatggtggat actctgtcga tggcagttat  360
gcagaatatt gcaagccccc ggccgattat gtcgcacgaa ttcctaaaaa tctcgatcct  420
gtacaagttg ctcctattct ttgtgctgga gtcacaacgt ataaagcatt aaaagtttca  480
aatgccaagc ctggtgaatg ggtcgctatt tatggaatcg ggggattggg ccatattgct  540
```

-continued

```
cttcaatatg ccaaagcaat gggattaaat gtcgttgctg ttgatatcag tgatgaaaag    600
gcagagcttg cagcaaagtt aggagctgat attacaatca atggcctgcg tgaagacccc    660
gtagcaacaa ttcgtgaaaa agtaggcgga gtgcatgcag ctattagcgt tgctgtaacg    720
aaaaaagctt tcgaacaagc ctatcaatcc gttcgacgcg tggttgcct tgtcatcgtt     780
ggactgcctc acgatgaact accgatccct attttgaca ctgtattaaa tggcgttaca     840
ataaaaggtt cgatcgtcgg tacacgaaaa gatatgcaag aagctttaga tttcgccgca    900
cgcggaaaag ttcgccccat tgtggaagcg gtaccattag aaaaaattaa cgaagtattt    960
gaacggatgg aaaaaggcca aatcaatggc cgcattgttt aacaatgta a              1011

SEQ ID NO: 4            moltype = DNA   length = 1023
FEATURE                 Location/Qualifiers
source                  1..1023
                        mol_type = genomic DNA
                        organism = Geobacillus thermoglucosidasius
SEQUENCE: 4
atgaaagcgg cagttgtcaa cgattttaaa caaaaattag aaattaaaga ggtggaaaaa    60
ccaaagctaa actacggaga agtgcttgtc aaaattgagg cttgcggcgt tgccacacc     120
gatttgcatg cggcgcacgg agactggcca gtcaagccaa aactgccttt gattcccgga    180
cacgaagggg taggcattgt cgtcgaggtg gcagaagggg taaaatcggt taaagtcggc    240
gaccgtgtcg gcattccatg gctatactcc gcttgcggag aatgtgaata ttgcctaagc    300
gggcaagaaa cgctctgtcc gcatcaatta acggtggat attccgccga tggaggatat    360
gcggaatact gcaaagcgcc tgccaattat gttgcaaaaa ttccgaaca cttggatccg    420
gtggaagtcg cgccaattct ctgcgcgggt gtaacgacat ataaagcgct aaaggtatct    480
aacgccaaac cggagaatgg gtagccatc tacggaatcg gagggttagg catatcgcc     540
cttcaatacg cgaaagcaat gggattaaac gtcgtcgcgg tcgatattag cgacgaaaag    600
atagatctcg ccaaacagtt aggcgctgat attgccatca acggacgaaa agaggatccg    660
gtggaagcca ttcatcaaaa cgttggcgga gtacatgccg ccattagcgt tgccgtaacg    720
aaaaaagcgt tcgaacaagc ctatcaatcc gtaagacgcg gcgatgcct tgttgttgtc    780
ggactgccta atgaagactt gccgattcct attttcaata cggtattaaa cggaatcacg    840
gtgaaaggat cgatcgtcgg cacgagaaaa gatatgcaag acgcgttgga cttcgccgcg    900
aaaggaaaag tgcgcccgat cgtcgaaacc gctccattgg aaaaaatcaa tgaagtattt    960
gagagaatgg aaaaaggaaa aattaacggc cgagtcgttt aaccattggt tgtcaaccgc    1020
taa                                                                  1023

SEQ ID NO: 5            moltype = DNA   length = 1041
FEATURE                 Location/Qualifiers
source                  1..1041
                        mol_type = genomic DNA
                        organism = Geobacillus thermoglucosidasius
SEQUENCE: 5
atgaaagcac ttacatacct agggccagga aaaaagaat taatgaaaaa accaaagcca     60
aaaattgaaa aggaaaccga tgcaatcgtc aaaataataa aaacaacgat tgtggaacga    120
gatttgcaca ttctttcagg agatgttcct actgttgaag agggcggat tttaggacac    180
gaaggcgtcg gaattattga agaagttggt tcggccgtaa agaattttaa aaaaggcgac    240
agagtgttga tttcttgcat tacctcttgt ggaaaatgcg aaaattgcaa gaaagggtta    300
tacgccatt gcgaagatgg cggctggatc ttgggccact taattgatgg aactcaagca    360
gaatatgtaa gaattccgca cgcagacaac agcctttatc ctattccgga aggcgtggat    420
gaagagactc ttgtcatgct tagtgacatt cttccaacag gatttgaaat cggcgtgttg    480
aacggcaaag ttcagcctgg acaaaccgtc gccattatcg gagctggtcc cgtaggctatg    540
gcagcgctat aacagcccca atttattca ccagcagaga tcattatggt tgatttagac    600
gataaccgtt tagaagttgc gaaaaaattt ggcgcgaccc aatggtgaa tagcgctgat    660
ggcaaggcag tggaaaaaat tatgaatta accggcggga aagtgtaga cgtcgcgatg    720
gaagccgtcg gaattccggc aacatttgat atttgtcaag aaattgtcaa accaggtggc    780
tatatcgcca atatcggtgt tcatggaaaa agcgtgaat tcacattga aaattatgg     840
atacgaaaca ttacgttgac aaccggtctt gtcaacacga cttctacgcc gatgttatta    900
aaaacggtgc agtcgaaaaa attgaagccg aacaattaa ttacccatcg tttcgccttt     960
tcagacatta tgaagcgta tgaagtattt ggaaatgcag caaagaaaa agcgttaaaa    1020
gtcattattt ccaacagtta a                                             1041

SEQ ID NO: 6            moltype = AA   length = 336
FEATURE                 Location/Qualifiers
source                  1..336
                        mol_type = protein
                        organism = Klebsiella pneumoniae
SEQUENCE: 6
MKAAVVTHDH QVNVTEKTLR PLEYGEALLK MECCGVCHTD LHVKNGDFGD KTGVILGHEG    60
IGVVQKVGPG VTSLKPGDRA SVAWFFEGCG HCDYCNSGNE TLCRSVKNAG YTVDGGMAEE    120
CIVTANYAVK VPDGLDSAAA SSITCAGVTT YKAVKVSHIK PGQWIAIYGL GGLGNLALQY    180
AKNVFNAKVI AIDVNDGQLE LAASMGADLT INSRNEDAAK VIQEKTGGAH AAVVTAVAKA    240
AFNSAVDAVR AGGRVAVGL PPEAMSLDIP RLVLDGIEVV GSLVGTRQDL VEAFQFAAEG    300
KVVPKVTLRP LEDINAIFKE MEQGQIRGRM VIDLRS                              336

SEQ ID NO: 7            moltype = AA   length = 336
FEATURE                 Location/Qualifiers
source                  1..336
                        mol_type = protein
                        organism = Geobacillus thermocatenulatus
SEQUENCE: 7
MKAAVVHKFK QKLQIEEVEK PKLGYGEVLV KIEACGVCHT DLHAAHGDWP VKPKLPLIPG    60
```

```
HEGVGIVVEV GEGVKSIKIG DRVGIPWLYS ACGECEYCLS GQETLCPHQL NGGYSVDGSY   120
AEYCKAPADY VARIPKNLDP VQVAPILCAG VTTYKALKVS NAKPGEWVAI YGIGGLGHIA   180
LQYAKAMGLN VVAVDISDEK AELAAKLGAD ITINGLREDP VATIREKVGG VHAAISVAVT   240
KKAFEQAYQS VRRGGCLVIV GLPHDELPIP IFDTVLNGVT IKGSIVGTRK DMQEALDFAA   300
RGKVRPIVEA VPLEKINEVF ERMEKGQING RIVLTM                            336

SEQ ID NO: 8            moltype = AA  length = 340
FEATURE                 Location/Qualifiers
source                  1..340
                        mol_type = protein
                        organism = Geobacillus thermoglucosidasius
SEQUENCE: 8
MKAAVVNDFK QKLEIKEVEK PKLNYGEVLV KIEACGVCHT DLHAAHGDWP VKPKLPLIPG    60
HEGVGIVVEV AEGVKSVKVG DRVGIPWLYS ACGECEYCLS GQETLCPHQL NGGYSADGGY   120
AEYCKAPANY VAKIPEHLDP VEVAPILCAG VTTYKALKVS NAKPGEWVAI YGIGGLGHIA   180
LQYAKAMGLN VVAVDISDEK IDLAKQLGAD IAINGRKEDP VEAIHQNVGG VHAAISVAVT   240
KKAFEQAYQS VRRGGCLVVV GLPNEDLPIP IFNTVLNGIT VKGSIVGTRK DMQEALDFAA   300
KGKVRPIVET APLEKINEVF ERMEKGKING RVVLTIGVNR                        340

SEQ ID NO: 9            moltype = AA  length = 346
FEATURE                 Location/Qualifiers
source                  1..346
                        mol_type = protein
                        organism = Geobacillus thermoglucosidasius
SEQUENCE: 9
MKALTYLGPG KKELMEKPKP KIEKETDAIV KIIKTTICGT DLHILSGDVP TVEEGRILGH    60
EGVGIIEEVG SAVKNFKKGD RVLISCITSC GKCENCKKGL YAHCEDGGWI LGHLIDGTQA   120
EYVRIPHADN SLYPIPEGVD EETLVMLSDI LPTGFEIGVL NGKVQPGQTV AIIGAGPVGM   180
AALLTAQFYS PAEIIMVDLD DNRLEVAKKF GATQVVNSAD GKAVEKIMEL TGGKGVDVAM   240
EAVGIPATFD ICQEIVKPGG YIANIGVHGK SVEFHIEKLW IRNITLTTGL VNTTSTPMLL   300
KTVQSKKLKP EQLITHRFAF SDIMKAYEVF GNAAKEKALK VIISNS                 346

SEQ ID NO: 10           moltype = DNA  length = 1692
FEATURE                 Location/Qualifiers
source                  1..1692
                        mol_type = genomic DNA
                        organism = Gluconobacter oxydans
SEQUENCE: 10
atgacttata ctgtcggaca ttatcttgcc gaacgactga cacagatcgg cctgaagcat    60
catttcgccg ttgccggcga ctacaacctc gttctgctcg accagctgat cgaacagggc   120
ggcacgaagc agatctatga ctgcaacgag ctgaactgca gcttcgccgc cgaaggttat   180
gcccgcgcca acggtgcagc cgctgccgtc atcaccttca gcgtcggcgc catctccgcc   240
atgaacgggc tcggcggcgc ctatgccgag aacctgccga tcctcgtgat ttcgggcgcg   300
ccgaactcca acgatcacgg ttcgggccca gtcctgcacc acacgatcgg cacgacggac   360
tacagctacc agatggaaat ggcgaagcac gttacctgtg ccgccgaaag catcacctct   420
gctgaaaccc cccggccaa gatcgaccac gtcatccgca cgatgctgcg tgagaagaag   480
ccggcctatc tcgaaatcgc ctgcaacatc tcggccgaca gcgcaccgtg tccggccgcg   540
gtctcgtccc tgcacgccca tccgcgtccg gacgaagcca gctgaaggc cgctctggac   600
gagagcctga gcttcctcaa caaggccaac aaggtcgcca tcctggtcgg caccaagctg   660
cgcgcagccg aagccctcaa ggaaacggtc gaactggctg acaagctcgg ttgccccgtt   720
acggtcatgg ccgctgcaaa gagctacttc ccgagacgc cccgggctt ccgtggcggt   780
tactggggcg acgtcagcag cccgggcgcc caggaaatca tcgaaggcgc cgatgccgtc   840
atctgcctgg caccagtctg gaatgactac tcctcgggcg gctggaagag cgttgtccgt   900
ggcgaaaagg tcctcgaggt cgatcccaac cgcgtcaccg tcaacggcaa gaccttcgaa   960
ggcttccgcc tgaaggaatt cgtcaaggcc tgaccgaga aggctccgaa gaagtccgca  1020
gccctgaccg gcgaatacaa gcccgtcatg ctgcctaagg ccgacccgtc caagccgctg  1080
tccaacgacg aaatgacccg ccagatcaac gaactggtcg acggcaacac cacgctcttc  1140
gccgagaccg gcgactcatg gttcaacgcc gtgcgtatgc accttcccga aggtgcgaag  1200
gtcgagacgg aaatgcagtg gggtcacatc ggctggtccg ttccgtccat gttcggcaac  1260
gccaccgctt cgccggagcg caagcacgtc ctgatgccgg gtgacggttc cttccagctg  1320
acggcgcagg aagtgcccca gatggtccga tacgaactgc cggtcatcat cttcctggtg  1380
aacaaccacg gctacgtcat cgaaatcgcc atccatgacg cccgtacaa ctacatccag  1440
aactgggact acgcagctct gatgcagtgc ttcaaccagg gcgtcccggg cgaggaaagc  1500
ggcaagtacg gtctcggcct gcatgccacg accggtgcag aactggcgga agccatcgcc  1560
aaggccaaga gaacacccg cggcccgacg ctcatcgagt gcaagcttga tcgtacggac  1620
tgcaccaaga ccctcgtgga gtggggcaag gctgttgccg ccgcaaactc ccgcaagccc  1680
cagagcgtct aa                                                    1692

SEQ ID NO: 11           moltype = AA  length = 563
FEATURE                 Location/Qualifiers
source                  1..563
                        mol_type = protein
                        organism = Gluconobacter oxydans
SEQUENCE: 11
MTYTVGHYLA ERLTQIGLKH HFAVAGDYNL VLLDQLIEQG GTKQIYDCNE LNCSFAAEGY    60
ARANGAAAAV ITFSVGAISA MNGLGGAYAE NLPILVISGA PNSNDHGSGH VLHHTIGTTD   120
YSYQMEMAKH VTCAAESITS AETAPAKIDH VIRTMLREKK PAYLEIACNI SAAPCVRPGP   180
VSSLHAHPRP DEASLKAALD ESLSFLNKAN KVAILVGTKL RAAEALKETV ELADKLGCPV   240
TVMAAAKSYF PETHPGFRGV YWGDVSSPGA QEIIEGADAV ICLAPVWNDY SSGGWKSVVR   300
```

```
GEKVLEVDPN RVTVNGKTFE GFRLKEFVKA LTEKAPKKSA ALTGEYKPVM LPKADPSKPL     360
SNDEMTRQIN ELVDGNTTLF AETGDSWFNA VRMHLPEGAK VETEMQWGHI GWSVPSMFGN     420
ATASPERKHV LMVGDGSFQL TAQEVAQMVR YELPVIIFLV NNHGYVIEIA IHDGPYNYIQ     480
NWDYAALMQC FNQGVPGEES GKYGLGLHAT TGAELAEAIA KAKKNTRGPT LIECKLDRTD     540
CTKTLVEWGK AVAAANSRKP QSV                                            563

SEQ ID NO: 12           moltype = DNA   length = 2676
FEATURE                 Location/Qualifiers
source                  1..2676
                        mol_type = genomic DNA
                        organism = Escherichia coli
SEQUENCE: 12
atggctgtta ctaatgtcgc tgaacttaac gcactcgtag agcgtgtaaa aaaagcccag     60
cgtgaaatatg ccagtttcac tcaagagcaa gtagacaaaa tcttccgcgc cgccgctctg    120
gctgctgcag atgctcgaat cccactcgcg aaaatggccg ttgccgaatc cggcatgggt    180
atcgtcgaag ataaagtgat caaaaaccac tttgcttctg aatatatcta caacgcctat    240
aaagatgaaa aaacctgtgg tgttctgtct gaagacgaca cttttggtac catcactatc    300
gctgaaccaa tcggtattat ttgcggtatc gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga agatctgat cggctggatc gatcaacctt ctgttgaact gtctaacgca     540
ctgatgcacc acccagacat caacctgatc ctcgcgactg gtggtccggg catggttaaa    600
gccgcataca gctccggtaa accagcatc ggtgtaggcg cgggcaacac tccagttgtt     660
atcgatgaaa ctgctgatat caaacgtgca gttcatctg tactgatgtc caaaaccttc     720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgtgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaagcaga gaaactgctt    1080
gctatgggcg gtatcggtca tacctcttgc ctgtacactg accaggataa ccaaccggct   1140
cgcgtttctt acttcggtca gaaaatgaaa acggcgcgta tcctgattaa cacccagcg    1200
tctcagggtg gtatcggtga cctgtataac ttcaaactcg caccttccct gactctgggt    1260
tgtggttctt ggggtggtaa ctccatctct gaaaacgttg gtccgaaaca cctgatcaac    1320
aagaaaaccg ttgctaagcg agctgaaaac atgttgtgc acaaacttcc gaaatctatc    1380
tacttccgcc gtggctccct gccaatgcgc ctggatgaag tgattactga tggccacaaa    1440
cgtgcgctca tcgtgactga ccgcttcctg ttcaacaatg ttatgctga tcagatcact    1500
tccgtactga agcagcagg cgttgaaact gaagtcttct tcgaagtaga agcggacccg    1560
accctgagca tcgttcgtaa aggtgcagaa ctggcgaaac ccttcaaacc agacgtgatt   1620
atcgcgctgg gtggtggttc cccgatggac gccgcgaaga tcatgtgggt tatgtacgaa    1680
catccggaaa ctcacttcga agagctgcg ctgcgcttta tggatatccg taaacgtatc     1740
tacaagttcc cgaaaatggg cgtgaaagcg aaaatgatcg ctgtcaccac cacttctggt    1800
acaggttctg aagtcactcc gtttgcggtt taactgacgg acgtcactgg tcagaaatat    1860
ccgctggcag actatgcgct gactccggat atggcgattc tcgacgccaa cctggttatg    1920
gacatgccga gtccctgtg tgctttcggt ggtctggacg cagtaactca cgccatggaa    1980
gcttatgttt ctgtactggc atctgagttc tctgatggtc aggctctgca ggcactgaaa    2040
ctgctgaaag aatatctgcc agcgtcctac cacgaaggt ctaaaaatcc gtagccgcgt    2100
gaacgtgttc acagtgcagc gactatcgcg ggtatcgcgt ttgcgaacgc cttcctgggt    2160
gtatgtcact caatggcgca caactgggt tcccagttcc atattccgca cggtctggca    2220
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctgaaaa cgctgaaagc tgaactgggg attccgaaat ctatccgtga agctggcgtt    2460
caggaagcag acttcctggc gaacgtggat aaactgtctg aagatgcatt cgatgaccag    2520
tgcaccggcg ctaacccgcg ttacccgctg atctccgagc tgaaacagat tctgctggat    2580
acctactacg gtcgtgatta tgtagaaggt gaaactgaca cgaagaaaga agctgctccg    2640
gctaaagctg agaaaaaagc gaaaaaatcc gcttcaa                             2676

SEQ ID NO: 13           moltype = DNA   length = 2622
FEATURE                 Location/Qualifiers
source                  1..2622
                        mol_type = genomic DNA
                        organism = Clostridium thermocellum
SEQUENCE: 13
atgacgaaaa tagcgaataa atacgaagtt attgataatg ttgaaaagct tgaaaaggct     60
ttgaaacgtt taagagaagc tcaaagtgtt tatgcaacct atacacagga gcaggttgac    120
aaaatttct ttgaggcggc aatggcggcc aataaaatga aattcctct tgccaaaatg     180
gctgtggagg aaacaggcat gggagtggtt gaagcaaagg ttatcaaaaa ccactatgct    240
tctgagtata tctataatgc gtacaaaaac actaaaacct gcggtgttat tgaagaggac    300
cctgctttcg gtattaaaaa aatagcagag cctttggggg ttattgcggc ggttatacct    360
actacgaatc cgacatcgac agcaatcttt aagactctta ttgcattaaa gacgagaaat    420
gcaattatta taagcccaca ccccaggca aaaaactcaa cgatagaagc ggcgaaaatt     480
gttttggagg cggccgttaa agccggtgct cggaaggca tcattggctg gattgatgtg    540
ccgagccttg aacttaccaa cctggtaatg agagaaggca agtgaattgt cgcaacaggc    600
ggtccggac tggttaaagc agcttactct tcgggcaaac cggcattgg tgtcggagcc    660
ggcaatactc ctgcaattat tgatgattcg gccgacattg tcttggcagt gaactcaata    720
atacattcaa aaactttcga caacggtatg atttgtgctt cagagcaatc ggtcattgtt    780
ctggacgggg tatataaaga ggtaaaaaaa gaatttgaaa aagaggatg ctatttctta    840
aatgaagatg aaactgaaaa ggtaagaaaa acaattataa taaacggtgc gttaaatgcc    900
```

```
aagatagtag gtcagaaagc tcacacaatt gcaaacccttg caggttttga ggtacccgag    960
actacaaaaa ttctgatagg cgaagttacc agcgtggata tttccgaaga atttgcccac   1020
gaaaagttgt gcccggtact ggcaatgtac agggcaaagg attttgacga tgcccttgat   1080
aaagcagaaa ggttggtagc tgacggtgga tttggccata cttcgtcact ttatatagat   1140
acggtaacac agaaagagaa acttcagaaa ttctctgaaa ggatgaaaac ctgccgtata   1200
ttggttaata cgccgtcatc ccagggaggg atccggtgacc tttacaactt caagcttgct   1260
ccgtctctca ccctcggctg cggttcctgg ggaggaaatt cagttccga caatgtggga   1320
gtcaagcatt tgttaaacat taaaacagtt gccgagagga gagaacat gctctggttc   1380
agaacacctg aaaagattta tataaaaaga ggttgtctgc ctgttgcatt ggatgagctt   1440
aaaaatgtaa tgggtaaaaa gaaagcattt attgtaacgg ataacttcct gtacaataac   1500
ggctacacca agccgattac ggataagctg gatgaaatgg gaattgtgca caagaccttc   1560
tttgatgtgt ctccagaccc atcccttgca tctgccaaag ccggtgcggc agaaatgctg   1620
gctttccagc ctgacaccat aattgcggtc ggcggcggat ctgccatgga cgcggccaaa   1680
atcatgtggg tgatgtatga acatccggaa gttgacttta tggacatggc aatgagattt   1740
atggatataa aaagagagt ttacaccttc ccgaagatgg gacagaaggc atactttatc   1800
gcaattccga cttccgcggg tacaggttca gaagtgacac cttttgcggt tattactgat   1860
gaaaaaacag gaattaaata ccctctggcc gactatgaat gttgccgga catggctatt   1920
gtagatgccg atatgatgat gaatgctcca aagggactta ccgcagcttc cggtatagac   1980
gcattgaccc acgctctgga agcctatgtt tcaatgcttg cgaccgacta tacggatagc   2040
cttgcccttc gtgcaataaa gatgatattt gaatatctcc cgagagccta tgaaaacggt   2100
gcaagtgacc cggttgcaag agagaaaatg gccaatgccg caacaatagc cggaatggct   2160
tttgccaaatg cctttttggg tgtatgccat tcaatgccgc acaaactggg tgcttttat   2220
cacctgcccc acggtgttgc caatgcactt atgataaacg aagtaatcag attcaactca   2280
tccgaggctc cgaccaagat gggtactttc ccgcagtatg accatccgcg cacgctggaa   2340
aggtatgcag aaattgccga ttatcggga cttaagggca agaataacga agaaaaagtt   2400
gaaaacttga ttaaagctat tgatgagctt aaagaaaagg tgggcatcag gaagaccatc   2460
aaagattatg acatagatga aaaggaattt ttggacagac tggacgaaat ggtggaacag   2520
gcttttgacg accagtgcac aggtacaaat ccaagatacc cgcttatgaa tgaaatcagg   2580
caaatgtatc tgaacgctta ttacggaggt gcgaagaaat aa                      2622

SEQ ID NO: 14          moltype = AA  length = 891
FEATURE                Location/Qualifiers
source                 1..891
                       mol_type = protein
                       organism = Escherichia coli
SEQUENCE: 14
MAVTNVAELN ALVERVKKAQ REYASFTQEQ VDKIFRAAAL AAADARIPLA KMAVAESGMG    60
IVEDKVIKNH FASEYIYNAY KDEKTCGVLS EDDTFGTITI AEPIGIICGI VPTTNPTSTA   120
IFKSLISLKT RNAIIFSPHP RAKDATNKAA DIVLQAAIAA GAPKDLIGWI DQPSVELSNA   180
LMHHPDINLI LATGGPGMVK AAYSSGKPAI GVGAGNTPVV IDETADIKRA VASVLMSKTF   240
DNGVICASEQ SVVVVDSVYD AVRERFATHG GYLLQGKELK AVQDVILKNG ALNAAIVGQP   300
AYKIAELAGF SVPENTKILI GEVTVVDESE PFAHEKLSPT LAMYRAKDFE DAVEKAEKLV   360
AMGGIGHTSC LYTDQDNQPA RVSYFGQKMK TARILINTPA SQGGIGDLYN FKLAPSLTLG   420
CGSWGGNSIS ENVGPKHLIN KKTVAKRAEN MLWHKLPKSI YFRRGSLPIA LDEVITDGHK   480
RALIVTDRFL FNNGYADQIT SVLKAAGVET EVFFEVEADP TLSIVRKGAE LANSFKPDVI   540
IALGGGSPMD AAKIMWVMYE HPETHFEELA LRFMDIRKRI YKFPKMGVKA KMIAVTTTSG   600
TGSEVTPFAV VTDDATGQKY PLADYALTPD MAIVDANLVM DMPKSLCAFG GLDAVTHAME   660
AYVSVLASEF SDGQALQALK LLKEYLPASY HEGSKNPVAR ERVHSAATIA GIAFANAFLG   720
VCHSMAHKLG SQFHIPHGLA NALLICNVIR YNANDNPTKQ TAFSQYDRPQ ARRRYAEIAD   780
HLGLSAPGDR TAAKIEKLLA WLETLKAELG IPKSIREAGV QEADFLANVD KLSEDAFDDQ   840
CTGANPRYPL ISELKQILLD TYYGRDYVEG ETAAKKEAAP AKAEKKAKKS A            891

SEQ ID NO: 15          moltype = AA  length = 873
FEATURE                Location/Qualifiers
source                 1..873
                       mol_type = protein
                       organism = Clostridium thermocellum
SEQUENCE: 15
MTKIANKYEV IDNVEKLEKA LKRLREAQSV YATYTQEQVD KIFFEAAMAA NKMRIPLAKM    60
AVEETGMGVV EDKVIKNHYA SEYIYNAYKN TKTCGVIEED PAFGIKKIAE PLGVIAAVIP   120
TTNPTSTAIF KTLIALKTRN AIIISPHPRA KNSTIEAAKI VLEAAVKAGA PEGIIGWIDV   180
PSLELTNLVM READVILATG GPGLVKAAYS SGKPAIGVGA GNTPAIIDDS ADIVLAVNSI   240
IHSKTFDNGM ICASEQSVIV LDGVYKEVKK EFEKRGCYFL NEDETEKVRK TIIINGALNA   300
KIVGQKAHTI ANLAGFEVPE TTKILIGEVT SVDISEEFAH EKLCPVLAMY RAKDFDDALD   360
KAERLVADGG FGHTSSLYID TVTQKEKLQK FSERMKTCRI LVNTPSSQGG IGDLYNFKLA   420
PSLTLGCGSW GGNSVSDNVG VKHLLNIKTV AERRENMLWF RTPEKIYIKR GCLPVALDEL   480
KNVMGKKKAF IVTDNFLYNN GYTKPITDKL DEMGIVHKTF FDVSPDPSLA SAKAGAAEML   540
APQPDTIIAV GGGSAMDAAK IMWVMYEHPE VDFMDMAMRF MDIRKRVYTF PKMGQKAYFI   600
AIPTSAGTGS EVTPFAVITD EKTGIKYPLA DYELLPDMAI VDADMMMNAP KGLTAASGID   660
ALTHALEAYV SMLATDYTDS LALRAIKMIF EYLPRAYENG ASDPVAREKM ANAATIAGMA   720
FANAFLGVCH SMAHKLGAFY HLPHGVANAL MINEVIRFNS SEAPTKMGTF PQYDHPRTLE   780
RYAEIADYIG LKGKNNEEKV ENLIKAIDEL KEKVGIRKTI KDYDIDEKEF LDRLDEMVEQ   840
AFDDQCTGTN PRYPLMNEIR QMYLNAYYGG AKK                                873

SEQ ID NO: 16          moltype = AA  length = 891
FEATURE                Location/Qualifiers
REGION                 1..891
                       note = mutant of Escherichia coli aldehyde-alcohol
                       dehydrogenase
```

| | | |
|---|---|---|
| source | 1..891 | |
| | mol_type = protein | |
| | organism = synthetic construct | |
| SEQUENCE: 16 | | |
| MAVTNVAELN | ALVERVKKAQ REYASFTQEQ VDKIFRAAAL AAADARIPLA KMAVAESGMG | 60 |
| IVEDKVIKNH | FASEYIYNAY KDEKTCGVLS EDDTFGTITI AEPIGIICGI VPTTNPTSTA | 120 |
| IFKSLISLKT | RNAIIFSPHP RAKDATNKAA DIVLQAAIAA GAPKDLIGWI DQPSVELSNA | 180 |
| LMHHPDINLI | LATGGPGMVK AAYSSGKPAI GVGAGNTPVV IDETADIKRA VASVLMSKTF | 240 |
| DNGVICASEQ | SVVVVDSVYD AVRERFATHG GYLLQGKELK AVQDVILKNG ALNAAIVGQP | 300 |
| AYKIAELAGF | SVPENTKILI GEVTVVDESE PFAHEKLSPT LAMYRAKDFE DAVEKAEKLV | 360 |
| AMGGIGHTSC | LYTDQDNQPA RVSYFGQKMK TARILINTPA SQGGIGDLYN FKLAPSLTLG | 420 |
| CGSWGGNSIS | ENVGPKHLIN KKTVAKRAEN MLWHKLPKSI YFRRGSLPIA LDEVITDGHK | 480 |
| RALIVTDRFL | FNNGYADQIT SVLKAAGVET EVFFEVEADP TLSIVRKGAE LANSFKPDVI | 540 |
| IALGGGSPMD | AAKIMWVMYE HPETHFEKLA LRFMDIRKRI YKFPKMGVKA KMIAVTTTSG | 600 |
| TGSEVTPFAV | VTDDATGQKY PLADYALTPD MAIVDANLVM DMPKSLCAFG GLDAVTHAME | 660 |
| AYVSVLASEF | SDGQALQALK LLKEYLPASY HEGSKNPVAR ERVHSAATIA GIAFANAFLG | 720 |
| VCHSMAHKLG | SQFHIPHGLA NALLLICNVIR YNANDNPTKQ TAFSQYDRPQ ARRRYAEIAD | 780 |
| HLGLSAPGDR | TAAKIEKLLA WLETLKAELG IPKSIREAGV QEADFLANVD KLSEDAFDDQ | 840 |
| CTGANPRYPL | ISELKQILLD TYYGRDYVEG ETAAKKEAAP AKAEKKAKKS A | 891 |

| | | |
|---|---|---|
| SEQ ID NO: 17 | moltype = AA   length = 891 | |
| FEATURE | Location/Qualifiers | |
| REGION | 1..891 | |
| | note = mutant of Escherichia coli aldehyde-alcohol dehydrogenase | |
| source | 1..891 | |
| | mol_type = protein | |
| | organism = synthetic construct | |
| SEQUENCE: 17 | | |
| MAVTNVAELN | ALVERVKKAQ REYASFTQEQ VDKIFRAAAL AAADARIPLA KMAVAESGMG | 60 |
| IVEDKVIKNH | FASEYIYNAY KDEKTCGVLS EDDTFGTITI AEPIGIICGI VPTTNPTSTA | 120 |
| IFKSLISLKT | RNAIIFSPHP RAKDATNKAA DIVLQAAIAA GAPKDLIGWI DQPSVELSNA | 180 |
| LMHHPDINLI | LATGGPGMVK AAYSSGKPAI GVGAGNTPVV IDETADIKRA VASVLMSKTF | 240 |
| DNGVICASEQ | SVVVVDSVYD AVRERFATHG GYLLQGKELK AVQDVILKNG ALNAAIVGQP | 300 |
| AYKIAELAGF | SVPENTKILI GEVTVVDESE PFAHEKLSPT LAMYRAKDFE DAVEKAEKLV | 360 |
| AMGGIGHTSC | LYTDQDNQPA RVSYFGQKMK TARILINTPA SQGGIGDLYN FKLAPSLTLG | 420 |
| CGSWGGNSIS | ENVGPKHLIN KKTVAKRAEN MLWHKLPKSI YFRRGSLPIA LDEVITDGHK | 480 |
| RALIVTDRFL | FNNGYADQIT SVLKAAGVET EVFFEVEADP TLSIVRKGAE LANSFKPDVI | 540 |
| IALGGGSPMD | AAKIMWVMYE HPETHFEALA LRFMDIRKRI YKFPKMGVKA KMIAVTTTSG | 600 |
| TGSEVTPFAV | VTDDATGQKY PLADYALTPD MAIVDANLVM DMPKSLCAFG GLDAVTHAME | 660 |
| AYVSVLASEF | SDGQALQALK LLKEYLPASY HEGSKNPVAR ERVHSAATIA GIAFANAFLG | 720 |
| VCHSMAHKLG | SQFHIPHGLA NALLLICNVIR YNANDNPTKQ TAFSQYDRPQ ARRRYAEIAD | 780 |
| HLGLSAPGDR | TAAKIEKLLA WLETLKAELG IPKSIREAGV QEADFLANVD KLSEDAFDDQ | 840 |
| CTGANPRYPL | ISELKQILLD TYYGRDYVEG ETAAKKEAAP AKAEKKAKKS A | 891 |

| | | |
|---|---|---|
| SEQ ID NO: 18 | moltype = AA   length = 891 | |
| FEATURE | Location/Qualifiers | |
| REGION | 1..891 | |
| | note = mutant of Escherichia coli aldehyde-alcohol dehydrogenase | |
| source | 1..891 | |
| | mol_type = protein | |
| | organism = synthetic construct | |
| SEQUENCE: 18 | | |
| MAVTNVAELN | ALVERVKKAQ REYASFTQEQ VDKIFRAAAL AAADARIPLA KMAVAESGMG | 60 |
| IVEDKVIKNH | FASEYIYNAY KDEKTCGVLS EDDTFGTITI AEPIGIICGI VPTTNPTSTA | 120 |
| IFKSLISLKT | RNAIIFSPHP RAKDATNKAA DIVLQAAIAA GAPKDLIGWI DQPSVELSNA | 180 |
| LMHHPDINLI | LATGGPGMVK AAYSSGKPAI GVGAGNTPVV IDETADIKRA VASVLMSKTF | 240 |
| DNGVICASEQ | SVVVVDSVYD AVRERFATHG GYLLQGKELK AVQDVILKNG ALNAAIVGQP | 300 |
| AYKIAELAGF | SVPENTKILI GEVTVVDESE PFAHEKLSPT LAMYRAKDFE DAVEKAEKLV | 360 |
| AMGGIGHTSC | LYTDQDNQPA RVSYFGQKMK TARILINTPA SQGGIGDLYN FKLAPSLTLG | 420 |
| CGSWGGNSIS | ENVGPKHLIN KKTVAKRAEN MLWHKLPKSI YFRRGSLPIA LDEVITDGHK | 480 |
| RALIVTDRFL | FNNGYADQIT SVLKAAGVET EVFFEVEADP TLSIVRKGAE LANSFKPDVI | 540 |
| IALGGGSPMD | AAKIMWVMYE HPETHFELLA LRFMDIRKRI YKFPKMGVKA KMIAVTTTSG | 600 |
| TGSEVTPFAV | VTDDATGQKY PLADYALTPD MAIVDANLVM DMPKSLCAFG GLDAVTHAME | 660 |
| AYVSVLASEF | SDGQALQALK LLKEYLPASY HEGSKNPVAR ERVHSAATIA GIAFANAFLG | 720 |
| VCHSMAHKLG | SQFHIPHGLA NALLLICNVIR YNANDNPTKQ TAFSQYDRPQ ARRRYAEIAD | 780 |
| HLGLSAPGDR | TAAKIEKLLA WLETLKAELG IPKSIREAGV QEADFLANVD KLSEDAFDDQ | 840 |
| CTGANPRYPL | ISELKQILLD TYYGRDYVEG ETAAKKEAAP AKAEKKAKKS A | 891 |

| | | |
|---|---|---|
| SEQ ID NO: 19 | moltype = AA   length = 891 | |
| FEATURE | Location/Qualifiers | |
| REGION | 1..891 | |
| | note = mutant of Escherichia coli aldehyde-alcohol dehydrogenase | |
| source | 1..891 | |
| | mol_type = protein | |
| | organism = synthetic construct | |
| SEQUENCE: 19 | | |

```
MAVTNVAELN ALVERVKKAQ REYASFTQEQ VDKIFRAAAL AAADARIPLA KMAVAESGMG  60
IVEDKVIKNH FASEYIYNAY KDEKTCGVLS EDDTFGTITI AEPIGIICGI VPTTNPTSTA 120
IFKSLISLKT RNAIIFSPHP RAKDATNKAA DIVLQAAIAA GAPKDLIGWI DQPSVELSNA 180
LMHHPDINLI LATGGPGMVK AAYSSGKPAI GVGAGNTPVV IDETADIKRA VASVLMSKTF 240
DNGVICASEQ SVVVVDSVYD AVRERFATHG GYLLQGELK AVQDVILKNG ALNAAIVGQP 300
AYKIAELAGF SVPENTKILI GEVTVVDESE PFAHEKLSPT LAMYRAKDFE DAVEKAEKLV 360
AMGGIGHTSC LYTDQDNQPA RVSYFGQKMK TARILINTPA SQGGIGDLYN FKLAPSLTLG 420
CGSWGGNSIS ENVGPKHLIN KKTVAKRAEN MLWHKLPKSI YFRRGSLPIA LDEVITDGHK 480
RALIVTDRFL FNNGYADQIT SVLKAAGVET EVFFEVEADP TLSIVRKGAE LANSFKPDVI 540
IALGGGSPMD AAKIMWVMYE HPETHFENLA LRFMDIRKRI YKFPKMGVKA KMIAVTTTSG 600
TGSEVTPFAV VTDDATGQKY PLADYALTPD MAIVDANLVM DMPKSLCAFG GLDAVTHAME 660
AYVSVLASEF SDGQALQOALK LLLKEYLPASY HEGSKNPVAR ERVHSAATIA GIAFANAFLG 720
VCHSMAHKLG SQFHIPHGLA NALLICNVIR YNANDNPTKQ TAFSQYDRPQ ARRRYAEIAD 780
HLGLSAPGDR TAAKIEKLLA WLETLKAELG IPKSIREAGV QEADFLANVD KLSEDAFDDQ 840
CTGANPRYPL ISELKQILLD TYYGRDYVEG ETAAKKEAAP AKAEKKAKKS A          891

SEQ ID NO: 20           moltype = AA   length = 891
FEATURE                 Location/Qualifiers
REGION                  1..891
                        note = mutant of Escherichia coli aldehyde-alcohol
                        dehydrogenase
source                  1..891
                        mol_type = protein
                        organism = synthetic construct
SEQUENCE: 20
MAVTNVAELN ALVERVKKAQ REYASFTQEQ VDKIFRAAAL AAADARIPLA KMAVAESGMG  60
IVEDKVIKNH FASEYIYNAY KDEKTCGVLS EDDTFGTITI AEPIGIICGI VPTTNPTSTA 120
IFKSLISLKT RNAIIFSPHP RAKDATNKAA DIVLQAAIAA GAPKDLIGWI DQPSVELSNA 180
LMHHPDINLI LATGGPGMVK AAYSSGKPAI GVGAGNTPVV IDETADIKRA VASVLMSKTF 240
DNGVICASEQ SVVVVDSVYD AVRERFATHG GYLLQGELK AVQDVILKNG ALNAAIVGQP 300
AYKIAELAGF SVPENTKILI GEVTVVDESE PFAHEKLSPT LAMYRAKDFE DAVEKAEKLV 360
AMGGIGHTSC LYTDQDNQPA RVSYFGQKMK TARILINTPA SQGGIGDLYN FKLAPSLTLG 420
CGSWGGNSIS ENVGPKHLIN KKTVAKRAEN MLWHKLPKSI YFRRGSLPIA LDEVITDGHK 480
RALIVTDRFL FNNGYADQIT SVLKAAGVET EVFFEVEADP TLSIVRKGAE LANSFKPDVI 540
IALGGGSPMD AAKIMWVMYE HPETHFEGLA LRFMDIRKRI YKFPKMGVKA KMIAVTTTSG 600
TGSEVTPFAV VTDDATGQKY PLADYALTPD MAIVDANLVM DMPKSLCAFG GLDAVTHAME 660
AYVSVLASEF SDGQALQOALK LLLKEYLPASY HEGSKNPVAR ERVHSAATIA GIAFANAFLG 720
VCHSMAHKLG SQFHIPHGLA NALLICNVIR YNANDNPTKQ TAFSQYDRPQ ARRRYAEIAD 780
HLGLSAPGDR TAAKIEKLLA WLETLKAELG IPKSIREAGV QEADFLANVD KLSEDAFDDQ 840
CTGANPRYPL ISELKQILLD TYYGRDYVEG ETAAKKEAAP AKAEKKAKKS A          891

SEQ ID NO: 21           moltype = AA   length = 891
FEATURE                 Location/Qualifiers
REGION                  1..891
                        note = mutant of Escherichia coli aldehyde-alcohol
                        dehydrogenase
source                  1..891
                        mol_type = protein
                        organism = synthetic construct
SEQUENCE: 21
MAVTNVAELN ALVERVKKAQ REYASFTQEQ VDKIFRAAAL AAADARIPLA KMAVAESGMG  60
IVEDKVIKNH FASEYIYNAY KDEKTCGVLS EDDTFGTITI AEPIGIICGI VPTTNPTSTA 120
IFKSLISLKT RNAIIFSPHP RAKDATNKAA DIVLQAAIAA GAPKDLIGWI DQPSVELSNA 180
LMHHPDINLI LATGGPGMVK AAYSSGKPAI GVGAGNTPVV IDETADIKRA VASVLMSKTF 240
DNGVICASEQ SVVVVDSVYD AVRERFATHG GYLLQGELK AVQDVILKNG ALNAAIVGQP 300
AYKIAELAGF SVPENTKILI GEVTVVDESE PFAHEKLSPT LAMYRAKDFE DAVEKAEKLV 360
AMGGIGHTSC LYTDQDNQPA RVSYFGQKMK TARILINTPA SQGGIGDLYN FKLAPSLTLG 420
CGSWGGNSIS ENVGPKHLIN KKTVAKRAEN MLWHKLPKSI YFRRGSLPIA LDEVITDGHK 480
RALIVTDRFL FNNGYADQIT SVLKAAGVET EVFFEVEADP TLSIVRKGAE LANSFKPDVI 540
IALGGGSPMD AAKIMWVMYE HPETHFESLA LRFMDIRKRI YKFPKMGVKA KMIAVTTTSG 600
TGSEVTPFAV VTDDATGQKY PLADYALTPD MAIVDANLVM DMPKSLCAFG GLDAVTHAME 660
AYVSVLASEF SDGQALQOALK LLLKEYLPASY HEGSKNPVAR ERVHSAATIA GIAFANAFLG 720
VCHSMAHKLG SQFHIPHGLA NALLICNVIR YNANDNPTKQ TAFSQYDRPQ ARRRYAEIAD 780
HLGLSAPGDR TAAKIEKLLA WLETLKAELG IPKSIREAGV QEADFLANVD KLSEDAFDDQ 840
CTGANPRYPL ISELKQILLD TYYGRDYVEG ETAAKKEAAP AKAEKKAKKS A          891

SEQ ID NO: 22           moltype = AA   length = 891
FEATURE                 Location/Qualifiers
REGION                  1..891
                        note = mutant of Escherichia coli aldehyde-alcohol
                        dehydrogenase
source                  1..891
                        mol_type = protein
                        organism = synthetic construct
SEQUENCE: 22
MAVTNVAELN ALVERVKKAQ REYASFTQEQ VDKIFRAAAL AAADARIPLA KMAVAESGMG  60
IVEDKVIKNH FASEYIYNAY KDEKTCGVLS EDDTFGTITI AEPIGIICGI VPTTNPTSTA 120
IFKSLISLKT RNAIIFSPHP RAKDATNKAA DIVLQAAIAA GAPKDLIGWI DQPSVELSNA 180
LMHHPDINLI LATGGPGMVK AAYSSGKPAI GVGAGNTPVV IDETADIKRA VASVLMSKTF 240
```

```
DNGVICASEQ SVVVVDSVYD AVRERFATHG GYLLQGKELK AVQDVILKNG ALNAAIVGQP    300
AYKIAELAGF SVPENTKILI GEVTVVDESE PFAHEKLSPT LAMYRAKDFE DAVEKAEKLV    360
AMGGIGHTSC LYTDQDNQPA RVSYFGQKMK TARILINTPA SQGGIGDLYN FKLAPSLTLG    420
CGSWGGNSIS ENVGPKHLIN KKTVAKRAEN MLWHKLPKSI YFRRGSLPIA LDEVITDGHK    480
RALIVTDRFL FNNGYADQIT SVLKAAGVET EVFFEVEADP TLSIVRKGAE LANSFKPDVI    540
IALGGGSPMD AAKIMWVMYE HPETHFERLA LRFMDIRKRI YKFPKMGVKA KMIAVTTTSG    600
TGSEVTPFAV VTDDATGQKY PLADYALTPD MAIVDANLVM DMPKSLCAFG GLDAVTHAME    660
AYVSVLASEF SDGQALQALK LLKEYLPASY HEGSKNPVAR ERVHSAATIA GIAFANAFLG    720
VCHSMAHKLG SQFHIPHGLA NALLICNVIR YNANDNPTKQ TAFSQYDRPQ ARRRYAEIAD    780
HLGLSAPGDR TAAKIEKLLA WLETLKAELG IPKSIREAGV QEADFLANVD KLSEDAFDDQ    840
CTGANPRYPL ISELKQILLD TYYGRDYVEG ETAAKKEAAP AKAEKKAKKS A             891

SEQ ID NO: 23           moltype = AA  length = 891
FEATURE                 Location/Qualifiers
REGION                  1..891
                        note = mutant of Escherichia coli aldehyde-alcohol
                        dehydrogenase
source                  1..891
                        mol_type = protein
                        organism = synthetic construct
SEQUENCE: 23
MAVTNVAELN ALVERVKKAQ REYASFTQEQ VDKIFRAAAL AAADARIPLA KMAVAESGMG     60
IVEDKVIKNH FASEYIYNAY KDEKTCGVLS EDDTFGTITI AEPIGIICGI VPTTNPTSTA    120
IFKSLISLKT RNAIIFSPHP RAKDATNKAA DIVLQAAIAA GAPKDLIGWI DQPSVELSNA    180
LMHHPDINLI LATGGPGMVK AAYSSGKPAI GVGAGNTPVV IDETADIKRA VASVLMSKTF    240
DNGVICASEQ SVVVVDSVYD AVRERFATHG GYLLQGKELK AVQDVILKNG ALNAAIVGQP    300
AYKIAELAGF SVPENTKILI GEVTVVDESE PFAHEKLSPT LAMYRAKDFE DAVEKAEKLV    360
AMGGIGHTSC LYTDQDNQPA RVSYFGQKMK TARILINTPA SQGGIGDLYN FKLAPSLTLG    420
CGSWGGNSIS ENVGPKHLIN KKTVAKRAEN MLWHKLPKSI YFRRGSLPIA LDEVITDGHK    480
RALIVTDRFL FNNGYADQIT SVLKAAGVET EVFFEVEADP TLSIVRKGAE LANSFKPDVI    540
IALGGGSPMD AAKIMWVMYE HPETHFEHLA LRFMDIRKRI YKFPKMGVKA KMIAVTTTSG    600
TGSEVTPFAV VTDDATGQKY PLADYALTPD MAIVDANLVM DMPKSLCAFG GLDAVTHAME    660
AYVSVLASEF SDGQALQALK LLKEYLPASY HEGSKNPVAR ERVHSAATIA GIAFANAFLG    720
VCHSMAHKLG SQFHIPHGLA NALLICNVIR YNANDNPTKQ TAFSQYDRPQ ARRRYAEIAD    780
HLGLSAPGDR TAAKIEKLLA WLETLKAELG IPKSIREAGV QEADFLANVD KLSEDAFDDQ    840
CTGANPRYPL ISELKQILLD TYYGRDYVEG ETAAKKEAAP AKAEKKAKKS A             891

SEQ ID NO: 24           moltype = AA  length = 873
FEATURE                 Location/Qualifiers
REGION                  1..873
                        note = mutant of Clostridium thermocellum aldehyde-alcohol
                        dehydrogenase
source                  1..873
                        mol_type = protein
                        organism = synthetic construct
SEQUENCE: 24
MTKIANKYEV IDNVEKLEKA LKRLREAQSV YATYTQEQVD KIFFEAAMAA NKMRIPLAKM     60
AVEETGMGVV EDKVIKNHYA SEYIYNAYKN TKTCGVIEED PAFGIKKIAE PLGVIAAVIP    120
TTNPTSTAIF KTLIALKTRN AIIISPHPRA KNSTIEAAKI VLEAAVKAGA PEGIIGWIDV    180
PSLELTNLVM READVILATG GPGLVKAAYS SGKPAIGVGA GNTPAIIDDS ADIVLAVNSI    240
IHSKTFDNGM ICASEQSVIV LDGVYKEVKK EFEKRGCYFL NEDETEKVRK TIIINGALNA    300
KIVGQKAHTI ANLAGFEVPE TTKILIGEVT SVDISEEFAH EKLCPVLAMY RAKDFDDALD    360
KAERLVADGG FGHTSSLYID TVTQKEKLQK FSERMKTCRI LVNTPSSQGG IGDLYNFKLA    420
PSLTLGCGSW GGNSVSDNVG VKHLLNIKTV AERRENMLWF RTPEKIYIKR GCLPVALDEL    480
KNVMGKKKAF IVTDNFLYNN GYTKPITDKL DEMGIVHKTF FDVSPDPSLA SAKAGAEML    540
AFQPDTIIAV GGGSAMDAAK IMWVMYEHPE VDFMNMAMRF MDIRKRVYTF PKMGQKAYFI    600
AIPTSAGTGS EVTPFAVITD EKTGIKYPLA DYELLPDMAI VDADMMMNAP KGLTAASGID    660
ALTHALEAYV SMLATDYTDS LALRAIKMIF EYLPRAYENG ASDPVAREKM ANAATIAGMA    720
FANAFLGVCH SMAHKLGAFY HLPHGVANAL MINEVIRFNS SEAPTKMGTF PQYDHPRTLE    780
RYAEIADYIG LKGKNNEEKV ENLIKAIDEL KEKVGIRKTI KDYDIDEKEF LDRLDEMVEQ    840
AFDDQCTGTN PRYPLMNEIR QMYLNAYYGG AKK                                 873

SEQ ID NO: 25           moltype = DNA  length = 2676
FEATURE                 Location/Qualifiers
misc_feature            1..2676
                        note = mutant of Escherichia coli aldehyde-alcohol
                        dehydrogenase gene
source                  1..2676
                        mol_type = other DNA
                        organism = synthetic construct
SEQUENCE: 25
atggctgtta ctaatgtcgc tgaacttaac gcactcgtag agcgtgtaaa aaaagcccag     60
cgtgaatatg ccagtttcac tcaagagcaa gtagacaaaa tcttccgcgc cgccgctctg    120
gctgctgcag atgctcgaat cccactcgcg aaaatgccg ttgccgaatc cggcatgggt    180
atcgtcgaag ataaagtgat caaaaaccac tttgcttctg aatatatcta caacgcctat    240
aaagatgaaa aaacctgtgg tgttctgtct gaagacgaca cttttggtac catcactatc    300
gctgaaccaa tcggtattat tgcggtatcg gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
```

```
ggtgctccga aagatctgat cggctggatc gatcaacctt ctgttgaact gtctaacgca  540
ctgatgcacc acccagacat caacctgatc ctcgcgactg gtggtccggg catggttaaa  600
gccgcataca gctccggtaa accagctatc ggtgtaggcg cgggcaacac tccagttgtt  660
atcgatgaaa ctgctgatat caaacgtgca gttgcatctg tactgatgtc caaaaccttc  720
gacaacggcg taatctgtgc ttctgaacag tctgttgttg ttgttgactc tgtttatgac  780
gctgtacgtg aacgttttgc aacccacggc ggctatctgt tgcagggtaa agagctgaaa  840
gctgttcagg atgttatcct gaaaaacggt gcgctgaacg cggctatcgt tggtcagcca  900
gcctataaaa ttgctgaact ggcaggcttc tctgtaccag aaaacaccaa gattctgatc  960
ggtgaagtga ccgttgttga tgaaagcgaa ccgttcgcac atgaaaaact gtccccgact 1020
ctggcaatgt accgcgctaa agatttcgaa gacgcggtag aaaaagcaga gaaactgctt 1080
gctatgggcg gtatcggtca tacctcttgc ctgtacactg accaggataa ccaaccggct 1140
cgcgtttctt acttcggtca gaaatgaaa acggcgcgta tcctgattaa caccccagcg 1200
tctcagggtg gtatcggtga cctgtataac ttcaaactcg caccttccct gactctgggt 1260
tgtggttctt ggggtggtaa ctccatctct gaaaacgttg gtcccaaaca cctgatcaac 1320
aagaaaaccg ttgctaagcg agctgaaaac atgttgtggc acaaacttcc gaaatctatc 1380
tacttccgcc gtgctccct gccaatcgcg ctggatgaag tgattactga tggccacaaa 1440
cgtgcgctca tcgtgactga ccgcttcctg ttcaacaatg ttatgctga tcagatcact 1500
tccgtactga agcagcagg cgttgaaact gaagtcttct tcgaagtaga agcggacccg 1560
accctgagca tcgttcgtaa aggtgcagaa ctggcaaact ccttcaaacc agacgtgatt 1620
atcgcgctgg gtggtggttc cccgatggac gccgcgaaga tcatgtgggt tatgtacgaa 1680
catccggaaa ctcacttcga aaagctggcg ctgcgcttta tggatatccg taaacgtatc 1740
tacaagttcc cgaaaatggg cgtgaaagcg aaaatgatcg ctgtcaccac cacttctggt 1800
acaggttctg aagtcactcc gtttgcggtt gtaactgacg acgctactgg tcagaaatat 1860
ccgctggcag actatgcgct gactccggat atggcgattg tcgacgccaa cctggttatg 1920
gacatgccga agtccctgtg tgctttcggt ggtctggacg cagtaactca cgccatgaa 1980
gcttatgttt ctgtactggc atctgagttc tctgatgctc aggctctgca ggcactgaaa 2040
ctgctgaaag aatatctgcc agcgtcctac cacgaagggt ctaaaaatcc ggtagcgcgt 2100
gaacgtgttc acagtgcagc gactatcgcg ggtatcgcgt ttgcgaacgc cttcctgggt 2160
gtatgtcact caatgcgca caaactgggt tcccagttcc atattccgca cggtctggca 2220
aacgccctgc tgatttgtaa cgttattcgc tacaatgcga acgcaaccc gaccaagcag 2280
actgcattca gccagtatga ccgtccgcag gctcgccgtc gttatgctga aattgccgac 2340
cacttgggtc tgagcgcacc gggcgaccg actgctgcta agatcgagaa actgctggca 2400
tggctggaaa cgctgaaagc tgaactgggt attccgaaat ctatccgtga agctggcgtt 2460
caggaagcag acttcctggc gaactggat aaactctg aagatgcatt cgatgaccag 2520
tgcaccggcg ctaacccgcg ttaccgctg atctcgagc tgaaacagat tctgctggat 2580
acctactacg gtcgtgatta tgtagaaggt gaaactgcag cgaagaaaga agctgctccg 2640
gctaaagctg agaaaaaagc gaaaaaatcc gcttaa                            2676

SEQ ID NO: 26         moltype = DNA    length = 2676
FEATURE               Location/Qualifiers
misc_feature          1..2676
                      note = mutant of Escherichia coli aldehyde-alcohol
                      dehydrogenase gene
source                1..2676
                      mol_type = other DNA
                      organism = synthetic construct
SEQUENCE: 26
atggctgtta ctaatgtcgc tgaacttaac gcactcgtag agcgtgtaaa aaaagcccag 60
cgtgaatatg ccagtttcac tcaagagcaa gtagacaaaa tcttccgcgc cgccgctctg 120
gctgctgcag atgctcgaat cccactcgcg aaaatggccg ttgccgaatc cggcatgggt 180
atcgtcgaag ataaagtgat caaaaaccac tttgcttctg aatatatcta caacgccatc 240
aaagatgaaa aaacctgtgg tgttctgtct gaagacgaca cttttggtac catcactatc 300
gctgaaccaa tcggtattat tgcggtatc gttccgacca ctaacccgac ttcaactgct 360
atcttccaaat cgctgatcag tctgaagacc cgtaacgcca ttatcttctc cccgcacccg 420
cgtgcaaaag atgccaccaa caaagcggct gatatcgttc tgcaggctgc tatcgctgcc 480
ggtgctccga aagatctgat cggctggatc gatcaacctt ctgttgaact gtctaacgca 540
ctgatgcacc acccagacat caacctgatc ctcgcgactg gtggtccggg catggttaaa 600
gccgcataca gctccggtaa accagctatc ggtgtaggcg cgggcaacac tccagttgtt 660
atcgatgaaa ctgctgatat caaacgtgca gttgcatctg tactgatgtc caaaaccttc 720
gacaacggcg taatctgtgc ttctgaacag tctgttgttg ttgttgactc tgtttatgac 780
gctgtacgtg aacgttttgc aacccacggc ggctatctgt tgcagggtaa agagctgaaa 840
gctgttcagg atgttatcct gaaaaacggt gcgctgaacg cggctatcgt tggtcagcca 900
gcctataaaa ttgctgaact ggcaggcttc tctgtaccag aaaacaccaa gattctgatc 960
ggtgaagtga ccgttgttga tgaaagcgaa ccgttcgcac atgaaaaact gtccccgact 1020
ctggcaatgt accgcgctaa agatttcgaa gacgcggtag aaaaagcaga gaaactggtt 1080
gctatgggcg gtatcggtca tacctcttgc ctgtacactg accaggataa ccaaccggct 1140
cgcgtttctt acttcggtca gaaatgaaa acggcgcgta tcctgattaa caccccagcg 1200
tctcagggtg gtatcggtga cctgtataac ttcaaactcg caccttccct gactctgggt 1260
tgtggttctt ggggtggtaa ctccatctct gaaaacgttg gtcccaaaca cctgatcaac 1320
aagaaaaccg ttgctaagcg agctgaaaac atgttgtggc acaaacttcc gaaatctatc 1380
tacttccgcc gtgctccct gccaatcgcg ctggatgaag tgattactga tggccacaaa 1440
cgtgcgctca tcgtgactga ccgcttcctg ttcaacaatg ttatgctga tcagatcact 1500
tccgtactga agcagcagg cgttgaaact gaagtcttct tcgaagtaga agcggacccg 1560
accctgagca tcgttcgtaa aggtgcagaa ctggcaaact ccttcaaacc agacgtgatt 1620
atcgcgctgg gtggtggttc cccgatggac gccgcgaaga tcatgtgggt tatgtacgaa 1680
catccggaaa ctcacttcga aaagctggcg ctgcgcttta tggatatccg taaacgtatc 1740
tacaagttcc cgaaaatggg cgtgaaagcg aaaatgatcg ctgtcaccac cacttctggt 1800
acaggttctg aagtcactcc gtttgcggtt gtaactgacg acgctactgg tcagaaatat 1860
ccgctggcag actatgcgct gactccggat atggcgattg tcgacgccaa cctggttatg 1920
```

```
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatgcgcag caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg tcgtgatta tgtagaaggt gaaactgcag cgaagaaaga agctgctccg   2640
gctaaagctg agaaaaaagc gaaaaaatcc gcttaa                              2676

SEQ ID NO: 27         moltype = DNA   length = 2622
FEATURE               Location/Qualifiers
misc_feature          1..2622
                      note = mutant of Clostridium thermocellum aldehyde-alcohol
                      dehydrogenase gene
source                1..2622
                      mol_type = other DNA
                      organism = synthetic construct
SEQUENCE: 27
atgacgaaaa tagcgaataa atacgaagtt attgataatg ttgaaaagct tgaaaaggct   60
ttgaaacgtt aagagaagc tcaaagtgtt tatgcaacct atacacagga gcaggttgac   120
aaaatttct ttgaggcggc aatggcggcc aataaaatga gaattcctct tgccaaaatg   180
gctgtggagg aaacaggcat gggagtggtt gaagacaagg ttatcaaaaa ccactatgct   240
tctgagtata tctataatgc gtacaaaaac actaaaacct gcggtgttat tgaagaggac   300
cctgctttcg gtattaaaaa aatagcagag cctttgggg ttattgcggc ggttataacct   360
actacgaatc cgacatcgac agcaatcttt aagactctta ttgcattaaa gacgagaaat   420
gcaattatta taagcccaca ccccagggca aaaaactcaa cgatagaagc ggcgaaaatt   480
gttttggagg cggccgttaa agccggtgct ccggaaggca tcattggctg gattgatgtg   540
ccgagccttg aacttaccaa cctggtaatg agaagcag atgtgattct cgcaacaggc   600
ggtcccggac tggttaaagc agcttactct tcgggcaaac cggcattagg tgtcggagcg   660
ggcaataactc ctgcaattat tgatgattcg gccgacattg tcttggcagt gaactcaata   720
atacattcaa aaactttcga caacggtatg atttgtgctt cagagcaatc ggtcattgtt   780
ctggacgggg tatataaaga ggtaaaaaaa gaatttgaaa aaagaggatg ctatttctta   840
aatgaagatg aaactgaaaa ggtaagaaaa acaattataa taaacggtgc gttaaatgcc   900
aagatagtag gtcagaaagc tcacacaatt gcaaaccttg caggttttga ggtaccgag   960
actacaaaaa ttctgatagg cgaagttacc agcgtggata tttccgaaga atttgcccac   1020
gaaaagttgt gcccggtact ggcaatgtac agggcaaagg attttgacga tgcccttgat   1080
aaagcagaaa ggttggtagc tgacggtgga tttggccata cttcgtcact ttatatagat   1140
acggtaacac agaaagaaa acttcagaaa ttctctgaaa ggatgaaaac ctgccgtata   1200
ttggttaata cgccgtcatc ccagggaggt atcggtgacc tttacaactt caagcttgct   1260
ccgtctctca ccctcggctg cggttcctgg gaggaaatt cagtttccga caatgtggga   1320
gtcaagcatt tgttaaacat taaaacagtt gccgagagga gagaacat gctctggttc   1380
agaacacctg aaaagattta tataaaaaga ggttgtctgc ctgttgcatt ggatgagctt   1440
aaaaatgtaa tgggtaaaaa gaaagcattt attgtaacgg ataacttcct gtacaataac   1500
ggctacacca agccgattac ggataagctg gatgaaatgg gaattgtgca caagaccttc   1560
tttgatgtgt ctccagaccc atcccttgca tctgccaaag ccggtgcggc agaaatgctg   1620
gctttccagc ctgacaccat aattgcggtc ggcggcggat ctgccatgga cgcggccaaa   1680
atcatgtggg tgatgtatga acatccgaa gttgacttta tgaacatggc aatgagattt   1740
atggatataa gaaagagagt ttacacctt ccgaagatgg gacagaaggc atactttatc   1800
gcaattccga cttccgcggg tacaggttca gaagtgacac ctttgcggt tattactgat   1860
gaaaaaacag gaattaaata ccctctggcc gactatgaat tgttgccgga catggctatt   1920
gtagatgccg atatgatgat gaatgctcca aagggactta ccgcagcttc cggtatagac   1980
gcattgaccc acgctctgga agcctatgtt tcaatgcttg cgaccgacta tcggatagc   2040
cttgccctttc gtgcaataaa gatgatattt gaatatctcc cgagagccta tgaaaacggt   2100
gcaagtgacc cggttgcaag agagaaaatg gccaatgcca caacaatagc cggaatggct   2160
tttgccaatg cctttttggg tgtatgccat tcaatgcgc acaaactggg tgctttttat   2220
cacctgcccc acgtgttgc caatgcactt atgataaacg aagtaatcag attcaactca   2280
tccgaggctc cgaccaagat gggtactttc ccgcagtatg accatccgcg cacgctgaaa   2340
aggtatgcag aaattgccga ttatatcgga cttaagggca agaataacga agaaaaagtt   2400
gaaacttga ttaaagctat tgatgagctt aagaaaaagg tgggcatcga gaagccatc   2460
aaagattatg acatagatga aaaggaattt ttggacagag tggacgaaat ggtgaacag   2520
gcttttgacg accagtgcac aggtacaaat ccaagatacc cgcttatgaa tgaaatcagg   2580
caaatgtatc tgaacgctta ttacggaggt gcgaagaaat aa                      2622

SEQ ID NO: 28         moltype = DNA   length = 2622
FEATURE               Location/Qualifiers
misc_feature          1..2622
                      note = mutant of Clostridium thermocellum aldehyde-alcohol
                      dehydrogenase gene
source                1..2622
                      mol_type = other DNA
                      organism = synthetic construct
SEQUENCE: 28
atgacgaaaa tagcgaataa atacgaagtt attgataatg ttgaaaagct tgaaaaggct   60
ttgaaacgtt aagagaagc tcaaagtgtt tatgcaacct atacacagga gcaggttgac   120
```

```
aaaattttct ttgaggcggc aatggcggcc aataaaatga gaattcctct tgccaaaatg    180
gctgtggagg aaacaggcat gggagtggtt gaagacaagg ttatcaaaaa ccactatgct    240
tctgagtata tctataatgc gtacaaaaac actaaaacct gcggtgttat tgaagaggac    300
cctgctttcg gtattaaaaa aatagcagag cctttggggg ttattgcggc ggttatacct    360
actacgaatc cgacatcgac agcaatcttt aagactctta ttgcattaaa gacgagaaat    420
gcaattatta taagcccaca ccccagggca aaaaactcaa cgatagaagc ggcgaaaatt    480
gttttggagg cggccgttaa agccggtgct ccggaaggca tcattggctg gattgatgtg    540
ccgagccttg aacttaccaa cctggtaatg agagaagcag atgtgattct cgcaacaggc    600
ggtcccggac tggttaaagc agcttactct tcgggcaaac cggctattgg tgtcggaacg    660
ggcaatactc ctgcaattat tgatgattcg gccgacattg tcttggcagt gaactcaata    720
atacattcaa aaactttcga caacggtatg atttgtgctt cagagcaatc ggtcattgtt    780
ctggacgggt atataaaga ggtaaaaaaa gaatttgaaa aagaggatg ctatttctta     840
aatgaagatg aaactgaaaa ggtaagaaaa acaattataa taaacggtgc gttaaatgcc    900
aagatagtag gtcagaaagc tcacacaatt gcaaaccttg caggttttga ggtacccgag    960
actacaaaaa ttctgatagg cgaagttacc agcgtggata tttccgaaga atttgcccac   1020
gaaaagttgt gcccggtact ggcaatgtac agggcaaagg attttgacga tgcccttgat   1080
aaagcagaaa ggttggtagc tgacggtgga tttggccata cttcgtcact ttatatagat   1140
acggtaacac agaaagagaa acttcagaaa ttctctgaaa ggatgaaaac ctgccgtata   1200
ttggttaata cgccgtcatc ccagggaggt atccgtgacc tttacaactt caagcttgct   1260
ccgtctctca ccctcggctg cggttcctgg ggaggaaatt cagtttccga caatgtggga   1320
gtcaagcatt tgttaaacat taaaacagtt gccgagagga gagagaacat gctctggttc   1380
agaacacctg aaaagattta tataaaaaga ggttgtctgc ctgttgcatt ggatgagctt   1440
aaaaatgtaa tgggtaaaaa gaaagcattt attgtaacgg ataacttcct gtacaataac   1500
ggctacacca agccgattac ggataagctg gatgaaatgg gaattgtgca caagaccttc   1560
tttgatgtgt ctccagaccc atcccttgca tctgccaaag ccggtgcggc agaaatgctg   1620
gctttccagc ctgacaccat aaattgcggtc ggcggccatg gacgcggccaaa           1680
atcatgtggg tgatgtatga acatccggaa gttgactttta tgaatatgaa aatgagattt   1740
atggatataa gaaagagagt ttacacccttc ccgaagatgg gacagaaggc atactttatc   1800
gcaattccga cttccgcggg tacaggttca gaagtgacac cttttgcggt tattactgat   1860
gaaaaaacag gaattaaata ccctctggcc gactatgaat tgttgccgga catggctatt   1920
gtagatgccg atatgatgat gaatgctcca aagggactta ccgcagcttc cggtatagac   1980
gcattgaccc acgctctgga agcctatgtt tcaatgcttg cgaccgacta tacggatagc   2040
cttgcccttc gtgcaataaa gatgatattt gaatatctcc cgagagccta tgaaaacggt   2100
gcaagtgacc cggttgcaag agagaaaatg gccaatgccc caacaatagc cggaaatgcc   2160
tttgccaatg ccttttgggg tgtatgccat tcaatgcgcgc acaaactggg tgctttttat   2220
cacctgcccc acggtgttgc caatgcactt atgataaacg aagtaatcag attcaactca   2280
tccgaggctc cgaccaagat gggtactttc ccgcagtatg accatccgcg cacgctggaa   2340
aggtatgcag aaaattgccga ttatatcgga cttaagggca agaataacga agaaaaagtt   2400
gaaaacttga ttaaagctat tgatgagctt aaagaaaagg tgggcatcag gaagaccatc   2460
aaagattatg acatagatga aaaggaattt ttggacagaa tggacgaaat ggtgaacag    2520
gcttttgacg accagtgcac aggtacaaat ccaagatacc cgcttatgaa tgaaaatcagg  2580
caaatgtatc tgaacgctta ttacgaggt gcgaagaaat aa                       2622

SEQ ID NO: 29          moltype = DNA   length = 1119
FEATURE                Location/Qualifiers
source                 1..1119
                       mol_type = genomic DNA
                       organism = Geobacillus stearothermophilus
SEQUENCE: 29
atgaagatcg gcattccaaa agaaatcaaa aacaatgaaa accgcgtcgc catcactccg     60
gcaggcgtga tgacgctcgt caaagcgggg catgacgtgt atgtggagac ggaagccggc   120
gctgggtcgg ggttttctga cgctgaatat gaaaaagccg gggcagtgat cgtgacgaaa   180
gcggaagatg cctgggcggc ggagatggtt ttgaaagtga agaaccgct gcctgaggag    240
ttccgctatt ttcgccccgg attgattttg tttacgtatt tgcatttagc cgcggccgaa   300
gcgctcacga aagcgctcgt cgagcaaaaa gtggtcggca tcgcttacga gacggtgcag   360
cttgcgaacg gctcgctgcc gctgttgacg ccgatgagtg aagtcgccgg ccgcatgtcg   420
gtgcaagtcg gcgcccagtt tctcgagaag ccgcacggcg ggaaaggcat tttgcttggc   480
ggcgtgcccg gggtgcggcg cggcaaagtg acgatcatcg gcggcggcac agcggggacg   540
aacgcgggga aaatcgcggt cggcctcggg gcggacgtga cgattttgga cattaacgcc   600
gagcggctgc gcgagctcga tgatttgttc ggcgaccaag tgacgacgtt gatgtccaac   660
tcgtatcata tcgccgaatg cgtcgggaa tcggatttgg tcgtcggcgc cgtcttgatc    720
ccgggggcga aagcgccaaa gcttgtgacg aagagatgg tgcgctcgat gatgccaggc    780
tcggtgttgg tcgacgtcgc cattgaccaa ggcggcattt tcgaaacgac cgaccgcgtc    840
acgacgcacg acgatccgac atacgtcaag cacggcgtcg ttcattacgc cgtcgccgac   900
atgccgggcg ctgtgccgcg cacgtcgaca ttcgcgctta cgaacgtcac gatcccgtac   960
gccttgcaaa tcgccaacaa aggctaccgc gccgcgtgct tggataaccc ggcgctgtta   1020
aaagggatca cacgctcga cgggcacatc gtgtacgaag cggtcgcggc ggcgcacaac   1080
atgccgtata cggatgctca ttcgttgctg cagggatga                         1119

SEQ ID NO: 30          moltype = DNA   length = 1134
FEATURE                Location/Qualifiers
source                 1..1134
                       mol_type = genomic DNA
                       organism = Geobacillus stearothermophilus
SEQUENCE: 30
atgattattg gagtgccaaa ggaaatcaaa aataacgaaa accgtgtcgc cattacgccg     60
gctggcgttt tgtcattcgt tcaggctgga catacggttc tgattgagaa agaggcaggg    120
gttggaagcg gttcagcga cagcgattac gcccgtgccg gagcacaaat catcgagcgg    180
gcggaagatg tttgggcgca agccgatatg gtgatgaaag tgaaagagcc gctgccaagc   240
```

```
gaatacggct atttccgccc aggtctcatt ttgttcacct atttgcattt ggccgccgac   300
ccggagttga cacgcgcctt aaaagaaagc ggcgtcatcg ccattgccta tgagacggtg   360
caagtcggcc gcacactgcc gctgttgaca ccaatgagcg aagtcgccgg acggatggcc   420
gcgcaaattg gagcgcaatt tttagaaaaa ccgtacggcg gcaaaggcat cttgcttggc   480
ggcgtcccag gcgttgcccg cggcaaagtg acgatcgcag gcggcggagt cgtcggcacg   540
aacgcagcga agtcgcggt cggcctcggg gcagatgtca cgattatcga cttgaacgcg   600
gatcgcctgc gcgagcttga cgacattttc ggcaaccaaa ttacgacgct catgtccaac   660
ccaatgaaca tcgccgaagc ggttgctgag ccgaccttg tcatcggcgc cgtcctcatc   720
ccgggagcgc gggcgccgaa gctcgtcacc gaggacatgt gaaagcgat gaaacccggt   780
tcggtcatcg tcgatgtcgc catcgaccaa gggggcatcg tcgagacgag cgaccacgtc   840
acgacacatg acgacccgac gtacgtcaaa cacggcgtcg tccattatgc ggtcgccaac   900
atgcctggcg ccgtcccgcg cacctcaacg atcgccttga cgaacgtcac catgccatac   960
gccttgcaaa tcgccaacaa aggcgtcatc caagccatta cagacaaccc ggcgcttgag  1020
cttggcgtca acgtcgccaa cggtgaaatc acgtacgaag cggtcgcccg cgacctcggt  1080
taccgctacg tcccggcccg cgaagcgctc gggaaaacgt tggccgccaa ctaa        1134

SEQ ID NO: 31        moltype = DNA   length = 1110
FEATURE              Location/Qualifiers
source               1..1110
                     mol_type = genomic DNA
                     organism = Thermus thermophilus
SEQUENCE: 31
atggtgatcg gcgtgccgaa ggagatcaag accttggaga accgggtggc cctcacgccc   60
ggcggggtgg agagcctggt caggcgcggc cacaccgtgc tggtggagcg ggggccgggg  120
gagggctcgg gctttccga cgcggagtac gcccgggccg gggccgagct cgtgggccgg  180
gaggaggcct ggggtgcgga gatggtggtg aaggtgaagc ccctacc cgaggagtac   240
ggcttcctgc gggagggcct catcctcttc acctaccttc acctggccgc ggaccgcggc  300
ctcaccgagg ccatgctccg tagcggggtc acgggcatcg cctacgagac cgtccagctt  360
cccgacggca ccctccccct cctcgtcccc atgagcgagg tggcggggcg gatggccccc  420
caggtggggg cccagttcct ggagaagccc aaggggggcg gggggtctcc cctcggggag  480
gtgccggggg tggccccggc cagcgtggtg atcctcgggg gcgggaccgt gggcaccaac  540
gcggccaaga tcgccctggg gatggggggc caggtgacca tcctgacgt gaaccacaag  600
cgcctccagt atctgacga cgtcttcggc gggcgggtga tcaccctcac cgccaccgag  660
gccaacatca aaagagcgt ccagcacgcg gacctcctca tcgggccgt cctcgtcccc  720
gggccaaggg ccccaagct cgtcaccgg gacatgctct ctctgatgaa ggaggggagc  780
gtgatcgtgg acgtggccgt ggaccagggg ggtgcgtgg agaccatccg cccaccacc  840
cacgccgagc ccacctacgt ggtggacggg gtggtccact acgggtggc caacatgccc  900
ggggcggtgc ccaggaccag cacccttcgcc ctcaccaacc cgaccctgcc ctacgtgttg  960
aagctcgcgg agaaggggct ggacgccctt ctggaggacg cggcccttct caaggggctc  1020
aacacccaca aaggccgcct cacccacccc ggggtggccg aggcctcgg cctgccctac  1080
acgcctcccg aggaggcctt gaggggggtga                                  1110

SEQ ID NO: 32        moltype = DNA   length = 1038
FEATURE              Location/Qualifiers
source               1..1038
                     mol_type = genomic DNA
                     organism = Thermus thermophilus
SEQUENCE: 32
atggagttcg gcgtgcccag agaacggtcg ggcggggaga tcccggaaag gcgggtgccc   60
ctcacgcccc aggggggtgcg ggagctcgtc gcctcggggc accgggtcta cgtggagcgg  120
ggcgtgggga aaggggcggg cttttcccgac gaggcctacg aggaagcggg ggccaggctc  180
gtgggccggg aggaggcctt cggccgcccc caggtggtgc tcaaggtggc ccgcccacc   240
ctcgaggagg tgggctcat gcgcaaaaac gccgttctca tggccttcct ccacctggcg  300
gtggcggaaa gccccctcgt ggaggccatg gcccaaaagg gcctcaccgc catcggctac  360
gagctggtgg gcgaggaggg ccgccgccc gtcctgaagg ccatgagcga gatcgccgag  420
cgcatggccc ccagctcgc cgggcggctc ctcgaggccc ccagggccc gggcatcctc  480
ctctccggcc tggtgggcat ccccccggcc gactggtcg tcctggggc ggggtcctg   540
ggccgggcg cggcgcgggc ctttctgggc gcggggccct cggtccacct cctggaccgg  600
gcccttcccc cgctggagga ggccgccggg gaggccccgg gggccatcac ccctcgtc   660
acccaggacc gctggacgg gtacctggcc ttcgccaagg tcctggtggg ggcggtggcc  720
gtccctgggg agcgcacccc ccttctcctc acccggccc tcctcgcccg catgcgcccc  780
ggaagcgtcc tcctggactt ctccatagac caggggggcg tctcggaaac cagccgcct   840
ggggtctacc aggagatggg cgtcacccac ttctgcctcc caacgtccc cgccctcgtc  900
ccccgcaccg caagccacgc cctcacccctc accctcctcc ctacctgct ccggatccag  960
gaagaccccc tggccttcc cgggctccgc caggggggcct acctcctctt cggcgagaaa 1020
ggaggccacc tagaatga                                                1038

SEQ ID NO: 33        moltype = AA    length = 372
FEATURE              Location/Qualifiers
source               1..372
                     mol_type = protein
                     organism = Geobacillus stearothermophilus
SEQUENCE: 33
MKIGIPKEIK NNENRVAITP AGVMTLVKAG HDVYVETEAG AGSGFSDAEY EKAGAVIVTK   60
AEDAWAAEMV LKVKEPLPEE FRYFRPGLIL FTYLHLAAAE ALTKALVEQK VVGIAYETVQ  120
LANGSLPLLT PMSEVAGRMS VQVGAQFLEK PHGGKILLLG GVPGVRRGKV TIIGGGTAGT  180
NAGKIAVGLG ADVTILDINA ERLRELDDLF GDQVTTLMSN SYHIAECVRE SDLVVGAVLI  240
PGAKAPKLVT EEMVRSMMPG SVLVDVAIDQ GGIFETTDRV TTHDDPTYVK HGVVHYAVAN  300
MPGAVPRTST FALTNVTIPY ALQIANKGYR AACLDNPALL KGINTLDGHI VYEAVAAAHN  360
```

```
MPYTDAHSLL QG                                                        372

SEQ ID NO: 34            moltype = AA  length = 377
FEATURE                  Location/Qualifiers
source                   1..377
                         mol_type = protein
                         organism = Geobacillus stearothermophilus
SEQUENCE: 34
MIIGVPKEIK NNENRVAITP AGVLSFVQAG HTVLIEKEAG VGSGFSDSDY ARAGAQIIER      60
AEDVWAQADM VMKVKEPLPS EYGYFRPGLI LFTYLHLAAD PELTRALKES GVIAIAYETV    120
QVGRTLPLLT PMSEVAGRMA AQIGAQFLEK PYGGKGILLG GVPGVARGKV TIIGGGVVGT    180
NAAKVAVGLG ADVTIIDLNA DRLRELDDIF GNQITTLMSN PMNIAEAVAE ADLVIGAVLI    240
PGARAPKLVT EDMVKAMKPG SVIVDVAIDQ GGIVETSDHV TTHDDPTYVK HGVVHYAVAN    300
MPGAVPRTST IALTNVTMPY ALQIANKGVI QAITDNPALE LGVNVANGEI TYEAVARDLG    360
YRYVPAREAL GKTLAAN                                                   377

SEQ ID NO: 35            moltype = AA  length = 369
FEATURE                  Location/Qualifiers
source                   1..369
                         mol_type = protein
                         organism = Thermus thermophilus
SEQUENCE: 35
MVIGVPKEIK TLENRVALTP GGVESLVRRG HTVLVERGAG EGSGLSDAEY ARAGAELVGR      60
EEAWGAEMVV KVKEPLPEEY GFLREGLILF TYLHLAADRG LTEAMLRSGV TGIAYETVQL    120
PDGTLPLLVP MSEVAGRMAP QVGAQFLEKP KGGRGVLLGG VPGVAPASVV ILGGGTVGTN    180
AAKIALGMGA QVTILDVNHK RLQYLDDVFG GRVITLTATE ANIKKSVQHA DLLIGAVLVP    240
GAKAPKLVTR DMLSLMKEGA VIVDVAVDQG GCVETIRPTT HAEPTYVVDG VVHYGVANMP    300
GAVPRTSTFA LTNQTLPYVL KLAEKGLDAL LEDAALLKGL NTHKGRLTHP GVAEAFGLPY    360
TPPEEALRG                                                            369

SEQ ID NO: 36            moltype = AA  length = 345
FEATURE                  Location/Qualifiers
source                   1..345
                         mol_type = protein
                         organism = Thermus thermophilus
SEQUENCE: 36
MEFGVPRERS GGEIPERRVP LTPQGVRELV ASGHRVYVER GAGEGAGFPD EAYEEAGARL      60
VGREEAFGRP QVVLKVARPT LEEVGLMRKN AVLMAFLHLA VAESPLVEAM AQKGLTAIGY    120
ELVGEEGRRP VLKAMSEIAG RMAPQLAGRL LEAPQGPGIL LSGLVGIPPA DVVVLGAGVL    180
GRAAARAFLG AGASVHLLDR ALPPLEEAAR EAPGAITALV TQDRLERYVA FADVLVGAVA    240
VPGERTPLLL TRGLLARMRP GSVLLDFSID QGGVSETSRP GVYQEMGVTH FCLPNVPALV    300
PRTASHALTL TLLPYLLRIQ EDPLALPGLR QGAYLLFGEK GGHLE                    345

SEQ ID NO: 37            moltype = AA  length = 11
FEATURE                  Location/Qualifiers
REGION                   1..11
                         note = N-terminal portion of maltose-binding protein
source                   1..11
                         mol_type = protein
                         organism = synthetic construct
SEQUENCE: 37
MKIEEGKLVI H                                                          11

SEQ ID NO: 38            moltype = DNA  length = 33
FEATURE                  Location/Qualifiers
misc_feature             1..33
                         note = DNA coding N-terminal portion of maltose-binding
                          protein
source                   1..33
                         mol_type = other DNA
                         organism = synthetic construct
SEQUENCE: 38
atgaaaatcg aagaaggtaa actggtaatc cat                                  33

SEQ ID NO: 39            moltype = AA  length = 388
FEATURE                  Location/Qualifiers
REGION                   1..388
                         note = modified alanine dehydrogenase of Geobacillus
                          stearothermophilus
source                   1..388
                         mol_type = protein
                         organism = synthetic construct
SEQUENCE: 39
MKIEEGKLVI HMIIGVPKEI KNNENRVAIT PAGVLSFVQA GHTVLIEKEA GVGSGFSDSD      60
YARAGAQIIE RAEDVWAQAD MVMKVKEPLP SEYGYFRPGL ILFTYLHLAA DPELTRALKE    120
SGVIAIAYET VQVGRTLPLL TPMSEVAGRM AAQIGAQFLE KPYGGKGILL GGVPGVARGK    180
VTIIGGGVVG TNAAKVAVGL GADVTIIDLN ADRLRELDDI FGNQITTLMS NPMNIAEAVA    240
EADLVIGAVL IPGARAPKLV TEDMVKAMKP GSVIVDVAID QGGIVETSDH VTTHDDPTYV    300
KHGVVHYAVA NMPGAVPRTS TIALTNVTMP YALQIANKGV IQAITDNPAL ELGVNVANGE    360
```

ITYEAVARDL GYRYVPAREA LGKTLAAN                                              388

```
SEQ ID NO: 40            moltype = DNA   length = 1167
FEATURE                  Location/Qualifiers
misc_feature             1..1167
                         note = DNA coding modified alanine dehydrogenase gene of
                          Geobacillus stearothermophilus
source                   1..1167
                         mol_type = other DNA
                         organism = synthetic construct
SEQUENCE: 40
atgaaaatcg aagaaggtaa actggtaatc catatgatta ttggagtgcc aaaggaaatc   60
aaaaataacg aaaaccgtgt cgccattacg ccggctggcg ttttgtcatt cgttcaggct  120
ggacatacgg ttctgattga aaagaggca ggggttggaa gcggttcag gcgacagcgt   180
tacgcccgtg ccggagcaca aatcatcgag cgggcggaag atgtttgggc gcaagccgat  240
atggtgatga agtgaaaga gccgctgcca agcgaatacg gctatttccg cccaggtctc  300
attttgttca cctatttgca tttggccgcc gacccggagt tgacacgcgc cttaaaagaa  360
agcggcgtca tcgccattgc ctatgagacg gtgcaagtcg gccgcacact gccgctgttg  420
acaccaatga gcgaagtcgc cggacggatg gccgcgcaaa ttggagcgca attttttagaa  480
aaaccgtacg gcggcaaagg catcttgctt ggcggcgtcc caggcgttgc ccgcggcaaa  540
gtgacgatca tcggcggcgg agtcgtcggc acgaacgcag cgaaagtcgc ggtcggcctc  600
ggggcagatg tcacgattat cgacttgaac gccgatcggc tcgcgagct tgacgacatt  660
ttcggcaacc aaattacgac gctcatgtcc aacccaatga acatcgccga agcggttgct  720
gaggccgacc ttgtcatcgg cgccgtcctc atcccgggag cgcggcgcc gaagctcgtc  780
accgaggaca tggtgaaagc gatgaaaccg gttcggtca tcgtcgatgt cgccatcgac  840
caagggggca tcgtcgagac gagcgaccac gtcacgacc atgacgaccc gacgtacgcc  900
aaacacggcg tcgtccatta tgcggtcgcc aacatgcctg cgccgtccc gcgcacctca  960
acgatcgcct tgacaacgt caccatgcca tacgccttgc aaatcgccaa caaaggcgtc 1020
atccaagcca ttacagacaa cccggcgctt gagcttggcg tcaacgtcgc caacggtgaa 1080
atcacgtacg aagcggtcgc ccgcgacctc ggttaccgct acgtcccggc ccgcgaagcg 1140
ctcgggaaaa cgttggccgc caactaa                                    1167

SEQ ID NO: 41            moltype = AA   length = 548
FEATURE                  Location/Qualifiers
source                   1..548
                         mol_type = protein
                         organism = Lactococcus lactis
SEQUENCE: 41
MYTVGDYLLD RLHELGIEEI FGVPGDYNLQ FLDQIISRKD MKWVGNANEL NASYMADGYA   60
RTKKAAAFLT TFGVGELSAV NGLAGSYAEN LPVVEIVGSP TSKVQNEGKF VHHTLADGDF  120
KHFMKMHEPV TAARTLLTAE NATVEIDRVL SALLKERKPV YINLPVDVAA AKAEKPSLPL  180
KKENSTSNTS DQEILNKIQE SLKNAKKPIV ITGHEIISFG LEKTVSQFIS KTKLPITTLN  240
FGKSSVDEAL PSFLGIYNGK LSEPNLKEFV ESADFILMLG VKLTDSSTGA FTHHLNENKM  300
ISLNIDEGKI FNESIQNFDF ESLISSLLDL SEIEYKGKYI DKKQEDFVPS NALLSQDRLW  360
QAVENLTQSN ETIVAEQGTS FFGASSIFLK PKSHFIGQPL WGSIGYTFPA ALGSQIADKE  420
SRHLLFIGDG SLQLTVQELG LAIREKINPI CFIINNDGYT VEREIHGPNQ SYNDIPMWNY  480
SKLPESFGAT EERVVSKIVR TENEFVSVMK EAQADPNRMY WIELILAKED APKVLKKMGK  540
LFAEQNKS                                                          548

SEQ ID NO: 42            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 42
cgtggccaac taggcccagc cagatactcc cgatc                              35

SEQ ID NO: 43            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 43
tgaggcctca ttggccggag cgcaacccac tcact                              35

SEQ ID NO: 44            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 44
ctgggcctag ttggccacgt agaaagccag tccgc                              35
```

```
SEQ ID NO: 45            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 45
tccggccaat gaggcctcag aagaactcgt caaga                               35

SEQ ID NO: 46            moltype = DNA   length = 83
FEATURE                  Location/Qualifiers
misc_feature             1..83
                         note = PCR primer
source                   1..83
                         mol_type = other DNA
                         organism = synthetic construct
SEQUENCE: 46
gcattaatcc ttggactcct gttgatagat ccagtaatga cctcagaact ccatctggat    60
ttgttcagaa cgctcggttg ccg                                           83

SEQ ID NO: 47            moltype = DNA   length = 83
FEATURE                  Location/Qualifiers
misc_feature             1..83
                         note = PCR primer
source                   1..83
                         mol_type = other DNA
                         organism = synthetic construct
SEQUENCE: 47
caccgtgcag tcgatggatc tggattctca ccaataaaaa acgcccggcg gcaaccgagc    60
gttctgaaca aatccagatg gag                                           83

SEQ ID NO: 48            moltype = DNA   length = 50
FEATURE                  Location/Qualifiers
misc_feature             1..50
                         note = PCR primer
source                   1..50
                         mol_type = other DNA
                         organism = synthetic construct
SEQUENCE: 48
ttattggtga gaatccagat ccatcgactg cacggtgcac caatgcttct               50

SEQ ID NO: 49            moltype = DNA   length = 70
FEATURE                  Location/Qualifiers
misc_feature             1..70
                         note = PCR primer
source                   1..70
                         mol_type = other DNA
                         organism = synthetic construct
SEQUENCE: 49
gcaagcttgg agtgatcatc gtatgcatat gcgtttctcc tccagatccc tgtttcctgt    60
gtgaaattgt                                                          70

SEQ ID NO: 50            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 50
ctcgaattca ctggccgtcg ttttacaacg tcgtg                               35

SEQ ID NO: 51            moltype = DNA   length = 35
FEATURE                  Location/Qualifiers
misc_feature             1..35
                         note = PCR primer
source                   1..35
                         mol_type = other DNA
                         organism = synthetic construct
SEQUENCE: 51
cgcaattgag tttgtagaaa cgcaaaaagg ccatc                               35

SEQ ID NO: 52            moltype = DNA   length = 35
FEATURE                  Location/Qualifiers
misc_feature             1..35
                         note = PCR primer
source                   1..35
                         mol_type = other DNA
```

```
                        organism = synthetic construct
SEQUENCE: 52
gcacatatgt atacagtagg agattaccta ttaga                                35

SEQ ID NO: 53           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 53
gcaggatcct tatgatttat tttgttcagc aaata                                35

SEQ ID NO: 54           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 54
gcacatatga caaaagcaac aaagaacaa aaatc                                 35

SEQ ID NO: 55           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 55
gcaggatcct agagagcttt cgttttcatg agttc                                35

SEQ ID NO: 56           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 56
cgagtccata tgaaacagac tatccgcaat atcag                                35

SEQ ID NO: 57           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 57
gcaggatcct taccgagaat tcgagcgctt tcgca                                35

SEQ ID NO: 58           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 58
cgagtccata tgaaaaagcg ggtgatgcgt ggcct                                35

SEQ ID NO: 59           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 59
gcaggatcct catctgtctg acagtctcat cgtca                                35

SEQ ID NO: 60           moltype = DNA  length = 35
FEATURE                 Location/Qualifiers
misc_feature            1..35
                        note = PCR primer
source                  1..35
```

```
                            mol_type = other DNA
                            organism = synthetic construct
SEQUENCE: 60
cgagtccata tgcaaccgac ctacactatt gggga                                    35

SEQ ID NO: 61               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 61
cgcggatcct taaacgcggc tgtttcgctc ctcaa                                    35

SEQ ID NO: 62               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 62
cgagtccata tgaaggcagc tgttgttacc cacga                                    35

SEQ ID NO: 63               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 63
cgcgaattct tagctacgca gatcgataac catac                                    35

SEQ ID NO: 64               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 64
cgagtccata tgaaagccgc cgttgttcac aaatt                                    35

SEQ ID NO: 65               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 65
gcaggatcct tacattgtta aaacaatgcg gccat                                    35

SEQ ID NO: 66               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 66
cgagtccata tgaaagcggc agttgtcaac gattt                                    35

SEQ ID NO: 67               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 67
cgcgaattct taacggttga caccgatggt taaaa                                    35

SEQ ID NO: 68               moltype = DNA   length = 35
FEATURE                     Location/Qualifiers
misc_feature                1..35
                            note = PCR primer
```

```
source                      1..35
                            mol_type = other DNA
                            organism = synthetic construct
SEQUENCE: 68
cgagtccata tgaaagcact tacatacccta gggcc                              35

SEQ ID NO: 69               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 69
gcaggatcct taactgttgg aaataatgac tttta                               35

SEQ ID NO: 70               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 70
cgcggtaccg gatctggagg agaaacgcat atgaa                               35

SEQ ID NO: 71               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 71
cgcggtacct taacggttga caccgatggt taaaa                               35

SEQ ID NO: 72               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 72
gcacatatga cttatactgt cggacattat cttgc                               35

SEQ ID NO: 73               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 73
gcaggatcct tagacgctct ggggcttgcg ggagt                               35

SEQ ID NO: 74               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 74
cgagtccata tgaaggcagc tgttgttacc cacga                               35

SEQ ID NO: 75               moltype = DNA   length = 35
FEATURE                     Location/Qualifiers
misc_feature                1..35
                            note = PCR primer
source                      1..35
                            mol_type = other DNA
                            organism = synthetic construct
SEQUENCE: 75
cgcgtcgact tagctacgca gatcgataac catac                               35

SEQ ID NO: 76               moltype = DNA   length = 35
FEATURE                     Location/Qualifiers
misc_feature                1..35
```

```
                    note = PCR primer
source              1..35
                    mol_type = other DNA
                    organism = synthetic construct
SEQUENCE: 76
gcacatatgt ataccgttgg tatgtacttg gcaga                               35

SEQ ID NO: 77       moltype = DNA  length = 35
FEATURE             Location/Qualifiers
misc_feature        1..35
                    note = PCR primer
source              1..35
                    mol_type = other DNA
                    organism = synthetic construct
SEQUENCE: 77
gcagtcgact tacgcttgtg gtttgcgaga gttgg                               35

SEQ ID NO: 78       moltype = DNA  length = 35
FEATURE             Location/Qualifiers
misc_feature        1..35
                    note = PCR primer
source              1..35
                    mol_type = other DNA
                    organism = synthetic construct
SEQUENCE: 78
gcacatatga catatacagt cggcatgtat cttgc                               35

SEQ ID NO: 79       moltype = DNA  length = 35
FEATURE             Location/Qualifiers
misc_feature        1..35
                    note = PCR primer
source              1..35
                    mol_type = other DNA
                    organism = synthetic construct
SEQUENCE: 79
gcagtcgact caggatacct gcggttttct ggaat                               35

SEQ ID NO: 80       moltype = DNA  length = 35
FEATURE             Location/Qualifiers
misc_feature        1..35
                    note = PCR primer
source              1..35
                    mol_type = other DNA
                    organism = synthetic construct
SEQUENCE: 80
gcacatatgg ctgttactaa tgtcgctgaa cttaa                               35

SEQ ID NO: 81       moltype = DNA  length = 35
FEATURE             Location/Qualifiers
misc_feature        1..35
                    note = PCR primer
source              1..35
                    mol_type = other DNA
                    organism = synthetic construct
SEQUENCE: 81
gcaggatcct taagcggatt ttttcgcttt tttct                               35

SEQ ID NO: 82       moltype = DNA  length = 35
FEATURE             Location/Qualifiers
misc_feature        1..35
                    note = PCR primer
source              1..35
                    mol_type = other DNA
                    organism = synthetic construct
SEQUENCE: 82
gcacatatga cgaaaatagc gaataaatac gaagt                               35

SEQ ID NO: 83       moltype = DNA  length = 35
FEATURE             Location/Qualifiers
misc_feature        1..35
                    note = PCR primer
source              1..35
                    mol_type = other DNA
                    organism = synthetic construct
SEQUENCE: 83
gcactgcagt tatttcttcg cacctccgta ataag                               35

SEQ ID NO: 84       moltype = DNA  length = 35
FEATURE             Location/Qualifiers
```

```
misc_feature            1..35
                        note = PCR primer
source                  1..35
                        mol_type = other DNA
                        organism = synthetic construct
SEQUENCE: 84
gaagctggcg ctgcgcttta tggatatccg taaac                              35

SEQ ID NO: 85           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 85
tcgaagtgag tttccggatg ttcgtacata accca                              35

SEQ ID NO: 86           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 86
atggcaatga gatttatgga tataagaaag agagt                              35

SEQ ID NO: 87           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 87
gttcataaag tcaacttccg gatgttcata catca                              35

SEQ ID NO: 88           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 88
cgcggtaccg gatctggagg agaaacgcat atgaa                              35

SEQ ID NO: 89           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 89
cgcggtacct taacggttga caccgatggt taaaa                              35

SEQ ID NO: 90           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 90
tccggcgggc atatgaagat cggcattcca aaaga                              35

SEQ ID NO: 91           moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 91
aagaattcca gcggctcata tacgataccg ttcgg                              35

SEQ ID NO: 92           moltype = DNA  length = 35
```

```
FEATURE                 Location/Qualifiers
misc_feature            1..35
                        note = PCR primer
source                  1..35
                        mol_type = other DNA
                        organism = synthetic construct
SEQUENCE: 92
tccggcgggc atatgattat tggagtgcca aagga                          35

SEQ ID NO: 93           moltype = DNA   length = 35
FEATURE                 Location/Qualifiers
misc_feature            1..35
                        note = PCR primer
source                  1..35
                        mol_type = other DNA
                        organism = synthetic construct
SEQUENCE: 93
aagaattctt agttggcagc caacgttttc ccgag                          35

SEQ ID NO: 94           moltype = DNA   length = 35
FEATURE                 Location/Qualifiers
misc_feature            1..35
                        note = PCR primer
source                  1..35
                        mol_type = other DNA
                        organism = synthetic construct
SEQUENCE: 94
ccggcgggca tatggtgatc ggcgtgccga aggag                          35

SEQ ID NO: 95           moltype = DNA   length = 35
FEATURE                 Location/Qualifiers
misc_feature            1..35
                        note = PCR primer
source                  1..35
                        mol_type = other DNA
                        organism = synthetic construct
SEQUENCE: 95
aagaattctc accccctcaa ggcctcctcg ggagg                          35

SEQ ID NO: 96           moltype = DNA   length = 35
FEATURE                 Location/Qualifiers
misc_feature            1..35
                        note = PCR primer
source                  1..35
                        mol_type = other DNA
                        organism = synthetic construct
SEQUENCE: 96
cggcgggcat atggagttcg gcgtgcccag agaac                          35

SEQ ID NO: 97           moltype = DNA   length = 35
FEATURE                 Location/Qualifiers
misc_feature            1..35
                        note = PCR primer
source                  1..35
                        mol_type = other DNA
                        organism = synthetic construct
SEQUENCE: 97
aagaattctc attctaggtg gcctcctttc tcgcc                          35

SEQ ID NO: 98           moltype = DNA   length = 33
FEATURE                 Location/Qualifiers
misc_feature            1..33
                        note = PCR primer
source                  1..33
                        mol_type = other DNA
                        organism = synthetic construct
SEQUENCE: 98
tatgaaaatc gaagaaggta aactggtaat cca                            33

SEQ ID NO: 99           moltype = DNA   length = 33
FEATURE                 Location/Qualifiers
misc_feature            1..33
                        note = PCR primer
source                  1..33
                        mol_type = other DNA
                        organism = synthetic construct
SEQUENCE: 99
tatggattac cagtttacct tcttcgattt tca                            33
```

```
SEQ ID NO: 100          moltype = AA   length = 6
FEATURE                 Location/Qualifiers
REGION                  1..6
                        note = Polypeptide written by Journal of Bioscience and
                        Bioengineering, 123, 540-546 (2017)
source                  1..6
                        mol_type = protein
                        organism = synthetic construct
SEQUENCE: 100
MSKIKH                                                                        6

SEQ ID NO: 101          moltype = DNA   length = 18
FEATURE                 Location/Qualifiers
misc_feature            1..18
                        note = PCR primer
source                  1..18
                        mol_type = other DNA
                        organism = synthetic construct
SEQUENCE: 101
tatgagcaag atcaaaca                                                          18

SEQ ID NO: 102          moltype = DNA   length = 18
FEATURE                 Location/Qualifiers
misc_feature            1..18
                        note = PCR primer
source                  1..18
                        mol_type = other DNA
                        organism = synthetic construct
SEQUENCE: 102
tatgtttgat cttgctca                                                          18

SEQ ID NO: 103          moltype = AA   length = 11
FEATURE                 Location/Qualifiers
REGION                  1..11
                        note = N-terminal portion of glutathione S-transferase
source                  1..11
                        mol_type = protein
                        organism = synthetic construct
SEQUENCE: 103
MDFPVAEDRR H                                                                 11

SEQ ID NO: 104          moltype = DNA   length = 33
FEATURE                 Location/Qualifiers
misc_feature            1..33
                        note = PCR primer
source                  1..33
                        mol_type = other DNA
                        organism = synthetic construct
SEQUENCE: 104
tatgtcgccg atcctcggct actggaaaat cca                                         33

SEQ ID NO: 105          moltype = DNA   length = 33
FEATURE                 Location/Qualifiers
misc_feature            1..33
                        note = PCR primer
source                  1..33
                        mol_type = other DNA
                        organism = synthetic construct
SEQUENCE: 105
tatggatttt ccagtagccg aggatcggcg aca                                         33

SEQ ID NO: 106          moltype = AA   length = 11
FEATURE                 Location/Qualifiers
REGION                  1..11
                        note = N-terminal portion of beta-glucosidase
source                  1..11
                        mol_type = protein
                        organism = synthetic construct
SEQUENCE: 106
MTENAEKFLW H                                                                 11

SEQ ID NO: 107          moltype = DNA   length = 33
FEATURE                 Location/Qualifiers
misc_feature            1..33
                        note = PCR primer
source                  1..33
                        mol_type = other DNA
                        organism = synthetic construct
SEQUENCE: 107
```

```
tatgaccgag aacgccgaaa aattcctttg gca                                33

SEQ ID NO: 108       moltype = DNA  length = 33
FEATURE              Location/Qualifiers
misc_feature         1..33
                     note = PCR primer
source               1..33
                     mol_type = other DNA
                     organism = synthetic construct
SEQUENCE: 108
tatgccaaag gaatttttcg gcgttctcgg tca                                33

SEQ ID NO: 109       moltype = AA  length = 22
FEATURE              Location/Qualifiers
REGION               1..22
                     note = HAT sequence
source               1..22
                     mol_type = protein
                     organism = synthetic construct
SEQUENCE: 109
MGKDHLIHNV HKEEHAHAHN KH                                            22

SEQ ID NO: 110       moltype = DNA  length = 45
FEATURE              Location/Qualifiers
misc_feature         1..45
                     note = PCR primer
source               1..45
                     mol_type = other DNA
                     organism = synthetic construct
SEQUENCE: 110
cgcatatggg caaggatcat ctcatccaca atgtccacaa agagg                   45

SEQ ID NO: 111       moltype = DNA  length = 45
FEATURE              Location/Qualifiers
misc_feature         1..45
                     note = PCR primer
source               1..45
                     mol_type = other DNA
                     organism = synthetic construct
SEQUENCE: 111
cgcatatgct tgttgtgggc atgagcgtgc tcctctttgt ggaca                   45
```

GENUS HYDROGENOPHILUS BACTERIUM TRANSFORMANT

SEQUENCE LISTING SUBMISSION VIA EFS-WEB

The contents of the electronic sequence listing (128209-5001-US-02_Sequence_Listing.xml; Size: 176,142 bytes; and Date of Creation: May 9, 2023) is herein incorporated by reference in its entirety.

TECHNICAL FIELD

The present invention relates to a genus *Hydrogenophilus* bacterium transformant having an ability to produce isobutanol, ethanol, or alanine, and to a method for producing isobutanol, ethanol, or alanine using the same.

BACKGROUND ART

Production of Chemical Products Using Microorganisms

Paris Agreement that was adopted in 2015, provides that global emissions of greenhouse gas should be promptly reduced. Under the Paris Agreement, Japan has set a goal of reducing emissions of greenhouse gas such as carbon dioxide and methane by 26% by the year 2030, in comparison with those of the year 2013.

Worldwide, majority of the production of chemical products depends on petroleum sources, and there is the problem of increase in greenhouse gas emissions. Accordingly, departure from petroleum dependency is required in the production of chemical products, and research and development of biorefineries that produce green chemical products from biomass is being strenuously carried out in various countries. However, the conversion of biomass into saccharides to be used as raw materials of microbial fermentation requires complex processes, and there is an issue of high cost.

As part of a research to depart from petroleum dependency, gases such as carbon dioxide, methane, and carbon monoxide have attracted attention as carbon sources having a higher degree of sustainability, and techniques for producing valuable chemical products and biofuels using microorganisms that utilize these gases are being a subject of interest. In particular, fixation and effective utilization of carbon dioxide, which is known for its high contribution to warming, is highly anticipated.

Production of Isobutanol

Ethanol, n-butanol, and isobutanol have been used conventionally as biofuels, and methods for efficiently producing the compounds have been required. Some merits of butanol, which has 4 carbon atoms, are that it has a higher fuel efficiency as compared to that of ethanol having 2 carbon atoms, that it can be easily mixed with gasoline (carbon atoms 4 to 10) or diesel engines enabling the use of existing engines and fueling facilities as they are, and that facilities are less likely to corrode since butanol absorbs only a small amount of water in the air. In particular, there is a certified ASTM standard for isobutanol as a raw material of drop-in type biojet fuel. Technical development for practical application of isobutanol has been conducted as an effort to reduce carbon dioxide emission in the field of aviation.

Yeast and some bacteria produce a small amount of isobutanol. Isobutanol is produced from 2-ketoisovalerate, which is a metabolic intermediate in the biosynthetic pathway of essential amino acid valine. Isobutanol is produced via 5 steps from pyruvic acid, which is an important metabolite in a living body. Namely, acetolactate is produced from pyruvic acid by the catalytic action of acetohydroxy acid synthase, then 2,3-dihydroxyisovalerate is produced from acetolactate by the catalytic action of acetohydroxy acid isomeroreductase, then 2-ketoisovalerate is produced from 2,3-dihydroxyisovalerate by the catalytic action of dihydroxy acid dehydratase, then isobutyraldehyde is produced from 2-ketoisovalerate by the catalytic action of 2-keto-acid decarboxylase (hereinafter, may be referred to as "KDC") (EC 4.1.1.1), and finally, isobutanol is produced from isobutyraldehyde by the catalytic action of alcohol dehydrogenase (hereinafter, may be referred to as "ADH") (EC 1.1.1.1).

As a technique for producing isobutanol using a recombinant microorganism, Patent Document 1 discloses a method for producing isobutanol using a *Corynebacterium glutamicum* transformant. The transformat has exogenous genes of the above-described 5 enzymes that respectively catalyze the 5 steps that compose the metabolic pathway from pyruvic acid to isobutanol. *Lactococcus lactis* kivD gene or *Staphylococcus epidermidis* ipd gene is used as a 2-keto-acid decarboxylase gene, and *Saccharomyces cerevisiae* adh2 gene, *Pseudomonas putida* adh gene, or *Escherichia coli* adhP gene is used as an alcohol dehydrogenase gene.

In addition, various methods are known for producing isobutanol using transformants into which only a 2-keto-acid decarboxylase gene and an alcohol dehydrogenase gene are introduced.

Non-patent Document 1 teaches the use of a transformant obtained by introducing *Lactococcus lactis* kivD gene and *Saccharomyces cerevisiae* adh2 gene into *Escherichia coli*.

Non-patent Document 2 teaches the use of a transformant obtained by introducing *Lactococcus lactis* kivD gene and *Lactococcus lactis* adhA gene into *Escherichia coli*.

Non-patent Document 3 teaches the use of a transformant obtained by introducing *Lactococcus lactis* kivD gene and *Saccharomyces cerevisiae* adh2 gene into *Bacillus subtilis*.

Non-patent Document 4 teaches the use of a transformant obtained by introducing *Lactococcus lactis* kivD gene and *Ralstonia eutropha* adh gene into *Shewanella oneidensis*.

Non-patent Document 5 teaches the use of a transformant obtained by introducing *Lactococcus lactis* kivD gene and *Escherichia coli* yqhD gene into the cyanobacterium *Synechococcus elongatus*.

Non-patent Document 6 teaches the use of a transformant obtained by introducing a plasmid for overexpressing *Lactococcus lactis* kivD gene and *Ralstonia eutropha* adh gene into *Ralstonia eutropha*.

Non-patent Document 7 teaches the use of a transformant obtained by introducing a plasmid for overexpressing *Lactococcus lactis* kivD gene and *Geobacillus thermoglucosidasius* adhA gene into *Geobacillus thermoglucosidasius*.

Methods are also known in which, *Bacillus subtilis* alsS gene, *Geobacillus thermoglucosidasius* Geoth_3495 gene, *Geobacillus thermodenitrificans* Gtng_0348 gene, *Klebsiella pneumoniae* ipdC gene, or *Staphylococcus epidermidis* ipd gene is used as a 2-keto-acid decarboxylase gene besides a method in which *Lactococcus lactis* kivD gene is used. However, *Lactococcus lactis* kivD gene generally brings about higher enzyme activity within the host than the former 5 genes, and therefore, *Lactococcus lactis* kivD gene has been mainly used conventionally.

Almost all of the above-described methods are methods for producing isobutanol using sugar as a carbon source, and not methods for producing isobutanol using carbon dioxide as a carbon source.

The method of Non-patent Document 5 uses Cyanobacterium, which is a photosynthetic bacterium, as a host. The method is for producing isobutanol using sodium hydrogen carbonate as a carbon source. Cyanobacteria have a higher carbon dioxide fixation ability as compared to that of plants. However, the method of using Cyanobacterium as a host has not been put into practical use as an industrial method for producing isobutanol since carbon dioxide fixation ability of Cyanobacteria is insufficient.

Production of Ethanol

Conventionally, much of the ethanol used for fuels, chemical raw materials, beverages, and the like, has been manufactured by fermenting starch or saccharides derived from various biomass resources using microorganisms.

As methods for producing ethanol using a recombinant microorganism, methods which use transformants obtained by introducing a gene of pyruvate decarboxylase (hereinafter may be referred to as "PDC") (EC 4.1.1.1), which catalyzes the reaction of producing acetaldehyde by decarboxylating pyruvic acid, and/or introducing a gene of alcohol dehydrogenase (hereinafter may be referred to as "ADH") (EC 1.1.1.1), which catalyzes the reaction from acetaldehyde to ethanol, are known.

Many of the conventional methods use a transformant obtained by introducing a gene that produces PDC and a gene that produces ADH, both derived from *Zymomonas mobilis*. For example, Patent Document 2 teaches that a transformant obtained by introducing pdc gene and adhB gene, both derived from *Zymomonas mobilis*, into an enteric bacterium such as *Escherichia coli*, produces ethanol efficiently.

As a method that utilizes PDC and ADH genes of other bacteria, Non-patent Document 8 discloses a method for producing ethanol using a transformant obtained by introducing *Sarcina ventriculi* pdc gene and *Lactobacillus brevis* adh gene into *Escherichia coli*.

In addition, Non-patent Document 9 discloses a method for producing ethanol using a transformant obtained by introducing *Sarcina ventriculi* pdc gene and *Geobacillus stearothermophilus* adh gene into *Bacillus megaterium*.

Other than the pyruvate decarboxylase genes described above, pyruvate decarboxylase genes of *Gluconobacter oxydans*, *Gluconoacetobacter diazotrophicus*, *Acetobacter pasteurianus*, *Clostridium acetobutylicum*, and *Zymobacter palmae* are known to be utilized. Furthermore, other than the alcohol dehydrogenase genes described above, alcohol dehydrogenase genes of various microbial species are known to be utilized.

However, the methods described in those literatures are methods for producing ethanol using sugar as a carbon source, and not a method for producing ethanol using carbon dioxide as a carbon source.

As methods for producing ethanol using carbon dioxide as a carbon source, methods in which cyanobacterium, a photosynthetic bacterium, is used as a host, are known. For example, Non-patent Document 10 discloses a method for producing ethanol using a transformant obtained by introducing pdc and adhB genes derived from *Zymomonas mobilis* into a bacterium of the genus *Synechococcus*.

In addition, Non-patent Document 11 discloses a method for producing ethanol using a transformant obtained by introducing *Zymomonas mobilis* pdc gene and the NADPH-dependent ADH gene (slr1192) of bacteria of the genus *Synechocystis*, into a bacterium of the genus *Synechococcus*.

As mentioned above, the carbon dioxide fixation ability of Cyanobacteria is insufficient for industrial utilization, and therefore, no methods for using Cyanobacterium as a host has been put into practical use as a method for industrial production of ethanol.

Furthermore, as methods for producing ethanol using a recombinant microorganism, methods using transformants obtained by introducing a gene of aldehyde-alcohol dehydrogenase, which catalyzes the reaction of producing ethanol from acetyl-CoA via acetaldehyde, are also known.

The reaction of producing ethanol from acetyl-CoA via acetaldehyde is important for ethanol production under anaerobic conditions, and thus the aldehyde-alcohol dehydrogenase gene is generally used when producing alcohol using a microorganism that grows under anaerobic conditions, as a host.

For example, Non-patent Document 12 teaches a method for producing ethanol using a transformant obtained by introducing adhE gene, which is an aldehyde-alcohol dehydrogenase gene, into *Pyrococcus furiosus*, which grows under anaerobic conditions.

In addition, Non-patent Document 13 teaches a method for producing ethanol using a transformant obtained by introducing adhE gene into *Caldicellulosiruptor bescii*, which grows under anaerobic conditions.

However, these methods described in those literatures are methods for producing ethanol using sugar as a carbon source, and not a method for producing ethanol using carbon dioxide as a carbon source.

Production of Alanine

Alanine is an amino acid that is important as a raw material for medicine, food, or in chemical industry, and there is an increasing demand for alanine. Alanine dehydrogenase (EC 1.4.1.1) has been utilized for the production of alanine. This enzyme catalyzes the reaction of producing alanine from pyruvic acid, ammonia, and NADH.

As a technique to produce alanine using a microorganism, Non-patent Document 14 teaches a method for producing alanine using a transformant obtained by introducing the alanine dehydrogenase gene of *Bacillus stearothermophilus* (currently referred to as *Geobacillus stearothermophilus*) into *Escherichia coli*.

Patent Document 3 teaches a method for producing alanine using a transformant obtained by introducing the alanine dehydrogenase gene of bacteria of the genus *Arthrobacter*, into a bacterium of the genus *Escherichia*, genus *Corynebacterium*, or genus *Brevibacterium*.

Non-patent Document 15 teaches a method for producing alanine using a transformant obtained by introducing the alanine dehydrogenase gene of *Bacillus sphaericus* (currently referred to as *Lysinibacillus sphaericus*) into *Escherichia coli*.

Non-patent Document 16 teaches a method for producing alanine using a transformant obtained by introducing the alanine dehydrogenase gene of *Bacillus sphaericus* (currently referred to as *Lysinibacillus sphaericus*) into *Zymomonas mobilis*.

Non-patent Document 17 teaches a method for producing alanine using a transformant obtained by introducing the alanine dehydrogenase gene of *Bacillus sphaericus* (currently referred to as *Lysinibacillus sphaericus*) into *Lactococcus lactis*.

Non-patent Document 18 teaches a method for producing alanine using a transformant obtained by introducing the alanine dehydrogenase gene of *Bacillus sphaericus* (currently referred to as *Lysinibacillus sphaericus*) into *Corynebacterium glutamicum*.

However, all of the above-described methods are methods for producing alanine using sugar as a carbon source, and not methods for producing alanine using carbon dioxide as a carbon source.

CITATION LIST

Patent Documents

[Patent Document 1] WO/2010/113832
[Patent Document 2] WO/2001/96573
[Patent Document 3] JP1994(Heisei 6)-277082A Non-Patent Documents

[Non-patent Document 1] Non-fermentative pathways for synthesis of branched-chain higher alcohols as biofuels. Atsumi S, Hanai T, Liao J C. Nature (2008) 451:86-89

[Non-patent Document 2] Engineering the isobutanol biosynthetic pathway in *Escherichia coli* by comparison of three aldehyde reductase/alcohol dehydrogenase genes. Atsumi S, Wu T Y, Eckl E M, Hawkins S D, Buelter T, Liao J C. Appl. Microbiol. Biotechnol. (2010) 85:651-657

[Non-patent Document 3] Engineering *Bacillus subtilis* for isobutanol production by heterologous Ehrlich pathway construction and the biosynthetic 2-ketoisovalerate precursor pathway overexpression. Li S, Wen J, Jia X. Appl. Microbiol. Biotechnol. (2011) 91:577-589

[Non-patent Document 4] Isobutanol production from an engineered *Shewanella oneidensis* MR-1. Jeon J M, Park H, Seo H M, Kim J H, Bhatia S K, Sathiyanarayanan G, Song H S, Park S H, Choi K Y, Sang B I, Yang Y H. Bioprocess Biosyst. Eng. (2015) 38:2147-2154

[Non-patent Document 5] Direct photosynthetic recycling of carbon dioxide to isobutyraldehyde. Atsumi S, Higashide W, Liao J C. Nat. Biotechnol. (2009) 27:1177-1180

[Non-patent Document 6] Studies on the production of branched-chain alcohols in engineered *Ralstonia eutropha*. Lu J, Brigham C J, Gai C S, Sinskey A J. Appl. Microbiol. Biotechnol. (2012) 96:283-297

[Non-patent Document 7] Isobutanol production at elevated temperatures in thermophilic *Geobacillus thermoglucosidasius*. Lin P P, Rabe K S, Takasumi J L, Kadisch M, Arnold F H, Liao J C. Metab. Eng. (2014) 24:1-8

[Non-patent Document 8] Coexpression of pyruvate decarboxylase and alcohol dehydrogenase genes in *Lactobacillus brevis*. Liu S, Dien B S, Nichols N N, Bischoff K M, Hughes S R, Cotta M A. FEMS Microbiol. Lett. (2007) 274:291-297

[Non-patent Document 9] Construction and expression of an ethanol production operon in Gram-positive bacteria. Talarico L A, Gil M A, Yomano L P, Ingram L O, Maupin-Furlow J A. Microbiology (2005) 151:4023-4031

[Non-patent Document 10] Ethanol synthesis by genetic engineering in cyanobacteria. Deng M D, Coleman J R. Appl. Environ. Microbiol. (1999) 65:523-528

[Non-patent Document 11] Combinatory strategy for characterizing and understanding the ethanol synthesis pathway in cyanobacteria cell factories. Luan G, Qi Y, Wang M, Li Z, Duan Y, Tan X, Lu X, Biotechnol. Biofuels (2015) 8:184

[Non-patent Document 12] Ethanol production by the hyperthermophilic archaeon *Pyrococcus furiosus* by expression of bacterial bifunctional alcohol dehydrogenases. Keller M W, Lipscomb G L, Nguyen D M, Crowley A T, Schut G J, Scott I, Kelly R M, Adams M W W. Microb. Biotechnol. (2017) 10:1535-1545

[Non-patent Document 13] Cellulosic ethanol production via consolidated bioprocessing at 75° C. by engineered *Caldicellulosiruptor bescii*. Chung D, Cha M, Snyder E N, Elkins J G, Guss A M, Westpheling J. Biotechnol. Biofuels (2015) 8:163

[Non-patent Document 14] Alanine production in an H+-ATPase- and lactate dehydrogenase-defective mutant of *Escherichia coli* expressing alanine dehydrogenase. Wada M, Narita K, Yokota A. Appl. Microbiol. Biotechnol. (2007) 76:819-825

[Non-patent Document 15] Aerobic production of alanine by *Escherichia coli* aceF ldhA mutants expressing the *Bacillus sphaericus* alaD gene. Lee M, Smith G M, Eiteman M A, Altman E. Appl. Microbiol. Biotechnol. (2004) 65:56-60

[Non-patent Document 16] Expression of an L-alanine dehydrogenase gene in *Zymomonas mobilis* and excretion of L-alanine. Uhlenbusch I, Sahm H, Sprenger G A. Appl. Environ. Microbiol. (1991) 57:1360-1366

[Non-patent Document 17] Conversion of *Lactococcus lactis* from homolactic to homoalanine fermentation through metabolic engineering. Hols P, Kleerebezem M, Schanck A N, Ferain T, Hugenholtz J, Delcour J, de Vos W M. Nat. Biotechnol. (1999) 17:588-592

[Non-patent Document 18] Engineering of sugar metabolism of *Corynebacterium glutamicum* for production of amino acid L-alanine under oxygen deprivation. Jojima T, Fujii M, Mori E, Inui M, Yukawa H. Appl. Microbiol. Biotechnol. (2010) 87:159-165

SUMMARY OF INVENTION

Technical Problem

The first object of the present invention is to provide a transformant of a bacterium of the genus *Hydrogenophilus* that is capable of efficiently producing isobutanol utilizing carbon dioxide as a sole carbon source, a method for efficiently producing isobutanol using this transformant, and a gene that enables the highly efficient production of isobutanol by bacteria of the genus *Hydrogenophilus*.

The second object of the present invention is to provide a transformant of a bacterium of the genus *Hydrogenophilus* that is capable of efficiently producing ethanol utilizing carbon dioxide as a sole carbon source, and a method for efficiently producing ethanol using this transformant.

The third object of the present invention is to provide a transformant of a bacterium of the genus *Hydrogenophilus* that is capable of efficiently producing alanine utilizing carbon dioxide as a sole carbon source, a method for efficiently producing alanine using this transformant, and a gene that enables highly efficient production of alanine by bacteria of the genus *Hydrogenophilus*.

Solution to Problem

The inventors of the present invention have carried out intensive studies in order to achieve the objects described above and have found the followings.

Compatibility Between Host and Gene

Bacteria of the genus *Hydrogenophilus* are hydrogen oxidizing bacteria which grow by producing organic substances from carbon dioxide by utilizing hydrogen energy. The growth rate of hydrogen oxidizing bacteria is generally extremely slow, however, the growth rate of bacteria of the genus *Hydrogenophilus* is fast, and their carbon dioxide fixation ability is remarkably higher than that of plants and photosynthetic bacteria. Bacteria of the genus *Hydrogenophilus* do not originally produce isobutanol or ethanol, and therefore, there is a need to introduce gene(s) of enzyme(s) that catalyze(s) the reaction of producing these compounds in order to provide the bacteria with the ability to produce these compounds. In addition, bacteria of the genus *Hydrogenophilus* produce alanine, however, in order to provide them with an ability to produce alanine at an industrial scale, there is a need to introduce gene(s) of enzyme(s) that catalyze(s) the reaction of producing alanine.

However, when a heterologous gene having natural base sequence is introduced into bacteria of the genus *Hydrogenophilus* using a vector that functions within the bacteria, a functioning protein often is not produced or insufficiently produced.

Production of Isobutanol (i) Bacteria of genus *Hydrogenophilus* originally do not produce isobutanol, and do not have a 2-keto-acid decarboxylase gene. Even when *Lactococcus lactis* kivD gene, *Bacillus subtilis* alsS gene, *Geobacillus thermoglucosidasius* Geoth_3495 gene, *Geobacillus thermodenitrificans* Gtng_0348 gene, or *Klebsiella pneumoniae* ipdC gene is introduced into bacteria of the genus *Hydrogenophilus* as a 2-keto-acid decarboxylase gene, they do not function within the genus *Hydrogenophilus* bacteria. In particular, *Lactococcus lactis* kivD gene functions and brings about high activity within various hosts, and thus is frequently used in methods for producing isobutanol, however, it does not function within bacteria of the genus *Hydrogenophilus*. Thus, when a heterologous gene is introduced into bacteria of the genus *Hydrogenophilus* using a vector that functions within the bacteria, a functioning protein often is not produced or insufficiently produced.

With regard to this point, the inventors of the present invention have accumulated data on whether or not genes derived from various microorganisms are expressed in bacteria of the genus *Hydrogenophilus*. By further advancing this accumulation of information and systematizing it, the codon usage of *Lactococcus lactis* kivD gene was optimized so that it was conformed to the frequency of codon usage of bacteria of the genus *Hydrogenophilus*. As a result, the inventors of the present invention have succeeded in producing a highly active 2-keto-acid decarboxylase by introducing the codon-optimized kivD gene which consists of a base sequence of SEQ ID NO: 1 into bacteria of the genus *Hydrogenophilus*.

(ii) Bacteria of the genus *Hydrogenophilus* originally do not produce isobutanol, and do not have an alcohol dehydrogenase gene.

However, when an alcohol dehydrogenase gene of a heterogenous microorganism is introduced into bacteria of the genus *Hydrogenophilus*, the gene functions in the genus *Hydrogenophilus* bacteria and a highly active alcohol dehydrogenase is produced. In particular, when *Klebsiella pneumoniae* adhP gene, *Geobacillus thermocatenulatus* adhP gene, or *Geobacillus thermoglucosidasius* adhA or adhP gene is introduced into bacteria of the genus *Hydrogenophilus*, a particularly highly active alcohol dehydrogenase is produced.

(iii) A transformant obtained by introducing the codon-optimized 2-keto-acid decarboxylase gene described in (i) above, and an alcohol dehydrogenase gene into a bacterium of the genus *Hydrogenophilus*, efficiently produces isobutanol using carbon dioxide as a sole carbon source.

Production of Ethanol

First Transformant Having Ethanol Producing Ability (i) Bacteria of the genus *Hydrogenophilus* originally do not produce ethanol, and do not have a pyruvate decarboxylase gene. Even when the pdc gene of *Zymomonas mobilis, Zymobacter palmae* or *Acetobacter pasteurianus*, which has been reported to produce ethanol, is introduced into bacteria of the genus *Hydrogenophilus* as a pyruvate decarboxylase gene, the gene does not function within the genus *Hydrogenophilus* bacteria.

On the other hand, *Gluconobacter oxydans* pdc gene functions within bacteria of the genus *Hydrogenophilus*, and a highly active pyruvate decarboxylase is produced.

(ii) Bacteria of the genus *Hydrogenophilus* do not originally produce ethanol, and do not have an alcohol dehydrogenase gene.

However, when an alcohol dehydrogenase gene of a heterogenous microorganism is introduced into bacteria of the genus *Hydrogenophilus*, the gene functions within the genus *Hydrogenophilus* bacteria, and a highly active alcohol dehydrogenase is produced. In particular, when *Klebsiella pneumoniae* adhP gene, *Geobacillus thermocatenulatus* adhP gene, or *Geobacillus thermoglucosidasius* adhA or adhP gene, is introduced into bacteria of the genus *Hydrogenophilus*, an especially highly active alcohol dehydrogenase is produced.

(iii) A transformant obtained by introducing *Gluconobacter oxydans* pdc gene, and an alcohol dehydrogenase gene into a bacterium of the genus *Hydrogenophilus* efficiently produces ethanol using carbon dioxide as a sole carbon source.

Second Transformant Having Ethanol Producing Ability (i) Bacteria of the genus *Hydrogenophilus* originally do not produce ethanol, and do not have an aldehyde-alcohol dehydrogenase gene.

However, by introducing an aldehyde-alcohol dehydrogenase gene of a heterogenous microorganism into bacteria of the genus *Hydrogenophilus*, the gene functions within the genus *Hydrogenophilus* bacteria, and a highly active aldehyde-alcohol dehydrogenase is produced. In particular, when adhE gene of *Escherichia coli* or *Clostridium thermocellum* is introduced into bacteria of the genus *Hydrogenophilus*, an especially highly active aldehyde-alcohol dehydrogenase is produced. As a result, the obtained transformant produces ethanol efficiently.

(ii) The activity of aldehyde-alcohol dehydrogenase is inhibited under aerobic conditions. However, a mutant aldehyde-alcohol dehydrogenase in which Glu at position 568 of the aldehyde-alcohol dehydrogenase of *Escherichia coli* has been substituted by Lys, Ala, Leu, Asn, Gly, Ser, Arg, or His, and a mutant aldehyde-alcohol dehydrogenase in which Asp at position 575 of the aldehyde-alcohol dehydrogenase of *Clostridium thermocellum* has been substituted by Asn, show activity under aerobic conditions. Bacteria of the genus *Hydrogenophilus* into which each of the mutant adhE genes of adhE(E568K, E568A, E568L, E568N, E568G, E568S, E568R, and E568H) and adhE(D575N), encoding the above mutant aldehyde-alcohol dehydrogenases, have been introduced, respectively, produce highly active aldehyde-alcohol dehydrogenases under aerobic conditions.

Bacteria of the genus *Hydrogenophilus* cannot grow under anaerobic conditions, and thus the production of substances using bacteria of the genus *Hydrogenophilus* need to be performed under aerobic conditions. In this respect, the transformants of bacteria of the genus *Hydrog-*

*enophilus* obtained by introducing these mutant adhE genes can still more efficiently produce ethanol under aerobic conditions, using carbon dioxide as a sole carbon source.

Production of Alanine
- (i) Bacteria of the genus *Hydrogenophilus* produce an amount of alanine required for survival, however, they do not produce alanine in an amount that can be utilized industrially. When an alanine dehydrogenase gene of a heterogenous microorganism is introduced into bacteria of the genus *Hydrogenophilus*, the gene functions within the genus *Hydrogenophilus* bacteria, and a highly active alanine dehydrogenase is produced, and therefore, the obtained transformants efficiently produce alanine using carbon dioxide as a sole carbon source. In particular, when alaD1 or alaD2 gene of *Geobacillus stearothermophilus*, or alaD1 or alaD2 gene of *Thermus thermophilus* is introduced into bacteria of the genus *Hydrogenophilus*, an especially highly active alanine dehydrogenase is produced.
- (ii) A gene encoding a modified alanine dehydrogenase in which an amino acid sequence of the N terminus portion of a maltose-binding protein has been added to the N terminus of an alanine dehydrogenase brings about a higher enzymatic activity expression in bacteria of the genus *Hydrogenophilus* as compared to a gene encoding an alanine dehydrogenase in which this amino acid sequence has not been added. As a result, a transformant of a bacterium of the genus *Hydrogenophilus* into which this modified alanine dehydrogenase gene has been introduced, produces alanine still more efficiently using carbon dioxide as a sole carbon source.

The present invention has been completed based on the above findings, and provides a transformant and a method for producing chemical products, which are described below.

Aspect 1. A DNA of (a1), (a2), or (a3) below:
- (a1) DNA which consists of a base sequence of SEQ ID NO: 1;
- (a2) DNA which consists of a base sequence having 90% or more identity with SEQ ID NO: 1, the DNA encoding a polypeptide having 2-keto-acid decarboxylase activity;
- (a3) DNA which hybridizes with a DNA consisting of a base sequence complementary to SEQ ID NO: 1 under stringent conditions, and which encodes a polypeptide having 2-keto-acid decarboxylase activity.

Aspect 2. A transformant obtained by introducing (a) a DNA according to aspect 1 and (b) an alcohol dehydrogenase gene into a bacterium of the genus *Hydrogenophilus*.

Aspect 3. The transformant according to aspect 2, wherein the alcohol dehydrogenase gene (b) is a DNA of (b1), (b2), (b3), (b4), (b5), or (b6) below:
- (b1) DNA which consists of a base sequence of SEQ ID NO: 2, 3, 4, or 5;
- (b2) DNA which consists of a base sequence having 90% or more identity with SEQ ID NO: 2, 3, 4, or 5, the DNA encoding a polypeptide having alcohol dehydrogenase activity;
- (b3) DNA which hybridizes with a DNA consisting of a base sequence complementary to SEQ ID NO: 2, 3, 4, or 5 under stringent conditions, and which encodes a polypeptide having alcohol dehydrogenase activity;
- (b4) DNA which encodes a polypeptide consisting of an amino acid sequence of SEQ ID NO: 6, 7, 8, or 9;
- (b5) DNA which encodes a polypeptide consisting of an amino acid sequence having 90% or more identity with SEQ ID NO: 6, 7, 8, or 9, the polypeptide having alcohol dehydrogenase activity;
- (b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity.

Aspect 4. The transformant according to aspect 2 or 3, wherein the bacterium of the genus *Hydrogenophilus* is *Hydrogenophilus thermoluteolus*.

Aspect 5. A method for producing isobutanol comprising a step of culturing the transformant according to any one of aspects 2 to 4, while using carbon dioxide as substantially a sole carbon source.

Aspect 6. A transformant obtained by introducing (c) a pyruvate decarboxylase gene of (c1), (c2), (c3), (c4), (c5), or (c6) below, and (b) an alcohol dehydrogenase gene, into a bacterium of the genus *Hydrogenophilus*:
- (c1) DNA which consists of a base sequence of SEQ ID NO: 10;
- (c2) DNA which consists of a base sequence having 90% or more identity with SEQ ID NO: 10, the DNA encoding a polypeptide having pyruvate decarboxylase activity;
- (c3) DNA which hybridizes with a DNA consisting of a base sequence complementary to SEQ ID NO: 10 under stringent conditions, and which encodes a polypeptide having pyruvate decarboxylase activity;
- (c4) DNA which encodes a polypeptide consisting of an amino acid sequence of SEQ ID NO: 11;
- (c5) DNA which encodes a polypeptide consisting of an amino acid sequence having 90% or more identity with SEQ ID NO: 11, the polypeptide having pyruvate decarboxylase activity;
- (c6) DNA which encodes a polypeptide consisting of an amino acid sequence having a deletion, substitution, or addition of one or a plurality of amino acids in the amino acid sequence of SEQ ID NO: 11, the polypeptide having pyruvate decarboxylase activity.

Aspect 7. The transformant according to aspect 6, wherein the alcohol dehydrogenase gene (b) is a DNA of (b1), (b2), (b3), (b4), (b5), or (b6) below:
- (b1) DNA which consists of a base sequence of SEQ ID NO: 2, 3, 4, or 5;
- (b2) DNA which consists of a base sequence having 90% or more identity with SEQ ID NO: 2, 3, 4, or 5, the DNA encoding a polypeptide having alcohol dehydrogenase activity;
- (b3) DNA which hybridizes with a DNA consisting of a base sequence complementary to SEQ ID NO: 2, 3, 4, or 5 under stringent conditions, and which encodes a polypeptide having alcohol dehydrogenase activity;
- (b4) DNA which encodes a polypeptide consisting of an amino acid sequence of SEQ ID NO: 6, 7, 8, or 9;
- (b5) DNA which encodes a polypeptide consisting of an amino acid sequence having 90% or more identity with SEQ ID NO: 6, 7, 8, or 9, the polypeptide having alcohol dehydrogenase activity;

(b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity.

Aspect 8. The transformant according to aspect 6 or 7, wherein the bacterium of the genus *Hydrogenophilus* is *Hydrogenophilus thermoluteolus*.

Aspect 9. A method for producing ethanol comprising a step of culturing the transformant according to any one of aspects 6 to 8, while using carbon dioxide as substantially a sole carbon source.

Aspect 10. A transformant obtained by introducing (d) an aldehyde-alcohol dehydrogenase gene into a bacterium of the genus *Hydrogenophilus*.

Aspect 11. The transformant according to aspect 10, wherein the aldehyde-alcohol dehydrogenase gene (d) is a DNA of (d1), (d2), (d3), (d4), (d5), (d6), (d7), (d8), or (d9) below:
(d1) DNA which consists of a base sequence of SEQ ID NO: 12 or 13;
(d2) DNA which consists of a base sequence having 90% or more identity with SEQ ID NO: 12 or 13, the DNA encoding a polypeptide having aldehyde-alcohol dehydrogenase activity;
(d3) DNA which hybridizes with a DNA consisting of a base sequence complementary to SEQ ID NO: 12 or 13 under stringent conditions, and which encodes a polypeptide having aldehyde-alcohol dehydrogenase activity;
(d4) DNA which encodes a polypeptide consisting of an amino acid sequence of SEQ ID NO: 14 or 15;
(d5) DNA which encodes a polypeptide consisting of an amino acid sequence having 90% or more identity with SEQ ID NO: 14 or 15, the polypeptide having aldehyde-alcohol dehydrogenase activity;
(d6) DNA which encodes a polypeptide consisting of an amino acid sequence having a deletion, substitution, or addition of one or a plurality of amino acids in the amino acid sequence of SEQ ID NO: 14 or 15, the polypeptide having aldehyde-alcohol dehydrogenase activity;
(d7) DNA which encodes a polypeptide consisting of an amino acid sequence of SEQ ID NO: 16, 17, 18, 19, 20, 21, 22, 23, or 24;
(d8) DNA which encodes a polypeptide consisting of an amino acid sequence having 90% or more identity with SEQ ID NO: 16, 17, 18, 19, 20, 21, 22, or 23 (with the proviso that the amino acid of amino acid number 568 in the polypeptide is Lys, Ala, Leu, Asn, Gly, Ser, Arg, or His), the polypeptide having aldehyde-alcohol dehydrogenase activity, or DNA which encodes a polypeptide consisting of an amino acid sequence having 90% or more identity with SEQ ID NO: 24 (with the proviso that the amino acid of amino acid number 575 in the polypeptide is Asn), the polypeptide having aldehyde-alcohol dehydrogenase activity;
(d9) DNA which encodes a polypeptide consisting of an amino acid sequence having a deletion, substitution, or addition of one or a plurality of amino acids in the amino acid sequence of SEQ ID NO: 16, 17, 18, 19, 20, 21, 22, or 23 (with the proviso that the amino acid of amino acid number 568 is Lys, Ala, Leu, Asn, Gly, Ser, Arg, or His), the polypeptide having aldehyde-alcohol dehydrogenase activity, or DNA which encodes a polypeptide consisting of an amino acid sequence having a deletion, substitution, or addition of one or a plurality of amino acids in the amino acid sequence of SEQ ID NO: 24 (with the proviso that the amino acid of amino acid number 575 is Asn), the polypeptide having aldehyde-alcohol dehydrogenase activity.

Aspect 12. The transformant according to aspect 11, wherein the DNA of (d7) is a DNA which consists of a base sequence of SEQ ID NO: 25, 26, 27, or 28.

Aspect 13. The transformant according to any one of aspects 10 to 12, wherein the bacterium of the genus *Hydrogenophilus* is *Hydrogenophilus thermoluteolus*.

Aspect 14. A method for producing ethanol comprising a step of culturing the transformant according to any one of aspects 10 to 13, while using carbon dioxide as substantially a sole carbon source.

Aspect 15. An aldehyde-alcohol dehydrogenase which consists of a polypeptide of (d7'), (d8'), or (d9') below (with the proviso that the amino acid at position 575 from the N terminus of polypeptides (d8') and (d9') is Asn):
(d7') polypeptide which consists of an amino acid sequence of SEQ ID NO: 24;
(d8') polypeptide which consists of an amino acid sequence having 90% or more identity with SEQ ID NO: 24, the polypeptide having aldehyde-alcohol dehydrogenase activity;
(d9') polypeptide which consists of an amino acid sequence having a deletion, substitution, or addition of one or a plurality of amino acids in the amino acid sequence of SEQ ID NO: 24, the polypeptide having aldehyde-alcohol dehydrogenase activity.

Aspect 16. An aldehyde-alcohol dehydrogenase gene which consists of a DNA of (d10'), (d11'), or (d12') below (with the proviso that the 3 nucleotides from position 1723 to position 1725 from the 5' end of the DNAs of (d11') and (d12') are AAC or AAT):
(d10') DNA which consists of a base sequence of SEQ ID NO: 27 or 28;
(d11') DNA which consists of a base sequence having 90% or more identity with SEQ ID NO: 27 or 28, the DNA encoding a polypeptide having aldehyde-alcohol dehydrogenase activity;
(d12') DNA which hybridizes with a DNA consisting of a base sequence complementary to SEQ ID NO: 27 or 28 under stringent conditions, the DNA encoding a polypeptide having aldehyde-alcohol dehydrogenase activity.

Aspect 17. A transformant obtained by introducing (e) an alanine dehydrogenase gene into a bacterium of the genus *Hydrogenophilus*.

Aspect 18. The transformant according to aspect 17, wherein the alanine dehydrogenase gene (e) is a DNA of (e1), (e2), (e3), (e4), (e5), (e6), (e7), (e8), (e9), (e10), (e11), or (e12) below:
(e1) DNA which consists of a base sequence of SEQ ID NO: 29, 30, 31, or 32;
(e2) DNA which consists of a base sequence having 90% or more identity with SEQ ID NO: 29, 30, 31, or 32, the DNA encoding a polypeptide having alanine dehydrogenase activity;
(e3) DNA which hybridizes with a DNA consisting of a base sequence complementary to SEQ ID NO: 29, 30, 31, or 32 under stringent conditions, and which encodes a polypeptide having alanine dehydrogenase activity;

(e4) DNA which encodes a polypeptide consisting of an amino acid sequence of SEQ ID NO: 33, 34, 35, or 36;
(e5) DNA which encodes a polypeptide consisting of an amino acid sequence having 90% or more identity with SEQ ID NO: 33, 34, 35, or 36, the polypeptide having alanine dehydrogenase activity;
(e6) DNA which encodes a polypeptide consisting of an amino acid sequence having a deletion, substitution, or addition of one or a plurality of amino acids in the amino acid sequence of SEQ ID NO: 33, 34, 35, or 36, the polypeptide having alanine dehydrogenase activity;
(e7) DNA which encodes a polypeptide consisting of an amino acid sequence in which an amino acid sequence of SEQ ID NO: 37 is added to the N terminus of the amino acid sequence of SEQ ID NO: 33, 34, 35, or 36;
(e8) DNA which encodes a polypeptide consisting of an amino acid sequence in which the amino acid sequence of SEQ ID NO: 37 is added to the N terminus of the amino acid sequence having 90% or more identity with SEQ ID NO: 33, 34, 35, or 36, the polypeptide having alanine dehydrogenase activity;
(e9) DNA which encodes a polypeptide consisting of an amino acid sequence in which the amino acid sequence of SEQ ID NO: 37 is added to the N terminus of the amino acid sequence having a deletion, substitution, or addition of one or a plurality of amino acids in the amino acid sequence of SEQ ID NO: 33, 34, 35, or 36, the polypeptide having alanine dehydrogenase activity;
(e10) DNA which consists of a base sequence in which a base sequence of SEQ ID NO: 38 is added to the 5' end of the base sequence of SEQ ID NO: 29, 30, 31, or 32;
(e11) DNA which consists of a base sequence in which the base sequence of SEQ ID NO: 38 is added to the 5' end of the base sequence having 90% or more identity with SEQ ID NO: 29, 30, 31, or 32, the DNA encoding a polypeptide having alanine dehydrogenase activity;
(e12) DNA which consists of a base sequence in which the base sequence of SEQ ID NO: 38 is added to the 5' end of a base sequence of the DNA hybridizing with a DNA consisting of a base sequence complementary to SEQ ID NO: 29, 30, 31, or 32 under stringent conditions, and which encodes a polypeptide having alanine dehydrogenase activity.

Aspect 19. The transformant according to aspect 17 or 18, wherein the bacterium of the genus *Hydrogenophilus* is *Hydrogenophilus thermoluteolus*.

Aspect 20. A method for producing alanine comprising a step of culturing the transformant according to any one of aspects 17 to 19, while using carbon dioxide as substantially a sole carbon source.

Aspect 21. A modified alanine dehydrogenase, in which a polypeptide consisting of an amino acid sequence of SEQ ID NO: 37 is added to the N terminus of an alanine dehydrogenase.

Aspect 22. The modified alanine dehydrogenase according to aspect 21, which consists of an amino acid sequence of SEQ ID NO: 39.

Aspect 23. A modified alanine dehydrogenase gene, in which a polynucleotide consisting of a base sequence of SEQ ID NO: 38 is added to the 5' end of an alanine dehydrogenase gene.

Aspect 24. The modified alanine dehydrogenase gene according to aspect 23, which consists of a base sequence of SEQ ID NO: 40.

Advantageous Effects of Invention

Countermeasures to suppress the increase in carbon dioxide include reduction of carbon dioxide emission and fixation of emitted carbon dioxide. In order to reduce carbon dioxide emission, solar energy, wind energy, geothermal energy, and the like are utilized in place of fossil energy. However, the utilization of such energies have not been able to sufficiently suppress the increase in carbon dioxide actually. Therefore, there is a need to advance the fixation or recycling of emitted carbon dioxide.

Carbon dioxide can be fixed physically or chemically, however, if carbon dioxide is fixed by utilizing a living organism, then organic substances that can be utilized as food, feed, fuel, and the like, can be produced. Namely, carbon dioxide itself as a resource can be directly converted into valuable chemical products. Accordingly, both of two problems of global warming due to the increase in carbon dioxide and difficulty in securing food, feed, and fuel can be solved.

Hydrogen oxidizing bacteria are bacteria which can grow by utilizing chemical energy generated by the reaction of hydrogen and oxygen and by using carbon dioxide as a sole carbon source. Since hydrogen oxidizing bacteria can produce chemical products using a mixed gas of oxygen, hydrogen, and carbon dioxide as a raw material, they can efficiently carry out organification of carbon dioxide and be cultured in a simple culture medium. Growth of hydrogen oxidizing bacteria is generally slow, however, the growth rate of hydrogen oxidizing bacteria of the genus *Hydrogenophilus* is remarkably high. "Journal of Mitsubishi Research Institute No. 34 1999" assesses genus *Hydrogenophilus* bacteria as follows: "Their proliferative capacity is so high that it cannot be compared with the carbon dioxide fixation ability of plants, which truly indicates the high carbon dioxide fixation ability of microorganisms".

When a heterologous gene having natural base sequence is introduced into bacteria of the genus *Hydrogenophilus* using a vector that functions within the genus *Hydrogenophilus* bacteria, a functioning protein often is not produced. According to the present invention, by introducing particular genes into bacteria of the genus *Hydrogenophilus*, the genes function within the genus *Hydrogenophilus* bacteria, and isobutanol, ethanol, or alanine can be produced.

As described above, bacteria of the genus *Hydrogenophilus* have a particularly remarkable carbon dioxide fixation ability among organisms having carbon dioxide fixation ability, and therefore, by using the transformant of the present invention, carbon dioxide can be fixed and isobutanol, ethanol, or alanine can be produced at an industrial level.

MODE FOR CARRYING OUT THE INVENTION

The present invention is described in detail below:
(1) Transformant Having Isobutanol Producing Ability The codon-optimized 2-keto-acid decarboxylase gene of the present invention is obtained by codon-optimization of the 2-keto-acid decarboxylase of *Lactococcus lactis*, and is different from the 2-keto-acid decarboxylase gene (kivD) of *Lactococcus lactis* in base sequence. This gene is a DNA which consists of the base sequence of SEQ ID NO: 1. This codon-optimized 2-keto-acid decarboxylase gene functions within bacteria of the genus *Hydrogenophilus*, and can bring about 2-keto-acid decarboxylase activity expression.

The amino acid sequence of 2-keto-acid decarboxylase produced based on this codon-optimized 2-keto-acid decarboxylase gene is the same as that of the 2-keto-acid decarboxylase of *Lactococcus lactis* (SEQ ID NO: 41).

DNA which consists of a base sequence having 90% or more, preferably 95% or more, more preferably 98% or more, further more preferably 99% or more identity with SEQ ID NO: 1, the DNA encoding a polypeptide having 2-keto-acid decarboxylase activity, can also be used to bring about 2-keto-acid decarboxylase activity expression within bacteria of the genus *Hydrogenophilus*.

In the present invention, the identities of base sequences were calculated using GENETYX ver. 17 (made by GENETYX Corporation).

DNA which hybridizes with a DNA consisting of a base sequence complementary to SEQ ID NO: 1 under stringent conditions, the DNA encoding a polypeptide having 2-keto-acid decarboxylase activity, can also be used.

In the present invention, "stringent conditions" means conditions in which hybridization is performed in a hybridization solution at a salt concentration of 6×SSC at temperatures from 50 to 60° C. for 16 hours, and then washing is performed with a solution at a salt concentration of 0.1×SSC.

The base sequences of the above-described homologues of the codon-optimized 2-keto-acid decarboxylase gene (SEQ ID NO: 1) are desirably different from SEQ ID NO: 1 to the extent that the amino acid sequence of the encoded 2-keto-acid decarboxylase is the same as that of 2-keto-acid decarboxylase of *Lactococcus lactis* (SEQ ID NO: 41).

The present invention also encompasses a vector comprising the above-described codon-optimized 2-keto-acid decarboxylase gene or the homologues thereof (in particular, a vector that functions within bacteria of the genus *Hydrogenophilus*).

By introducing an alcohol dehydrogenase gene together with the above-described codon-optimized 2-keto-acid decarboxylase gene or the homologue thereof into bacteria of the genus *Hydrogenophilus*, the genus *Hydrogenophilus* bacteria come to produce isobutanol.

Accordingly, the present invention encompasses a transformant which is obtained by introducing (a) (a1) DNA which consists of a base sequence of SEQ ID NO: 1, (a2) DNA which consists of a base sequence having 90% or more identity with SEQ ID NO: 1, the DNA encoding a polypeptide having 2-keto-acid decarboxylase activity, or (a3) DNA which hybridizes with a DNA consisting of a base sequence complementary to SEQ ID NO: 1 under stringent conditions, and which encodes a polypeptide having 2-keto-acid decarboxylase activity, and (b) DNA of an alcohol dehydrogenase gene, into a host bacterium of the genus *Hydrogenophilus*. In other words, this transformant possesses exogenous DNAs of (a) and (b) described above.

Examples of the alcohol dehydrogenase gene include (b1) alcohol dehydrogenase gene (adhP) of *Klebsiella pneumoniae*, alcohol dehydrogenase gene (adhP) of *Geobacillus thermocatenulatus*, alcohol dehydrogenase gene (adhP) of *Geobacillus thermoglucosidasius*, and alcohol dehydrogenase gene (adhA) of *Geobacillus thermoglucosidasius*, which are preferable in that they have good isobutanol production efficiency. The base sequences of these genes are SEQ ID NOs: 2, 3, 4, and 5, respectively.

(b2) DNA which consists of a base sequence having 90% or more, preferably 95% or more, more preferably 98% or more, further more preferably 99% or more identity with SEQ ID NO: 2, 3, 4, or 5, the DNA encoding a polypeptide having alcohol dehydrogenase activity, and (b3) DNA which hybridizes with a DNA consisting of a base sequence complementary to SEQ ID NO: 2, 3, 4, or 5 under stringent conditions, and which encodes a polypeptide having alcohol dehydrogenase activity, are also preferable.

In addition, examples of the alcohol dehydrogenase gene include (b4) DNA which encodes a polypeptide consisting of an amino acid sequence of SEQ ID NO: 6, 7, 8, or 9, or (b5) DNA which encodes a polypeptide consisting of an amino acid sequence having 90% or more, preferably 95% or more, more preferably 98% or more, further more preferably 99% or more identity with SEQ ID NO: 6, 7, 8, or 9, the polypeptide having alcohol dehydrogenase activity, which are also preferable.

SEQ ID NOs: 6, 7, 8, and 9 are amino acid sequences of alcohol dehydrogenase ADHP of *Klebsiella pneumoniae*, *Geobacillus thermocatenulatus*, and *Geobacillus thermoglucosidasius*, and alcohol dehydrogenase ADHA of *Geobacillus thermoglucosidasius*, respectively. In the present invention, the identities of amino acid sequences were calculated using GENETYX ver. 17 (made by GENETYX Corporation).

(b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity, is also preferable.

In the present invention, examples of plurality include 1 to 5, in particular 1 to 3, in particular 1 to 2, and particularly 1.

In the present invention, when an amino acid residue of a polypeptide that has a certain activity is substituted, the amino acid residue may be substituted by another chemically similar amino acid residue, in order to carry out substitution so that the polypeptide has the certain activity after substitution (in particular, so that the polypeptide maintains an activity that is the same level as the certain activity). For example, a hydrophobic amino acid residue can be substituted by another hydrophobic amino acid residue, or a charged amino acid residue can be substituted by another charged amino acid residue having the same charge. Chemically similar amino acids which can be thus substituted are well known to those skilled in the art. Examples of amino acids which have a nonpolar (hydrophobic) sidechain include glycine, alanine, valine, isoleucine, leucine, proline, tryptophan, phenylalanine, methionine, and the like, and these amino acids can be substituted with each other. Examples of neutral amino acids which have a polar sidechain include serine, threonine, tyrosine, glutamine, asparagine, cysteine, and the like, and these amino acids can be substituted with each other. Examples of (basic) amino acids which have a positive charge include arginine, histidine, lysine, and the like, and these amino acids can be substituted with each other. In addition, examples of (acidic) amino acids which have a negative charge include aspartic acid, glutamic acid, and the like, and these amino acids can be substituted with each other.

In the present invention, when a nucleotide of a DNA which encodes a polypeptide that has a certain activity is substituted, there is a tendency for the polypeptide to have the certain activity after substitution (in particular, to maintain an activity that is the same level as the certain activity), if the nucleotide is substituted so that the amino acid sequence of the encoded polypeptide is unchanged. In addition, if a nucleotide is substituted so that the corresponding amino acid residue is substituted by another chemically similar amino acid residue, there is a tendency for the polypeptide to have the certain activity after substitution (in particular, to maintain an activity that is the same level as the certain activity).

In the present invention, in order to confirm that a polypeptide has a 2-keto-acid decarboxylase activity, a test polypeptide is reacted with 2-ketoisovalerate under the coexistence of alcohol dehydrogenase and NADH, and decrease in absorbance at 340 nm is detected. 2-keto-acid decarboxylase produces isobutyraldehyde from 2-ketoisovalerate, and the coexisting alcohol dehydrogenase produces isobutanol from isobutyraldehyde. Alcohol dehydrogenase consumes NADH when isobutanol is produced from isobutyraldehyde, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have 2-keto-acid decarboxylase activity.

In the present invention, in order to confirm that a polypeptide has an alcohol dehydrogenase activity in which isobutyraldehyde is used as a substrate, a test polypeptide is reacted with isobutyraldehyde under the coexistence of NADH, and decrease in absorbance at 340 nm is detected. Alcohol dehydrogenase produces isobutanol from isobutyraldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which isobutyraldehyde is used as a substrate.

(2) Transformant Having Ethanol Producing Ability
First Transformant Having Ethanol Producing Ability The present invention encompasses a transformant obtained by introducing (c) (c1) DNA which consists of a base sequence of SEQ ID NO: 10, (c2) DNA which consists of a base sequence having 90% or more, in particular 95% or more, in particular 98% or more, in particular 99% or more identity with SEQ ID NO: 10, the DNA encoding a polypeptide having pyruvate decarboxylase activity, or (c3) DNA which hybridizes with a DNA consisting of a base sequence complementary to SEQ ID NO: 10 under stringent conditions, and which encodes a polypeptide having pyruvate decarboxylase activity and DNA of (b) an alcohol dehydrogenase gene, into a host bacterium of the genus *Hydrogenophilus*. In other words, this transformant possesses exogenous DNAs of (c) and (b). This transformant can produce ethanol due to the possession of DNAs of (c) and (b).

SEQ ID NO: 10 is a base sequence of the pyruvate decarboxylase gene (pdc gene) of *Gluconobacter oxydans*.

Examples of pyruvate decarboxylase genes which can also be used include (c4) DNA which encodes a polypeptide consisting of an amino acid sequence of SEQ ID NO: 11, (c5) DNA which encodes a polypeptide consisting of an amino acid sequence having 90% or more, preferably 95% or more, more preferably 98% or more, further more preferably 99% or more identity with SEQ ID NO: 11, the polypeptide having pyruvate decarboxylase activity, or (c6) DNA which encodes a polypeptide consisting of an amino acid sequence having a deletion, substitution, or addition of one or a plurality of amino acids in the amino acid sequence of SEQ ID NO: 11, the polypeptide having pyruvate decarboxylase activity.

SEQ ID NO: 11 is an amino acid sequence of a pyruvate decarboxylase of *Gluconobacter oxydans*.

Examples of (b) alcohol dehydrogenase gene include (b1) alcohol dehydrogenase gene (adhP) of *Klebsiella pneumoniae*, alcohol dehydrogenase gene (adhP) of *Geobacillus thermocatenulatus*, alcohol dehydrogenase gene (adhP) of *Geobacillus thermoglucosidasius*, and alcohol dehydrogenase gene (adhA) of *Geobacillus thermoglucosidasius*, which are preferable in that they have good ethanol production efficiency. The base sequences of these genes are SEQ ID NOs: 2, 3, 4, and 5, respectively.

(b2) DNA which consists of a base sequence having 95% or more, in particular 98% or more, in particular 99% or more identity with SEQ ID NO: 2, 3, 4, or 5, the DNA encoding a polypeptide having alcohol dehydrogenase activity, can also be used preferably. (b3) DNA which hybridizes with a DNA consisting of a base sequence complementary to SEQ ID NO: 2, 3, 4, or 5 under stringent conditions, and which encodes a polypeptide having alcohol dehydrogenase activity, can also be used preferably.

(b4) DNA which encodes a polypeptide consisting of an amino acid sequence of SEQ ID NO: 6, 7, 8, or 9, can also be used preferably as the alcohol dehydrogenase gene. Furthermore, (b5) DNA which encodes a polypeptide consisting of an amino acid sequence having 90% or more, preferably 95% or more, more preferably 98% or more, further more preferably 99% or more identity with SEQ ID NO: 6, 7, 8, or 9, the polypeptide having alcohol dehydrogenase activity, and (b6) DNA which encodes a polypeptide consisting of an amino acid sequence having a deletion, substitution, or addition of one or a plurality of amino acids in the amino acid sequence of SEQ ID NO: 6, 7, 8, or 9, the polypeptide having alcohol dehydrogenase activity, can also be used preferably.

SEQ ID NOs: 6, 7, 8, and 9 are amino acid sequences of alcohol dehydrogenase ADHP of *Klebsiella pneumoniae*, *Geobacillus thermocatenulatus*, and *Geobacillus thermoglucosidasius*, and alcohol dehydrogenase ADHA of *Geobacillus thermoglucosidasius*, respectively.

In the present invention, in order to confirm that a polypeptide has a pyruvate decarboxylase activity, a test polypeptide is reacted with pyruvic acid under the coexistence of alcohol dehydrogenase and NADH, and decrease in absorbance at 340 nm is detected. Pyruvate decarboxylase produces acetaldehyde from pyruvic acid, and alcohol dehydrogenase produces ethanol from acetaldehyde. Alcohol dehydrogenase consumes NADH when ethanol is produced from acetaldehyde, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have pyruvate decarboxylase activity.

In the present invention, in order to confirm that a polypeptide has an alcohol dehydrogenase activity in which acetaldehyde is used as a substrate, a test polypeptide is reacted with acetaldehyde under the coexistence of NADH, and decrease in absorbance at 340 nm is detected. Alcohol dehydrogenase produces ethanol from acetaldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which acetaldehyde is used as a substrate.

Second Transformant Having Ethanol Producing Ability

The present invention encompasses a transformant which is obtained by introducing DNA of (d) an aldehyde-alcohol dehydrogenase gene, into a host bacterium of genus *Hydrogenophilus*. In other words, this transformant possesses an exogenous DNA of (d) an aldehyde-alcohol dehydrogenase gene. This transformant can produce ethanol due to the possession of DNA of (d).

Examples of the aldehyde-alcohol dehydrogenase gene include (d1) aldehyde-alcohol dehydrogenase gene (adhE) of *Escherichia coli*, and aldehyde-alcohol dehydrogenase gene (adhE) of *Clostridium thermocellum*, which are preferable in that they have good ethanol production efficiency. The base sequence of *Escherichia coli* adhE is SEQ ID NO: 12, and the base sequence of *Clostridium thermocellum* adhE is SEQ ID NO: 13.

(d2) DNA which consists of a base sequence having 90% or more, in particular 95% or more, in particular 98% or more, in particular 99% or more identity with a DNA consisting of a base sequence of SEQ ID NO: 12 or 13, and which encodes a polypeptide having aldehyde-alcohol dehydrogenase activity, and (d3) DNA which hybridizes with a DNA consisting of a base sequence complementary to SEQ ID NO: 12 or 13 under stringent conditions, and which encodes a polypeptide having aldehyde-alcohol dehydrogenase activity, can also be used preferably.

(d4) DNA which encodes a polypeptide consisting of an amino acid sequence of SEQ ID NO: 14 or 15, can also be used preferably. Furthermore, (d5) DNA which encodes a polypeptide consisting of an amino acid sequence having 90% or more, in particular 95% or more, in particular 98% or more, in particular 99% or more identity with SEQ ID NO: 14 or 15, the polypeptide having aldehyde-alcohol dehydrogenase activity, and (d6) DNA which encodes a polypeptide consisting of an amino acid sequence having a deletion, substitution, or addition of one or a plurality of amino acids in the amino acid sequence of SEQ ID NO: 14 or 15, the polypeptide having aldehyde-alcohol dehydrogenase activity, can also be used preferably.

SEQ ID NO: 14 is an amino acid sequence of the aldehyde-alcohol dehydrogenase (ADHE) of *Escherichia coli*, and SEQ ID NO: 15 is an amino acid sequence of the aldehyde-alcohol dehydrogenase (ADHE) of *Clostridium thermocellum*.

The activity of aldehyde-alcohol dehydrogenase is inhibited under aerobic conditions, and thus, in the present invention, an attempt was made to use an aldehyde-alcohol dehydrogenase that expresses high activity under aerobic conditions, within bacteria of the genus *Hydrogenophilus*.

As a result, it was found that a mutant ADHE in which Glu at amino acid number 568 of SEQ ID NO: 14, which is the amino acid sequence of an aldehyde-alcohol dehydrogenase of *Escherichia coli*, has been substituted by Lys, Ala, Leu, Asn, Gly, Ser, Arg, or His, can express high activity under aerobic conditions within bacteria of the genus *Hydrogenophilus*. The amino acid sequences of mutant ADHE, in which the Glu of amino acid number 568 has been substituted by Lys, Ala, Leu, Asn, Gly, Ser, Arg, and His, are shown in SEQ ID NOs: 16, 17, 18, 19, 20, 21, 22, and 23, respectively.

Mutant ADHE(E568K) which consists of the amino acid sequence of SEQ ID NO: 16, in which Glu of amino acid number 568 of SEQ ID NO: 14 has been substituted by Lys, is especially preferable.

Therefore, in the present invention, (d7) DNA which encodes a polypeptide consisting of an amino acid sequence in which Glu of amino acid number 568 of SEQ ID NO: 14 has been substituted by Lys, Ala, Leu, Asn, Gly, Ser, Arg, or His, can be preferably used.

(d8) DNA which encodes a polypeptide consisting of an amino acid sequence having 90% or more, in particular 95% or more, in particular 98% or more, in particular 99% or more identity with an amino acid sequence in which Glu of amino acid number 568 of SEQ ID NO: 14 has been substituted by Lys, Ala, Leu, Asn, Gly, Ser, Arg, or His (SEQ ID NO: 16, 17, 18, 19, 20, 21, 22, or 23), the polypeptide having aldehyde-alcohol dehydrogenase activity, and (d9) DNA which encodes a polypeptide consisting of an amino acid sequence having a deletion, substitution, or addition of one or a plurality of amino acids in the amino acid sequence in which Glu of amino acid number 568 of SEQ ID NO: 14 has been substituted by Lys, Ala, Leu, Asn, Gly, Ser, Arg, or His (SEQ ID NO: 16, 17, 18, 19, 20, 21, 22, or 23), the polypeptide having aldehyde-alcohol dehydrogenase activity, can also be preferably used.

Note, however, that in the polypeptides of (d8) and (d9), the amino acid of amino acid number 568 is Lys, Ala, Leu, Asn, Gly, Ser, Arg, or His, respectively, or in the order described above.

A base sequence of the mutant adhE in which the amino acid at position 568 of the expressed aldehyde-alcohol dehydrogenase becomes Lys, is a base sequence in which GAG at base positions 1702 to 1704 of SEQ ID NO: 12, which is a base sequence of *Escherichia coli* adhE, has been substituted by AAG or AAA (SEQ ID NO: 25 or 26).

A base sequence of adhE in which the amino acid at position 568 of the expressed aldehyde-alcohol dehydrogenase becomes Ala, is a base sequence in which GAG at base positions 1702 to 1704 of SEQ ID NO: 12 has been substituted by GCT, GCC, GCA, or GCG.

A base sequence of adhE in which the amino acid at position 568 of the expressed aldehyde-alcohol dehydrogenase becomes Leu is a base sequence in which GAG at base positions 1702 to 1704 of SEQ ID NO: 12 has been substituted by TTA, TTG, CTT, CTC, CTA, or CTG.

A base sequence of adhE in which the amino acid at position 568 of the expressed aldehyde-alcohol dehydrogenase becomes Asn is a base sequence in which the GAG at base positions 1702 to 1704 of SEQ ID NO: 12 has been substituted by AAT or AAC.

A base sequence of adhE in which the amino acid at position 568 of the expressed aldehyde-alcohol dehydrogenase becomes Gly, is a base sequence in which the GAG at base positions 1702 to 1704 of SEQ ID NO: 12 has been substituted by GGT, GGC, GGA, or GGG.

A base sequence of adhE in which the amino acid at position 568 of the expressed aldehyde-alcohol dehydrogenase becomes Ser, is a base sequence in which the GAG at base positions 1702 to 1704 of SEQ ID NO: 12 has been substituted by TCT, TCC, TCA, TCG, AGT, or AGC.

A base sequence of adhE in which the amino acid at position 568 of the expressed aldehyde-alcohol dehydrogenase becomes Arg, is a base sequence in which the GAG at base positions 1702 to 1704 of SEQ ID NO: 12 has been substituted by CGT, CGC, CGA, AGA, or AGG.

A base sequence of adhE in which the amino acid at position 568 of the expressed aldehyde-alcohol dehydrogenase becomes His, is a base sequence in which the GAG at base positions 1702 to 1704 of SEQ ID NO: 12 has been substituted by CAT or CAC.

In particular, SEQ ID NO: 25 or 26 is preferable in terms of good ethanol production efficiency by bacteria of the genus *Hydrogenophilus*, and SEQ ID NO: 25 is more preferable.

In addition, DNA which consists of a base sequence having 90% or more, in particular 95% or more, in particular 98% or more, in particular 99% or more identity with a base sequence of the above-described mutant adhE encoding a mutant ADHE in which Glu of amino acid number 568 of SEQ ID NO: 14 of the aldehyde-alcohol dehydrogenase (ADHE) of *Escherichia coli* has been substituted by Lys, Ala, Leu, Asn, Gly, Ser, Arg, or His, the DNA encoding a polypeptide having aldehyde-alcohol dehydrogenase activity (a homologue of mutant adhE of *Escherichia coli*), as well as DNA which hybridizes under stringent conditions with a DNA consisting of a base sequence complementary to the base sequence of the above-described mutant adhE encoding a mutant ADHE in which Glu of amino acid number 568 of SEQ ID NO: 14 of the aldehyde-alcohol dehydrogenase (ADHE) of *Escherichia coli* has been substituted by Lys, Ala, Leu, Asn, Gly, Ser, Arg, or His, and which encodes a polypeptide having aldehyde-alcohol dehydrogenase activity (a homologue of mutant adhE of *Escherichia coli*), can also be preferably used.

Note, however, that in the above-described homologue of mutant adhE of *Escherichia coli*, the base sequence of the 3 nucleotides that correspond to amino acid number 568 of the mutant ADHE of *Escherichia coli* is the same as any of the 3 nucleotides that correspond to Lys, Ala, Leu, Asn, Gly, Ser, Arg, or His of amino acid number 568 of the mutant ADHE of *Escherichia coli*.

Namely, the nucleotides of base numbers 1702 to 1704 of the above-described homologue of the DNA encoding the mutant ADHE of *Escherichia coli*, in which amino acid number 568 is Lys, is AAG or AAA.

The nucleotides of base numbers 1702 to 1704 of the homologue of the DNA encoding the mutant ADHE of *Escherichia coli*, in which amino acid number 568 is Ala, is GCT, GCC, GCA, or GCG.

The nucleotides of base numbers 1702 to 1704 of the above-described homologue of the DNA encoding the mutant ADHE of *Escherichia coli*, in which amino acid number 568 is Leu, is TTA, TTG, CTT, CTC, CTA, or CTG.

The nucleotides of base numbers 1702 to 1704 of the above-described homologue of the DNA encoding the mutant ADHE of *Escherichia coli*, in which amino acid number 568 is Asn, is AAT or AAC.

The nucleotides of base numbers 1702 to 1704 of the above-described homologue of the DNA encoding the mutant ADHE of *Escherichia coli*, in which amino acid number 568 is Gly, is GGT, GGC, GGA, or GGG.

The nucleotides of base numbers 1702 to 1704 of the above-described homologue of the DNA encoding the mutant ADHE of *Escherichia coli*, in which amino acid number 568 is Ser, is TCT, TCC, TCA, TCG, AGT, or AGC.

The nucleotides of base numbers 1702 to 1704 of the above-described homologue of the DNA encoding the mutant ADHE of *Escherichia coli*, in which amino acid number 568 is Arg, is GCT, CGC, CGA, AGA, or AGG.

The nucleotides of base numbers 1702 to 1704 of the above-described homologue of the DNA encoding the mutant ADHE of *Escherichia coli*, in which amino acid number 568 is His, is CAT or CAC.

It was found that a mutant ADHE consisting of an amino acid sequence of SEQ ID NO: 24 in which Asp of amino acid number 575 of SEQ ID NO: 15, which is the amino acid sequence of the aldehyde-alcohol dehydrogenase (ADHE) of *Clostridium thermocellum*, has been substituted by Asn, can express high activity under aerobic conditions in bacteria of the genus *Hydrogenophilus*.

Therefore, in the present invention, (d7) DNA (adhE (D575N)) encoding a polypeptide which consists of an amino acid sequence in which Asp of amino acid number 575 of SEQ ID NO: 15 has been substituted by Asn (SEQ ID NO: 24), can be preferably introduced into bacteria of the genus *Hydrogenophilus*.

(d8) DNA which encodes a polypeptide consisting of an amino acid sequence having 90% or more, in particular 95% or more, in particular 98% or more, in particular 99% or more identity with an amino acid sequence in which Asp of amino acid number 575 of SEQ ID NO: 15 has been substituted by Asn (SEQ ID NO: 24), the polypeptide having aldehyde-alcohol dehydrogenase activity (a homologue of mutant ADHE of *Clostridium thermocellum*), and (d9) DNA which encodes a polypeptide consisting of an amino acid sequence having a deletion, substitution, or addition of one or a plurality of amino acids in the amino acid sequence in which Asp of amino acid number 575 of SEQ ID NO: 15 has been substituted by Asn (SEQ ID NO: 24), the polypeptide having aldehyde-alcohol dehydrogenase activity (a homologue of mutant ADHE of *Clostridium thermocellum*), can also be preferably used.

Note, however, that in the homologues of mutant ADHE of *Clostridium thermocellum* of (d8) and (d9), the amino acid of amino acid number 575 is Asn.

By introducing a mutant *Clostridium thermocellum* adhE gene that gives rise to the above-described amino acid substitution, into a bacterium of the genus *Hydrogenophilus*, the obtained transformant becomes able to highly express aldehyde-alcohol dehydrogenase activity under aerobic conditions.

The base sequence of mutant adhE in which the amino acid at position 575 of the expressed aldehyde-alcohol dehydrogenase is Asn, is a base sequence in which GAC of base numbers 1723 to 1725 of SEQ ID NO: 13, which is the base sequence of *Clostridium thermocellum* adhE gene, is substituted by AAC or AAT (SEQ ID NO: 27 or 28). In particular, DNA which consists of the base sequence of SEQ ID NO: 27 is preferable.

DNA which consists of a base sequence having 90% or more, in particular 95% or more, in particular 98% or more, in particular 99% or more identity with a DNA consisting of a base sequence of SEQ ID NO: 27 or 28, and which encodes a polypeptide having aldehyde-alcohol dehydrogenase activity (a homologue of mutant adhE of *Clostridium thermocellum*), and DNA which hybridizes with a DNA consisting of a base sequence complementary to SEQ ID NO: 27 or 28 under stringent conditions, and which encodes a polypeptide having aldehyde-alcohol dehydrogenase activity (a homologue of mutant adhE of *Clostridium thermocellum*), can also be preferably used.

Note, however, that in the homologue of mutant adhE of *Clostridium thermocellum* which consists of a base sequence of SEQ ID NO: 27 or 28, the nucleotide of base numbers 1723 to 1725 are AAC or AAT.

In the present invention, an aldehyde-alcohol dehydrogenase is provided which consist of (d7') polypeptide which consists of an amino acid sequence of SEQ ID NO: 24, (d8') polypeptide which consists of an amino acid sequence having 90% or more identity with SEQ ID NO: 24, the polypeptide having aldehyde-alcohol dehydrogenase activity, or (d9') polypeptide which consists of an amino acid sequence having a deletion, substitution, or addition of one or a plurality of amino acids in the amino acid sequence of SEQ ID NO: 24, the polypeptide having aldehyde-alcohol dehydrogenase activity. Note, however, that the amino acids at position 575 from the N terminus of the polypeptides of (d8') and (d9') are Asn, respectively.

This polypeptide can be expressed within bacteria of the genus *Hydrogenophilus* and be preferably used for ethanol production, or be used for ethanol production by enzyme reaction.

The present invention also provides an aldehyde-alcohol dehydrogenase gene consisting of (d10') DNA which consists of a base sequence of SEQ ID NO: 27 or 28, (d11') DNA which consists of a base sequence having 90% or more identity with SEQ ID NO: 27 or 28, the DNA encoding a polypeptide having aldehyde-alcohol dehydrogenase activity, or (d12') DNA which hybridizes with a DNA consisting of a base sequence complementary to SEQ ID NO: 27 or 28 under stringent conditions, and which encodes a polypeptide having aldehyde-alcohol dehydrogenase activity. Note, however, that the 3 nucleotides at positions 1723 to 1725 from the 5' end of the DNA of (d11') or (d12') are AAC or AAT.

The present invention encompasses a vector comprising this aldehyde-alcohol dehydrogenase gene (in particular, a vector that functions within bacteria of the genus *Hydrogenophilus*).

This aldehyde-alcohol dehydrogenase gene and the vector comprising the gene can preferably be used for ethanol production in bacteria of the genus *Hydrogenophilus*.

Aldehyde-alcohol dehydrogenase is a bifunctional enzyme which possesses both an aldehyde dehydrogenase activity that catalyzes the reaction of producing acetaldehyde from acetyl-CoA, and an alcohol dehydrogenase activity that catalyzes the reaction of producing ethanol from acetaldehyde.

In the present invention, it is determined that there is aldehyde-alcohol dehydrogenase activity, when a test polypeptide shows both an aldehyde dehydrogenase activity in which acetyl-CoA is used as a substrate, and an alcohol dehydrogenase activity in which acetaldehyde is used as a substrate.

In the present invention, in order to confirm that a polypeptide has an aldehyde dehydrogenase activity in which acetyl-CoA is used as a substrate, a test polypeptide is reacted with acetyl-CoA under the coexistence of NADH and decrease in absorbance at 340 nm is detected. Aldehyde dehydrogenase produces acetaldehyde from acetyl-CoA which is accompanied by the conversion of NADH to NAD, and thus decrease in the amount of NADH is detected using decrease in absorbance at 340 nm as an index. If the test polypeptide reduces absorbance at 340 nm even by a slight degree, the polypeptide is determined to have aldehyde dehydrogenase activity in which acetyl-CoA is used as a substrate.

In order to confirm that a polypeptide has an alcohol dehydrogenase activity in which acetaldehyde is used as a substrate, a test polypeptide is reacted with acetaldehyde under the coexistence of NADH, and decrease in absorbance at 340 nm is detected. Alcohol dehydrogenase produces ethanol from acetaldehyde which is accompanied by the conversion of NADH to NAD, and thus decrease in the amount of NADH is detected using decrease in absorbance at 340 nm as an index. Specifically, the method described in item "Examples" is carried out. If the test polypeptide reduces absorbance at 340 nm even by a slight degree, the polypeptide is determined to have alcohol dehydrogenase activity in which acetaldehyde is used as a substrate.

(3) Transformant Having Alanine Producing Ability

The present invention encompasses a transformant obtained by introducing (e) an alanine dehydrogenase gene, into a host bacterium of genus *Hydrogenophilus*. In other words, this transformant has an exogenous alanine dehydrogenase gene. Bacteria of the genus *Hydrogenophilus* produce an amount of alanine required for survival, however, this amount is insufficient for industrial utilization. The transformant of the present invention has been improved in alanine production due to the possession of the exogenous alanine dehydrogenase gene.

Examples of the alanine dehydrogenase gene include (e1) alanine dehydrogenase gene (alaD1) of *Geobacillus stearothermophilus*, alanine dehydrogenase gene (alaD2) of *Geobacillus stearothermophilus*, alanine dehydrogenase gene (alaD1) of *Thermus thermophilus*, and alanine dehydrogenase gene (alaD2) of *Thermus thermophilus*, which are preferable in that they have good alanine production efficiency.

The base sequence of *Geobacillus stearothermophilus* alaD1 is SEQ ID NO: 29, and the base sequence of *Geobacillus stearothermophilus* alaD2 is SEQ ID NO: 30. The base sequence of *Thermus thermophilus* alaD1 is SEQ ID NO: 31, and the base sequence of *Thermus thermophilus* alaD2 is SEQ ID NO: 32.

In particular, alaD2 of *Geobacillus stearothermophilus* (SEQ ID NO: 30) brings about especially high activity of alanine dehydrogenase within bacteria of the genus *Hydrogenophilus*, and thus is preferable.

In the present invention, (e2) DNA which consists of a base sequence having 95% or more, in particular 98% or more, in particular 99% or more identity with SEQ ID NO: 29, 30, 31, or 32, the DNA encoding a polypeptide having alanine dehydrogenase activity, can also be preferably used. In addition, (e3) DNA which hybridizes with a DNA consisting of a base sequence complementary to SEQ ID NO: 29, 30, 31, or 32 under stringent conditions, and which encodes a polypeptide having alanine dehydrogenase activity, can also be preferably used.

In the present invention, (e4) DNA which encodes a polypeptide consisting of an amino acid sequence of SEQ ID NO: 33, 34, 35, or 36 can be preferably used, in terms of good alanine production efficiency. Furthermore, (e5) DNA which encodes a polypeptide consisting of an amino acid sequence having 90% or more, in particular 95% or more, in particular 98% or more, in particular 99% or more identity with SEQ ID NO: 33, 34, 35, or 36, the polypeptide having alanine dehydrogenase activity, and (e6) DNA which encodes a polypeptide consisting of an amino acid sequence having a deletion, substitution, or addition of one or a plurality of amino acids in the amino acid sequence of SEQ ID NO: 33, 34, 35, or 36, the polypeptide having alanine dehydrogenase activity, can also be preferably used.

SEQ ID NO: 33 is the amino acid sequence of alanine dehydrogenase ALAD1 of *Geobacillus stearothermophilus*, and SEQ ID NO: 34 is the amino acid sequence of alanine dehydrogenase ALAD2 of *Geobacillus stearothermophilus*. SEQ ID NO: 35 is the amino acid sequence of alanine dehydrogenase ALAD1 of *Thermus thermophilus*, and SEQ ID NO: 36 is the amino acid sequence of alanine dehydrogenase ALAD2 of *Thermus thermophilus*.

In particular, alanine dehydrogenase ALAD2 of *Geobacillus stearothermophilus* is preferable.

In the present invention, it was found that a modified alanine dehydrogenase in which an N terminus portion of a maltose-binding protein (SEQ ID NO: 37) has been added to the N terminus of an alanine dehydrogenase, expresses a still higher activity in bacteria of the genus *Hydrogenophilus*.

Therefore, the present invention provides a transformant obtained by introducing a DNA encoding the modified alanine dehydrogenase in which the N terminus portion of a maltose-binding protein (SEQ ID NO: 37) has been added to the N terminus of an alanine dehydrogenase (modified alanine dehydrogenase gene), into bacterium of the genus *Hydrogenophilus*. Namely, the present invention provides a transformant obtained by introducing the modified alanine dehydrogenase gene in which a DNA encoding the N terminus portion of a maltose-binding protein (SEQ ID NO: 38) has been added to the 5' end of an alanine dehydrogenase gene, into bacterium of the genus *Hydrogenophilus*.

In this case, the addition is carried out so that the C terminus of the N terminus portion of the maltose-binding protein is linked to the N terminus of the alanine dehydrogenase. Furthermore, the addition is carried out so that the 3' end of the DNA encoding the N terminus portion of the maltose-binding protein is linked to the 5' end of the alanine dehydrogenase gene.

In particular, polypeptides that have the N terminus portion of a maltose-binding protein (SEQ ID NO: 37) added to the N terminus of alanine dehydrogenase ALAD1 or ALAD2 of *Geobacillus stearothermophilus*, or alanine dehydrogenase ALAD1 or ALAD2 of *Thermus thermophilus* are preferable, and polypeptides that have the N terminus portion of the maltose-binding protein (SEQ ID NO: 37) added to the N terminus of alanine dehydrogenase ALAD2 of *Geobacillus stearothermophilus* (SEQ ID NO: 34) is more preferable.

In detail, (e7) DNA encoding a modified amino acid sequence in which an amino acid sequence of the N terminus portion of the maltose-binding protein (SEQ ID NO: 37) has been added to the N terminus of the amino acid sequence of SEQ ID NO: 33, 34, 35, or 36, can be preferably used for the transformation of bacteria of the genus *Hydrogenophilus*. The amino acid sequence of the modified alanine dehydrogenase in which the N terminus portion of the maltose-binding protein (SEQ ID NO: 37) has been added to the N terminus of alanine dehydrogenase ALAD2 of *Geobacillus stearothermophilus* (SEQ ID NO: 34) is SEQ ID NO: 39.

Furthermore, (e8) DNA which encodes a polypeptide consisting of an amino acid sequence in which the amino acid sequence of the N terminus portion of a maltose-binding protein (SEQ ID NO: 37) has been added to the N terminus of an amino acid sequence having 90% or more, in particular 95% or more, in particular 98% or more, in particular 99% or more identity with SEQ ID NO: 33, 34, 35, or 36, the polypeptide having alanine dehydrogenase activity, and (e9) DNA which encodes a polypeptide consisting of an amino acid sequence in which the amino acid sequence of the N terminus portion of the maltose-binding protein (SEQ ID NO: 37) has been added to the N terminus of an amino acid sequence having a deletion, substitution, or addition of one or a plurality of amino acids in the amino acid sequence of SEQ ID NO: 33, 34, 35, or 36, the polypeptide having alanine dehydrogenase activity, can also be used.

(e10) DNA which consists of a base sequence in which the base sequence encoding the N terminus portion of the maltose-binding protein (SEQ ID NO: 38) has been added to the 5' end of the base sequence of SEQ ID NO: 29, 30, 31, or 32, can be used as well. In particular, DNA (SEQ ID NO: 40) which consists of a base sequence in which the base sequence of the N terminus portion of the maltose-binding protein (SEQ ID NO: 38) has been added to the 5' end of the base sequence of SEQ ID NO: 30, which is a base sequence of *Geobacillus stearothermophilus* alaD2, is preferable.

Furthermore, (e11) DNA which consists of a base sequence in which the base sequence encoding the N terminus portion of the maltose-binding protein (SEQ ID NO: 38) has been added to the 5' end of a base sequence having 90% or more, in particular 95% or more, in particular 98% or more, in particular 99% or more identity with SEQ ID NO: 29, 30, 31, or 32, the DNA encoding a polypeptide having alanine dehydrogenase activity, and (e12) DNA which consists of a base sequence in which the base sequence encoding the N terminus portion of the maltose-binding protein (SEQ ID NO: 38) has been added to the 5' end of a base sequence of a DNA which hybridizes with a DNA consisting of a base sequence complementary to SEQ ID NO: 29, 30, 31, or 32 under stringent conditions, and which encodes a polypeptide having alanine dehydrogenase activity, can be used as well.

The present invention encompasses a modified alanine dehydrogenase gene in which the polynucleotide (SEQ ID NO: 38) encoding the N terminus portion of the maltose-binding protein (SEQ ID NO: 37) has been added to the 5' end of an alanine dehydrogenase gene. Specific examples of the modified alanine dehydrogenase gene and preferable modified alanine dehydrogenase genes are as described with regard to the modified alanine dehydrogenase gene that is used for the transformation of bacteria of the genus *Hydrogenophilus*. The present invention also encompasses a vector comprising this modified alanine dehydrogenase gene (in particular, a vector that functions within bacteria of the genus *Hydrogenophilus*).

This modified alanine dehydrogenase gene and the vector comprising the gene can be preferably used for alanine production within bacteria of the genus *Hydrogenophilus*.

The present invention encompasses a modified alanine dehydrogenase in which the N terminus portion of the maltose-binding protein (SEQ ID NO: 37) has been added to the N terminus of an alanine dehydrogenase. Specific examples of the modified alanine dehydrogenase and preferable modified alanine dehydrogenases are as described with regard to the modified alanine dehydrogenase which is encoded by the modified alanine dehydrogenase gene that is used for the transformation of bacteria of the genus *Hydrogenophilus*.

This modified alanine dehydrogenase can be preferably used for alanine production within bacteria of the genus *Hydrogenophilus*, or can be used for alanine production by enzyme reaction.

In the present invention, in order to confirm that a polypeptide has an alanine dehydrogenase activity, a test polypeptide is reacted with pyruvic acid and ammonium chloride under the coexistence of NADH, and decrease in absorbance at 340 nm is detected. Alanine dehydrogenase produces alanine from pyruvic acid and ammonia, which is accompanied by the conversion of NADH to NAD, and thus decrease in the amount of NADH is detected using decrease in absorbance at 340 nm as an index. Specifically, the method described in item "Examples" is carried out. If the test polypeptide reduces the absorbance at 340 nm even by a slight degree, the polypeptide is determined to have alanine dehydrogenase activity.

In the present invention, a "homologue" of a certain DNA which encodes a polypeptide having a certain activity means a DNA which has a base sequence similar to the certain DNA (in particular, consisting of a base sequence having 90% or more identity with the base sequence of the certain DNA), and which encodes a polypeptide having the certain activity, or means a DNA which hybridizes with a DNA consisting of a base sequence complementary to the base sequence of the certain DNA under stringent conditions, and which encodes a polypeptide having the certain activity.

In the present invention, a "homologue" of a certain polypeptide having a certain activity means a polypeptide which has an amino acid sequence similar to the certain polypeptide (in particular, consisting of an amino acid sequence having 90% or more identity with the amino acid sequence of the certain polypeptide), and which has the certain activity, as well as a polypeptide which consists of an amino acid sequence in which one or a plurality of amino acids have been deleted, substituted, or added in the amino acid sequence of the certain polypeptide, and which has the certain activity.

(4) Methods for Producing Transformants

Next, methods for obtaining transformants by introducing the above-described genes for the production of isobutanol, the above-described genes for the production of ethanol or the above-described genes for the production of alanine, into bacteria of the genus *Hydrogenophilus* are explained.

Host

Examples of bacteria of the genus *Hydrogenophilus* include *Hydrogenophilus thermoluteolus, Hydrogenophilus halorhabdus, Hydrogenophilus denitrificans, Hydrogenophilus hirschii, Hydrogenophilus islandicus,* and strain Mar3 of bacteria of the genus *Hydrogenophilus* (*Hydrogenophilus* sp. Mar3). In particular, *Hydrogenophilus thermoluteolus* is preferable in that it possesses not only top-level growth rate but also top-level carbon dioxide fixation ability among carbon dioxide fixing microorganisms.

Bacteria of the genus *Hydrogenophilus* can be easily separated from everywhere on the earth. A preferable strain of *Hydrogenophilus thermoluteolus* include strain TH-1 (NBRC 14978). *Hydrogenophilus thermoluteolus* strain TH-1 (NBRC 14978) exhibits a top growth rate among carbon dioxide fixing microorganisms (Agricultural and Biological Chemistry, 41, 685-690 (1977)). *Hydrogenophilus thermoluteolus* strain NBRC 14978 is internationally deposited under the Budapest Treaty, and available to the public.

Transformation

Plasmid vectors for introducing the above-described DNAs into a host should contain a DNA which controls the autonomous replication function within bacteria of the genus *Hydrogenophilus*, and examples include broad-host-range vectors pRK415 (GenBank: EF437940.1), pBHR1 (GenBank: Y14439.1) pMMB67EH (ATCC 37622), pCAR1 (NCBI Reference Sequence: NC 004444.1), pC194 (NCBI Reference Sequence: NC_002013.1), pK18mobsacB (GenBank: FJ437239.1), pUB110 (NCBI Reference Sequence: NC_001384.1), and the like.

Examples of a preferable promoter include tac promoter, lac promoter, trc promoter, or each of promoters OXB1 and OXB11 to OXB20 from Oxford Genetics Ltd. Examples of a preferable terminator include rrnB T1T2 terminator of *Escherichia coli* rRNA operon, bacteriophage λt0 transcription terminator, and the like.

Transformation can be carried out by publicly known methods such as calcium chloride method, calcium phosphate method, DEAE-dextran transfection method, and electric pulse method.

Bacteria of the genus *Hydrogenophilus* grow under autotrophic conditions. However, since they can grow under heterotrophic conditions as well, the culture medium which is used to culture a host or transformant of a bacterium of the genus *Hydrogenophilus* can either be an inorganic culture medium or an organic culture medium. An organic culture medium comprising sugar, organic acids, amino acid, and the like can be used. The pH of the culture medium can be adjusted to approximately 6.2 to 8.

In any of the cases, culture can be carried out while supplying a mixed gas containing hydrogen, oxygen, and carbon dioxide, and preferably a mixed gas consisting of hydrogen, oxygen, and carbon dioxide. When using an organic culture medium, a mixed gas containing hydrogen, oxygen, and carbon dioxide, for example the air, can be used for aeration. When carbon dioxide gas is not supplied, a culture medium containing a carbonate as a carbon source can be used. Mixed gas can be entrapped within or continuously supplied into an airtight culture container, and can be dissolved into the culture medium by means of shaking culture. Alternatively, the culture container can be an airtight or open type, and mixed gas can be dissolved into the culture medium by bubbling.

The volume ratio of hydrogen, oxygen, and carbon dioxide within the supplied gas (hydrogen:oxygen:carbon dioxide) is preferably 1.75 to 7.5:1:0.25 to 3, more preferably 5 to 7.5:1:1 to 2, and further more preferably 6.25 to 7.5:1:1.5. Bacteria of the genus *Hydrogenophilus* are thermophilic bacteria, and thus the culture temperature is preferably 35 to 55° C., more preferably 37 to 52° C., and further more preferably 50 to 52° C.

(5) Method for Producing Isobutanol, Ethanol, or Alanine

When producing isobutanol, ethanol, or alanine using the transformant of bacterium of the genus *Hydrogenophilus* genus described above, the transformant can be cultured using an inorganic or organic culture medium while supplying a mixed gas containing hydrogen, oxygen, and carbon dioxide.

The supplied gas is preferably a mixed gas consisting of hydrogen, oxygen, and carbon dioxide. However, different kinds of gas can be mixed within, to the extent that isobutanol, ethanol, or alanine can be produced efficiently.

Bacteria of the genus *Hydrogenophilus* can grow using hydrogen as a source of energy and using carbon dioxide as a sole carbon source, and thus, carbon dioxide can be fixed efficiently particularly by producing the above-described compounds by using substantially only carbon dioxide (in particular, by using only carbon dioxide) as a carbon source. Therefore, using an inorganic culture medium that does not contain carbon sources such as organic substances and carbonates, namely, carrying out culture using substantially only carbon dioxide (in particular, using only carbon dioxide) as a carbon source is preferable. "Using substantially only carbon dioxide as a carbon source" encompasses cases in which an unavoidable amount of other carbon sources are mixed within. Furthermore, a culture medium containing organic substances such as sugar, organic acids, and amino acids, as well as carbonates, can also be used without supplying carbon dioxide.

The pH of the culture medium is preferably 6.2 to 8, more preferably 6.4 to 7.4, and further more preferably 6.6 to 7. When the pH is within this range, bacteria grow well and mixed gas dissolves well into the culture medium, and the target compound can be produced efficiently.

When batch culture is utilized, mixed gas can be entrapped within an airtight culture container and static culture or shaking culture can be carried out. When continuous culture is utilized, mixed gas can be continuously supplied into an airtight culture container and shaking culture can be carried out, or the transformant can be cultured using an airtight culture container while inducing mixed gas into the culture medium by bubbling. Shaking culture is preferable in that better dissolution of mixed gas into the culture medium can be achieved.

The volume ratio of hydrogen, oxygen, and carbon dioxide (hydrogen:oxygen:carbon dioxide) in the supplied gas is preferably 1.75 to 7.5:1:0.25 to 3, more preferably 5 to 7.5:1:1 to 2, and further more preferably 6.25 to 7.5:1:1.5. When the volume ratio is within this range, bacteria grow well, and the target compound can be produced efficiently.

The supply rate of mixed gas or raw material gas can be 10.5 to 60 L/hour, in particular 10.5 to 40 L/hour, in particular 10.5 to 21 L/hour, per 1 L of culture medium. When the supply rate is within this range, transformants grow well and the target compound can be produced efficiently, and the amount of wasted mixed gas can be reduced.

The culture temperature is preferably 35 to 55° C., more preferably 37 to 52° C., and further more preferably 50 to 52° C. When the temperature is within this range, transformants grow well, and the target compound can be produced efficiently.

Recovery of Target Compound

The target compound isobutanol, ethanol, or alanine is produced in the reaction solution by culturing in the above-described manner. Collecting the reaction solution will enable the recovery of the target compound, however, the target compound can furthermore be separated from the reaction solution by publicly known methods. Such publicly known methods with regard to ethanol and isobutanol include fractional distillation, extraction, and separation through ultrasonic atomization, and those with regard to alanine include various kinds of chromatography, and crystallization.

Examples (1) Construction of a Plasmid Vector

The method for constructing a plasmid vector that was commonly used to introduce genes for conferring isobutanol producing ability, genes for conferring ethanol producing ability, and genes for conferring alanine producing ability, is described below.

First, a broad-host-range vector pRK415 (GenBank: EF437940.1) (Gene, 70, 191-197 (1998)) was used as a template and PCR was performed. In order to amplify the DNA fragment of the plasmid region excluding the tetracycline gene region, a primer pair described below was synthesized and used. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of pRK415 Plasmid Sequence

```
(a-1)
                                       (SEQ ID NO: 42)
5'-CGTGGCCAACTAGGCCCAGCCAGATACTCCCGATC-3'

(b-1)
                                       (SEQ ID NO: 43)
5'-TGAGGCCTCATTGGCCGGAGCGCAACCCACTCACT-3'
```

A SfiI restriction site has been added to primers (a-1) and (b-1).

Plasmid pK18mobsacB (GenBank: FJ437239.1) (Gene, 145, 69-73 (1994)), which contains a neomycin/kanamycin resistance gene (hereinafter, the gene may be referred to as "nptII"), was used as a template and PCR was performed according to a conventional method. In the PCR, a primer pair described below was synthesized and used in order to amplify the DNA fragment containing the nptII gene sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of nptII Gene Sequence

```
(a-2)
                                       (SEQ ID NO: 44)
5'-ctgGGCCTAGTTGGCCacgtagaaagccagtccgc-3'

(b-2)
                                       (SEQ ID NO: 45)
5'-tccGGCCAATGAGGCCtcagaagaactcgtcaaga-3'
```

A SfiI restriction site has been added to primers (a-2) and (b-2).

The reaction solutions that were produced by each of the above-described PCR were subjected to electrophoresis using a 1% agarose gel, and as a result, a DNA fragment of approximately 8.7-kb was detected when pRK415 plasmid was used as a template, and a DNA fragment of approximately 1.1-kb was detected when nptII gene was used as a template.

Thus prepared DNA fragments were each cleaved by restriction enzyme SfiI, and reacted with a T4 DNA Ligase (manufactured by Takara Bio Inc.) to obtain a ligation solution. The obtained ligation solution was used to transform *Escherichia coli* JM109 by calcium chloride method (Journal of Molecular Biology, 53, 159-162 (1970)), and the transformants were applied onto LB agar media containing kanamycin. Viable strains on the culture media were cultured in a liquid culture medium by a conventional method, and plasmid DNA was extracted from the obtained culture solution. This plasmid DNA was cleaved by using restriction enzyme SfiI, and the inserted fragment was confirmed. As a result, a DNA fragment of the nptII gene sequence which was approximately 1.1-kb was observed in addition to DNA fragments of approximately 2.0-kb, 3.0-kb and 3.7-kb, which were derived from the pRK415 plasmid.

The constructed plasmid was named pCYK01.

(2) Construction of Cloning Vector Used for Gene Expression (2-1) Preparation of DNA Fragment of λt0 Terminator Sequence A primer pair described below was synthesized and used in PCR in order to prepare a DNA having λt0 terminator sequence. PCR was performed using "DNA thermal cycler" manufactured by Life Technologies Inc., and using KOD FX Neo (manufactured by Toyobo Co., Ltd.) as a reaction reagent. No template DNA was included since extension was carried out using each primer as the other's template.

Primers for the Preparation of λt0 Terminator Sequence

```
(a-3)
                                       (SEQ ID NO: 46)
5'-GCATTAATccttggactcctgttgatagatccagtaatgacctcaga actccatctggatttgttcagaacgctcggttgccg-3'

(b-3)
                                       (SEQ ID NO: 47)
5'-caccgtgcagtcgatgGATctggattctcaccaataaaaaacgcccg gcggcaaccgagcgttctgaacaaatccagatggag-3'
```

The base sequences of the 3' ends of primers (a-3) and (b-3) are complementary to each other.

The produced reaction solution was subjected to electrophoresis using a 1% agarose gel, and as a result, a DNA fragment of approximately 0.13-kb, which corresponds to the λt0 terminator sequence, was detected.

(2-2) Preparation of a DNA Fragment of Tac Promoter Sequence

PCR was performed using plasmid pMAL-c5X (manufactured by New England Biolabs Inc.) containing a tac promoter, as a template. In the PCR, a primer pair described below was synthesized and used in order to amplify tac promoter sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of Tac Promoter Sequence (a-4)
(SEQ ID NO: 48)
5'-TTATTGGTGAGAATCCAGATCCATCGACTGCACGGTGCACCAATGCTTCT-3'

(b-4)
(SEQ ID NO: 49)
5-gcaagcttggagtgatcatcgtATGCATATGCGTTTCTCCTCCAGATCCctgtttcctgtgtgaaattgt-3'

The produced reaction solution was subjected to electrophoresis using a 1% agarose gel, and as a result, a DNA fragment of approximately 0.3-kb, which corresponds to tac promoter sequence, was detected.

(2-3) Introduction of λt0 Terminator and Tac Promoter Sequences

The DNA fragments that were prepared in the above-described (2-1) and (2-2) were cut out from the agarose gel, and DNA was recovered from the gel by freezing and melting the gel. The recovered DNA fragments corresponding to λt0 terminator sequence and the tac promoter sequence were mixed and used as templates, and overlap extension PCR was performed. In the overlap extension PCR, a combination of the above-described primers (a-3) and (b-4) was used in order to prepare a DNA in which the tac promoter is linked downstream of λt0 terminator. The base sequences of the 5' ends of the primers (b-3) and (a-4), which were used in amplifying the template DNA fragments, are complementary with each other. PshBI and HindIII restriction sites have been added to primers (a-3) and (b-4), respectively.

The produced reaction solution was subjected to electrophoresis using a 1% agarose gel, and as a result, a DNA fragment of approximately 0.4-kb, which corresponds to the DNA in which the tac promoter is linked downstream of λt0 terminator, was detected.

The approximately 0.4-kb DNA fragment that was amplified by PCR, in which the tac promoter is linked downstream of the λt0 terminator, and the above-mentioned approximately 9.8-kb DNA fragment of cloning vector pCYK01, were cleaved by the restriction enzymes PshBI and HindIII. The cleaved DNA fragments were linked to each other using a T4 DNA Ligase (manufactured by Takara Bio Inc.).

The obtained ligation solution was used to transform *Escherichia coli* JM109 by calcium chloride method, and the transformants were applied onto LB agar media containing kanamycin. Viable strains on the culture media were cultured in a liquid culture medium by a conventional method, and plasmid DNA was extracted from the obtained culture solution. This plasmid DNA was cleaved by using restriction enzymes PshBI and HindIII, and the inserted fragment was confirmed. As a result, a DNA fragment of approximately 0.4-kb, in which tac promoter is linked downstream of λt0 terminator, was observed in addition to a DNA fragment of approximately 9.6-kb from plasmid pCYK01.

(2-4) Introduction of rrnB T1T2 Bidirectional Terminator (Hereinafter, May be Referred to as "rrnB Terminator")

PCR was performed using plasmid pMAL-c5X (manufactured by New England Biolabs Inc.) containing rrnB terminator sequence as a template. In the PCR, a primer pair described below was synthesized and used in order to amplify rrnB terminator sequence. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of rrnB Terminator Sequence (a-5)
(SEQ ID NO: 50)
5'-ctcgaattcactggccgtcgttttacaacgtcgtg-3'

(b-5)
(SEQ ID NO: 51)
5'-CGCAATTGAGTTTGTAGAAACGCAAAAAGGCCATC-3'

EcoRI and MunI restriction sites have been added to primers (a-5) and (b-5), respectively.

The produced reaction solution was subjected to electrophoresis using a 1% agarose gel, and as a result, a DNA fragment of approximately 0.6-kb, which corresponds to rrnB terminator sequence, was detected.

The approximately 0.6-kb DNA fragment containing rrnB terminator sequence, which was amplified by the above-described PCR, was cleaved by restriction enzymes EcoRI and MunI, and the approximately 10.0-kb DNA fragment of the plasmid that was constructed in the above-described (2-3) was cleaved using restriction enzyme EcoRI. The cleaved DNA fragments were linked to each other using a T4 DNA Ligase (manufactured by Takara Bio Inc.).

The obtained ligation solution was used to transform *Escherichia coli* JM109 by calcium chloride method, and the obtained transformants were applied onto LB agar media containing kanamycin. Viable strains on the culture media were cultured in a liquid culture medium by a conventional method, and plasmid DNA was extracted from the obtained culture solution. This plasmid was cleaved by using restriction enzymes EcoRI and MunI, and the inserted fragment was confirmed. As a result, a DNA fragment of approximately 0.6-kb which corresponds to rrnB terminator sequence was observed in addition to a DNA fragment of approximately 10.0-kb from the above-described plasmid of (2-3).

The constructed cloning vector for gene expression was named pCYK21.

(3) Transformant Having Isobutanol Producing Ability (3-1) Codon Optimization of the 2-Keto-Acid Decarboxylase Gene of *Lactococcus lactis*

Codon usage of kivD gene encoding the 2-keto-acid decarboxylase of *Lactococcus lactis* was optimized according to the codon usage frequency of *Hydrogenophilus thermoluteolus* strain TH-1 (NBRC 14978), and the DNA fragment of the optimized base sequence (SEQ ID NO: 1) was synthesized by GenScript Japan Inc.

The approximately 1.7-kb DNA fragment of the codon-optimized gene that was synthesized, and the above-mentioned DNA fragment of approximately 10.6-kb from cloning vector pCYK21 were each cleaved by using restriction enzymes NdeI and HindIII. The cleaved DNA fragments were linked to each other using a T4 DNA Ligase (manufactured by Takara Bio Inc.).

The obtained ligation solution was used to transform *Hydrogenophilus thermoluteolus* strain TH-1 (NBRC 14978) by electric pulse method (electroporation method), and the transformants were applied onto A-solid medium [(NH$_4$)$_2$SO$_4$ 3.0 g, KH$_2$PO$_4$ 1.0 g, K$_2$HPO$_4$ 2.0 g, NaCl 0.25 g, FeSO$_4$·7H$_2$O 0.014 g, MgSO$_4$·7H$_2$O 0.5 g, CaCl$_2$ 0.03 g, MoO$_3$ 4.0 mg, ZnSO$_4$·7H$_2$O 28 mg, CuSO$_4$·5H$_2$O 2.0 mg, H$_3$BO$_3$ 4.0 mg, MnSO$_4$·5H$_2$O 4.0 mg, CoCl$_2$·6H$_2$O 4.0 mg, agar 15 g were dissolved in 1 L of distilled water (pH 7.0)] containing kanamycin at 50 µg/ml, and incubated at 50° C. for 60 hours in a chamber that was filled with a mixed gas of H$_2$:O$_2$:CO$_2$=7.5:1:1.5.

Viable strains on the A-solid medium were inoculated using a platinum loop into a test tube containing 5 ml of A-liquid medium [(NH$_4$)$_2$SO$_4$ 3.0 g, KH$_2$PO$_4$ 1.0 g, K$_2$HPO$_4$ 2.0 g, NaCl 0.25 g, FeSO$_4$·7H$_2$O 0.014 g, MgSO$_4$·7H$_2$O 0.5 g, CaCl$_2$ 0.03 g, MoO$_3$ 4.0 mg, ZnSO$_4$·7H$_2$O 28 mg, CuSO$_4$·5H$_2$O 2.0 mg, H$_3$BO$_3$ 4.0 mg, MnSO$_4$·5H$_2$O 4.0 mg, CoCl$_2$·6H$_2$O 4.0 mg were dissolved in 1 L of distilled water (pH 7.0)] containing kanamycin at 50 µg/ml. The test tubes were filled with a mixed gas of H$_2$:O$_2$:CO$_2$=7.5:1:1.5, and subjected to shaking culture at 50° C., and plasmid DNA was extracted from the obtained culture solution. The plasmid was cleaved using restriction enzymes NdeI and HindIII, and the inserted fragment was confirmed. As a result, a DNA fragment of approximately 1.7-kb of the codon-optimized gene was observed in addition to a DNA fragment of approximately 10.6-kb from plasmid pCYK21.

The plasmid containing the codon-optimized *Lactococcus lactis* kivD gene was named pC-opt-kivD. The recombinant strain of *Hydrogenophilus thermoluteolus* which possesses pC-opt-kivD was named strain KDC01.

(3-2) Cloning of 2-Keto-Acid Decarboxylase Gene for Comparison Examples

Genomic DNAs were extracted from *Lactococcus lactis* NBRC 100933, *Bacillus subtilis* NBRC 13719, *Geobacillus thermoglucosidasius* NBRC 107763, *Geobacillus thermodenitrificans* ATCC 29492, and *Klebsiella pneumoniae* NBRC 14940 according to a conventional method.

A DNA fragment containing 2-keto-acid decarboxylase kivD gene of *Lactococcus lactis*, a DNA fragment containing acetolactate synthase alsS gene of *Bacillus subtilis*, the acetolactate synthase having 2-keto-acid decarboxylase activity, a DNA fragment containing acetolactate synthase Geoth_3495 gene of *Geobacillus thermoglucosidasius*, the acetolactate synthase having a 2-keto-acid decarboxylase activity, a DNA fragment containing acetolactate synthase Gtng_0348 gene of *Geobacillus thermodenitrificans*, the acetolactate synthase having a 2-keto-acid decarboxylase activity, and a DNA fragment containing indolepyruvate decarboxylase ipdC gene of *Klebsiella pneumoniae*, the indolepyruvate decarboxylase having a 2-keto-acid decarboxylase activity were amplified by PCR method using the 5-kind genomic DNAs described above, respectively.

The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of *Lactococcus lactis* kivD Gene (a-6)
(SEQ ID NO: 52)
5'-GCACATATGTATACAGTAGGAGATTACCTATTAGA-3'

(b-6)
(SEQ ID NO: 53)
5'-GCAGGATCCTTATGATTTATTTTGTTCAGCAAATA-3'

An NdeI restriction site has been added to primer (a-6), and a BamHI restriction site has been added to primer (b-6).

Primers for the Amplification of *Bacillus subtilis* alsS Gene (a-7)
(SEQ ID NO: 54)
5'-GCACATATGACAAAAGCAACAAAAGAACAAAAATC-3'

(b-7)
(SEQ ID NO: 55)
5'-GCAGGATCCTAGAGAGCTTTCGTTTTCATGAGTTC-3'

An NdeI restriction site has been added to primer (a-7), and a BamHI restriction site has been added to primer (b-7).

Primers for the Amplification of *Geobacillus thermoglucosidasius* Geoth_3495 Gene (a-8)
(SEQ ID NO: 56)
5'-CGAGTCCATATGAAACAGACTATCCGCAATATCAG-3'

(b-8)
(SEQ ID NO: 57)
5'-GCAGGATCCTTACCGAGAATTCGAGCGCTTTCGCA-3'

An NdeI restriction site has been added to primer (a-8), and a BamHI restriction site has been added to primer (b-8).

Primers for the Amplification of *Geobacillus thermodenitrificans* Gtng_0348 Gene (a-9)
(SEQ ID NO: 58)
5'-CGAGTCCATATGAAAAAGCGGGTGATGCGTGGCCT-3'

(b-9)
(SEQ ID NO: 59)
5'-GCAGGATCCTCATCTGTCTGACAGTCTCATCGTCA-3'

An NdeI restriction site has been added to primer (a-9), and a BamHI restriction site has been added to primer (b-9).

Primers for the Amplification of *Klebsiella pneumoniae* ipdC Gene (a-10)
(SEQ ID NO: 60)
5'-CGAGTCCATATGCAACCGACCTACACTATTGGGGA-3'

(b-10)
(SEQ ID NO: 61)
5'-CGCGGATCCTTAAACGCGGCTGTTTCGCTCCTCAA-3'

An NdeI restriction site has been added to primer (a-10), and a BamHI restriction site has been added to primer (b-10).

The produced reaction solutions were subjected to electrophoresis using a 1% agarose gel, and DNA fragments of approximately 1.7-kb were detected with regard to each of *Lactococcus lactis* kivD gene, *Bacillus subtilis* alsS gene, *Geobacillus thermoglucosidasius* Geoth_3495 gene, *Geobacillus thermodenitrificans* Gtng_0348 gene, and *Klebsiella pneumoniae* ipdC gene.

The approximately 1.7-kb DNA fragments, each containing Lactococcus lactis kivD gene, Bacillus subtilis alsS gene, Geobacillus thermoglucosidasius Geoth_3495 gene, Geobacillus thermodenitrificans Gtng_0348 gene, or Klebsiella pneumoniae ipdC gene, which were amplified by the above-mentioned PCR were cleaved by using restriction enzymes NdeI and HindIII. The above-described approximately 10.6-kb DNA fragment of cloning vector pCYK21 was also cleaved by using restriction enzymes NdeI and HindIII. Each of the 5 cleaved 1.7-kb DNA fragments and the 10.6-kb DNA fragment were linked to each other using a T4 DNA Ligase (manufactured by Takara Bio Inc.).

The obtained ligation solutions were used to transform Hydrogenophilus thermoluteolus strain TH-1 (NBRC 14978) by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C., and plasmid DNAs were extracted from the culture solution. The plasmids were cleaved by using restriction enzymes NdeI and BamHI, and the inserted fragments were confirmed. As a result, DNA fragments each of approximately 1.7-kb in length, which were from Lactococcus lactis kivD gene, Bacillus subtilis alsS gene, Geobacillus thermoglucosidasius Geoth_3495 gene, Geobacillus thermodenitrificans Gtng_0348 gene, and Klebsiella pneumoniae ipdC gene in addition to an approximately 10.6-kb DNA fragment of plasmid pCYK21 were observed.

The plasmid containing Lactococcus lactis kivD gene was named pC-Lla-kivD, the plasmid containing Bacillus subtilis alsS gene was named pC-Bsu-alsS, the plasmid containing Geobacillus thermoglucosidasius Geoth_3495 gene was named pC-Gtg-3495, the plasmid containing Geobacillus thermodenitrificans Gtng_0348 gene was named pC-Gtd-0348, and the plasmid containing Klebsiella pneumoniae ipdC gene was named pC-Kpn-ipdC.

(3-3) Cloning of Alcohol Dehydrogenase Gene

Genomic DNAs were extracted from Klebsiella pneumoniae NBRC 14940, Geobacillus thermocatenulatus NBRC 15316, and Geobacillus thermoglucosidasius NBRC 107763 according to a conventional method.

The 3 genomic DNAs described above were each used as templates to amplify a DNA fragment containing alcohol dehydrogenase gene adhP of Klebsiella pneumoniae, a DNA fragment containing alcohol dehydrogenase gene adhP of Geobacillus thermocatenulatus, a DNA fragment containing alcohol dehydrogenase gene adhP of Geobacillus thermoglucosidasius, and a DNA fragment containing alcohol dehydrogenase gene adhA of Geobacillus thermoglucosidasius, respectively, by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of Klebsiella pneumoniae adhP Gene (a-11)
(SEQ ID NO: 62)
5'-CGAGTCCATATGAAGGCAGCTGTTGTTACCCACGA-3'

(b-11)
(SEQ ID NO: 63)
5'-CGCGAATTCTTAGCTACGCAGATCGATAACCATAC-3'

An NdeI restriction site has been added to primer (a-11), and an EcoRI restriction site has been added to primer (b-11).
Primers for the Amplification of Geobacillus thermocatenulatus adhP Gene (a-12)
(SEQ ID NO: 64)
5'-CGAGTCCATATGAAAGCCGCCGTTGTTCACAAATT-3'

(b-12)
(SEQ ID NO: 65)
5'-GCAGGATCCTTACATTGTTAAAACAATGCGGCCAT-3'

An NdeI restriction site has been added to primer (a-12), and a BamHI restriction site has been added to primer (b-12).
Primers for the Amplification of Geobacillus thermoglucosidasius adhP Gene (a-13)
(SEQ ID NO: 66)
5'-CGAGTCCATATGAAAGCGGCAGTTGTCAACGATTT-3'

(b-13)
(SEQ ID NO: 67)
5'-CGCGAATTCTTAACGGTTGACACCGATGGTTAAAA-3'

An NdeI restriction site has been added to primer (a-13), and an EcoRI restriction site has been added to primer (b-13).
Primers for the Amplification of Geobacillus thermoglucosidasius adhA Gene (a-14)
(SEQ ID NO: 68)
5'-CGAGTCCATATGAAAGCACTTACATACCTAGGGCC-3'

(b-14)
(SEQ ID NO: 69)
5'-GCAGGATCCTTAACTGTTGGAAATAATGACTTTTA-3'

An NdeI restriction site has been added to primer (a-14), and a BamHI restriction site has been added to primer (b-14).

The produced reaction solutions were subjected to electrophoresis using a 1% agarose gel, and DNA fragments of approximately 1.0-kb were detected with regard to each of Klebsiella pneumoniae adhP gene, Geobacillus thermocatenulatus adhP gene, Geobacillus thermoglucosidasius adhP gene, and Geobacillus thermoglucosidasius adhA gene.

The approximately 1.0-kb DNA fragments containing each of Geobacillus thermocatenulatus adhP gene and Geobacillus thermoglucosidasius adhA gene, that were amplified by the above-described PCR, were cleaved by using restriction enzymes NdeI and BamHI. The above-mentioned approximately 10.6-kb DNA fragment of cloning vector pCYK21 was also cleaved by using restriction enzymes NdeI and BamHI. Each of the cleaved 1.0-kb DNA fragments and the 10.6-kb DNA fragment were linked to each other using a T4 DNA Ligase (manufactured by Takara Bio Inc.).

The approximately 1.0-kb DNA fragments containing each of *Klebsiella pneumoniae* adhP gene and *Geobacillus thermoglucosidasius* adhP gene, that were amplified by PCR, were cleaved by using restriction enzymes NdeI and EcoRI. The above-mentioned approximately 10.6-kb DNA fragment of cloning vector pCYK21 was also cleaved by using restriction enzymes NdeI and EcoRI. Each of the cleaved 1.0-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7\ 0.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C., and plasmid DNAs were extracted from the culture solution. The plasmids were cleaved using restriction enzymes NdeI and BamHI, or NdeI and EcoRI, and the inserted fragments were confirmed. As a result, fragments of approximately 1.0-kb in length which were each inserted fragments of *Klebsiella pneumoniae* adhP gene, *Geobacillus thermocatenulatus* adhP gene, *Geobacillus thermoglucosidasius* adhP gene, and *Geobacillus thermoglucosidasius* adhA gene, in addition to an approximately 10.6-kb DNA fragment of plasmid pCYK21 were observed.

The plasmid containing *Klebsiella pneumoniae* adhP gene was named pC-Kpn-adhP, the plasmid containing *Geobacillus thermocatenulatus* adhP gene was named pC-Gtc-adhP, the plasmid containing *Geobacillus thermoglucosidasius* adhP gene was named pC-Gtg-adhP, and the plasmid containing *Geobacillus thermoglucosidasius* adhA gene was named pC-Gtg-adhA.

The plasmids possessed by the recombinant strains of *Hydrogenophilus thermoluteolus* are shown in Table 1.

TABLE 1

| Strain | Plasmid | Transgene |
| --- | --- | --- |
| KDC01 | pC-opt-kivD | Codon-optimized kivD (*Lactococcus lactis*) |
| KDC02 | pC-Lla-kivD | kivD (*Lactococcus lactis*) |
| KDC03 | pC-Bsu-alsS | alsS (*Bacillus subtilis*) |
| KDC04 | pC-Gtg-3495 | Geoth_3495 (*Geobacillus thermoglucosidasius*) |
| KDC05 | pC-Gtd-0348 | Gtng_0348 (*Geobacillus thermodenitrificans*) |
| KDC06 | pC-Kpn-ipdC | ipdc (*Klebsiella pneumoniae*) |
| ADH01 | pC-Kpn-adhP | adhP (*Klebsiella pneumoniae*) |
| ADH02 | pC-Gtc-adhP | adhP (*Geobacillus thermocatenulatus*) |
| ADH03 | pC-Gtg-adhP | adhP (*Geobacillus thermoglucosidasius*) |
| ADH04 | pC-Gtg-adhA | adhA (*Geobacillus thermoglucosidasius*) |

(3-4) Confirmation of Transgene Expression in *Hydrogenophilus Thermoluteolus* Strain into which Isobutanol Producing Gene has been Introduced Measurement of 2-Keto-Acid Decarboxylase Activity Each 2-keto-acid decarboxylase gene-introduced strain that was obtained as described above, was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells thus cultured and proliferated were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure 2-keto-acid decarboxylase activity by the following method. Crude enzyme solution, 50 mM Tris-HCl (pH 6.8), 2.5 mM $MgSO_4$, 0.2 mM thiamine pyrophosphate (TPP), 3.0 mM NADH, 30 mM 2-ketoisovalerate, and 0.5 U/ml horse-derived alcohol dehydrogenase (Sigma-Aldrich Japan G.K.) were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of isobutyraldehyde per minute was defined as 1 U (Unit).

As a result, 0.65 U/mg of 2-keto-acid decarboxylase activity of interest was detected in strain KDC01, into which a codon-optimized kivD of *Lactococcus lactis* was introduced.

On the other hand, no 2-keto-acid decarboxylase activity was observed in strain KDC02 into which natural form kivD of *Lactococcus lactis* was introduced, strain KDC03 into which *Bacillus subtilis* alsS was introduced, strain KDC04 into which *Geobacillus thermoglucosidasius* Geoth_3495 was introduced, strain KDC05 into which *Geobacillus thermodenitrificans* Gtng_0348 was introduced, and strain KDC06 into which *Klebsiella pneumoniae* ipdC was introduced.

No 2-keto-acid decarboxylase activity was observed as a result of conducting the same experiment with regard to *Hydrogenophilus thermoluteolus* strain TH-1 into which an empty vector (pCYK21) was introduced.

Measurement of Activity of an Alcohol Dehydrogenase that Uses Isobutyraldehyde as a Substrate Each alcohol dehydrogenase gene-introduced strain of *Hydrogenophilus thermoluteolus* that was obtained as described above was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells thus cultured and proliferated were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure alcohol dehydrogenase activity by the following method. Crude enzyme solution, 50 mM Tris-HCl (pH 8.0), 0.2 mM NADH, and 100 mM isobutyraldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of isobutanol per minute was defined as 1 U (Unit).

As a result, activity was observed in all transformants into which any of *Klebsiella pneumoniae* adhP gene, *Geobacillus thermocatenulatus* adhP gene, *Geobacillus thermoglucosidasius* adhP gene, or *Geobacillus thermoglucosidasius* adhA gene was introduced, as shown in Table 2. On the other hand, no alcohol dehydrogenase activity was observed as a result of conducting the same experiment with regard to *Hydrogenophilus thermoluteolus* strain TH-1 into which an empty vector (pCYK21) was introduced.

TABLE 2

Activities of alcohol dehydrogenases that use isobutyraldehyde as a substrate, in adhP or adhA transgenic strains of Hydrogenophilus thermoluteolus

| Strain | Plasmid | Transgene | Alcohol dehydrogenase activity (U/mg-protein) |
|---|---|---|---|
| ADH01 | pC-Kpn-adhP | adhP (Klebsiella pneumoniae) | 5.2 |
| ADH02 | pC-Gtc-adhP | adhP (Geobacillus thermocatenulatus) | 4.3 |
| ADH03 | pC-Gtg-adhP | adhP (Geobacillus thermoglucosidasius) | 4.5 |
| ADH04 | pC-Gtg-adhA | adhA (Geobacillus thermoglucosidasius) | 3.1 |
| pCYK21/TH-1 | pCYK21 | None | ND (Undetectable) |

(3-5) Production of Isobutanol Producing Strain

A DNA fragment which contains adhP gene encoding the alcohol dehydrogenase of *Klebsiella pneumoniae* was amplified according to a conventional method using PCR, in which "DNA thermal cycler" manufactured by Life Technologies Inc. was used and KOD FX Neo (manufactured by Toyobo Co., Ltd.) was used as a reaction reagent. Plasmid pC-Kpn-adhP was used as a template DNA, and the following primer pair was used.

Primers for the Amplification of *Klebsiella pneumoniae* adhP Gene

```
(a-15)
                                    (SEQ ID NO: 70)
5'-CGCGGTACCGGATCTGGAGGAGAAACGCATATGAA-3'

(b-15)
                                    (SEQ ID NO: 71)
5'-CGCGGTACCTTAACGGTTGACACCGATGGTTAAAA-3'
```

A KpnI restriction site has been added to primers (a-15) and (b-15).

The produced reaction solution was subjected to electrophoresis using a 1% agarose gel, and as a result, a DNA fragment of approximately 1.0-kb of *Klebsiella pneumoniae* adhP gene was detected.

The DNA fragment containing adhP gene encoding the alcohol dehydrogenase of *Klebsiella pneumoniae* that was obtained as described above, and the above-mentioned approximately 12.3-kb DNA fragment of plasmid pC-opt-kivD which contains the codon-optimized *Lactococcus lactis* kivD gene, were each cleaved using restriction enzyme KpnI. The cleaved DNA fragments were linked to each other using a T4 DNA Ligase (manufactured by Takara Bio Inc.).

The obtained ligation solution was used to transform *Hydrogenophilus thermoluteolus* strain TH-1 (NBRC 14978) by electric pulse method, and the obtained transformants were applied onto A-solid medium containing kanamycin at 50 μg/ml, and incubated at 50° C. for 60 hours in a chamber that was filled with a mixed gas of $H_2:O_2:CO_2=7 \ 0.5:1:1.5$.

Viable strains on the A-solid medium were inoculated using a platinum loop into a test tube containing 5 ml of A-liquid medium containing kanamycin at 50 μg/ml. The test tube was filled with a mixed gas of $H_2:O_2:CO_2=7.5:1:1.5$, and subjected to shaking culture at 50° C. Plasmid DNA was extracted from the culture medium, the plasmid was cleaved using restriction enzyme KpnI, and the inserted fragment was confirmed. As a result, an approximately 1.0-kb inserted fragment of *Klebsiella pneumoniae* adhP gene was observed in addition to an approximately 12.3-kb DNA fragment of plasmid pC-opt-kivD.

The plasmid containing *Klebsiella pneumoniae* adhP gene downstream of the codon-optimized *Lactococcus lactis* kivD gene was named pC-opt-kivD&Kpn-adhP.

In addition, this strain of *Hydrogenophilus thermoluteolus* was named strain IBU-1.

(3-6) Production of Isobutanol

*Hydrogenophilus thermoluteolus* strain (IBU-1) obtained in the above item (3-5) into which an isobutanol producing gene was introduced, was inoculated using a platinum loop into A-liquid medium containing kanamycin at 50 μg/ml, and subjected to shaking culture at 50° C. for 30 hours while supplying a mixed gas of $H_2:O_2:CO_2=7.5:1:1.5$ during incubation.

Following incubation, a culture supernatant was obtained by centrifugation (4° C., 15,000 rpm, 1 minute), and isobutanol in the culture supernatant was quantified. As a result, production of 4 mM of isobutanol was confirmed in the culture supernatant.

(4) Transformant Having Ethanol Producing Ability (4-1) Cloning of Pyruvate Decarboxylase Gene Genomic DNAs were extracted from *Gluconobacter oxydans* NBRC 3292, *Zymomonas mobilis* NBRC 13756, *Zymobacter palmae* NBRC 102412, and *Acetobacter pasteurianus* NBRC 105184, respectively, according to a conventional method.

Using each of the above-described 4-kind genomic DNAs as a template, DNA fragments containing pyruvate decarboxylase pdc genes of *Gluconobacter oxydans*, *Zymomonas mobilis*, *Zymobacter palmae*, and *Acetobacter* pasteurianus were amplified, respectively, by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of *Gluconobacter oxydans* pdc Gene

```
(a-16)
                                    (SEQ ID NO: 72)
5'-GCACATATGACTTATACTGTCGGACATTATCTTGC-3'

(b-16)
                                    (SEQ ID NO: 73)
5'-GCAGGATCCTTAGACGCTCTGGGGCTTGCGGGAGT-3'
```

An NdeI restriction site has been added to primer (a-16), and a BamHI restriction site has been added to primer (b-16).

Primers for the Amplification of *Zymomonas mobilis* pdc Gene

```
(a-17)
                                    (SEQ ID NO: 74)
5'-CGAGTCCATATGAAGGCAGCTGTTGTTACCCACGA-3'

(b-17)
                                    (SEQ ID NO: 75)
5'-CGCGTCGACTTAGCTACGCAGATCGATAACCATAC-3'
```

An NdeI restriction site has been added to primer (a-17), and a SalI restriction site has been added to primer (b-17).

Primers for the Amplification of *Zymobacter palmae* pdc Gene

```
(a-18)
                                  (SEQ ID NO: 76)
5'-GCACATATGTATACCGTTGGTATGTACTTGGCAGA-3'

(b-18)
                                  (SEQ ID NO: 77)
5'-GCAGTCGACTTACGCTTGTGGTTTGCGAGAGTTGG-3'
```

An NdeI restriction site has been added to primer (a-18), and a SalI restriction site has been added to primer (b-18). Primers for the Amplification of *Acetobacter pasteurianus* pdc Gene

```
(a-19)
                                  (SEQ ID NO: 78)
5'-GCACATATGACATATACAGTCGGCATGTATCTTGC-3'

(b-19)
                                  (SEQ ID NO: 79)
5'-GCAGTCGACTCAGGATACCTGCGGTTTTCTGGAAT-3'
```

An NdeI restriction site has been added to primer (a-19), and a SalI restriction site has been added to primer (b-19).

The produced reaction solutions were subjected to electrophoresis using a 1% agarose gel, and DNA fragments of approximately 1.7-kb were detected for each of pdc genes of *Gluconobacter oxydans*, *Zymomonas mobilis*, *Zymobacter palmae*, and *Acetobacter pasteurianus*.

The approximately 1.7-kb DNA fragment of *Gluconobacter oxydans*-derived pdc gene that was amplified by the above-described PCR, and the above-mentioned approximately 10.6-kb DNA fragment of cloning vector pCYK21, were each cleaved by using restriction enzymes NdeI and BamHI. The cleaved DNA fragments were linked to each other using a T4 DNA Ligase (manufactured by Takara Bio Inc.).

The approximately 1.7-kb DNA fragments containing each of *Zymomonas mobilis*, *Zymobacter palmae*, and *Acetobacter pasteurianus* pdc genes, that were amplified by the above-described PCR were each cleaved by using restriction enzymes NdeI and SalI. The above-mentioned approximately 10.6-kb DNA fragment of cloning vector pCYK21 was also cleaved by using restriction enzymes NdeI and SalI. Each of the cleaved 1.7-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* strain TH-1 (NBRC 14978) by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture medium.

The plasmid containing *Gluconobacter oxydans*-derived pdc gene was cleaved using restriction enzymes NdeI and BamHI, and the inserted fragment was confirmed. As a result, an inserted fragment of *Gluconobacter oxydans*-derived pdc gene that was approximately 1.7-kb in length was observed in addition to an approximately 10.6-kb DNA fragment of plasmid pCYK21.

The plasmids containing each of *Zymomonas mobilis*, *Zymobacter palmae*, and *Acetobacter pasteurianus* pdc genes, were cleaved using restriction enzymes NdeI and SalI, and the inserted fragments were confirmed. As a result, inserted fragments of each of *Zymomonas mobilis*, *Zymobacter palmae*, and *Acetobacter pasteurianus* pdc genes, that were approximately 1.7-kb in length, were observed in addition to an approximately 10.6-kb DNA fragment of plasmid pCYK21.

The plasmid containing *Gluconobacter oxydans*-derived pdc gene was named pC-Gox-pdc, the plasmid containing *Zymomonas mobilis* pdc gene was named pC-Zmo-pdc, the plasmid containing *Zymobacter palmae* pdc gene was named pC-Zpa-pdc, and the plasmid containing *Acetobacter pasteurianus* pdc gene was named pC-Apa-pdc.

(4-2) Cloning of Alcohol Dehydrogenase Gene

The specifics are as described in item (3-3) of "(3) Transformant having isobutanol producing ability".

(4-3) Cloning of Aldehyde-Alcohol Dehydrogenase Gene

Genomic DNA was extracted from *Escherichia coli* K12 MG1655 according to a conventional method. In addition, genomic DNA of *Clostridium thermocellum* ATCC 27405 was obtained from National Institute of Technology and Evaluation (NBRC).

These genomic DNAs were each used as templates and DNA fragments containing aldehyde-alcohol dehydrogenase gene adhE were amplified by PCR method. The following primers were used for PCR. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of *Escherichia coli* adhE Gene

```
(a-20)
                                  (SEQ ID NO: 80)
5'-GCACATATGGCTGTTACTAATGTCGCTGAACTTAA-3'

(b-20)
                                  (SEQ ID NO: 81)
5'-GCAGGATCCTTAAGCGGATTTTTTCGCTTTTTTCT-3'
```

An NdeI restriction site has been added to primer (a-20), and a BamHI restriction site has been added to primer (b-20). Primers for the Amplification of *Clostridium thermocellum* adhE Gene

```
(a-21)
                                  (SEQ ID NO: 82)
5'-GCACATATGACGAAAATAGCGAATAAATACGAAGT-3'

(b-21)
                                  (SEQ ID NO: 83)
5'-GCACTGCAGTTATTTCTTCGCACCTCCGTAATAAG-3'
```

An NdeI restriction site has been added to primer (a-21), and a PstI restriction site has been added to primer (b-21).

Two μl of the produced reaction solutions were subjected to electrophoresis using a 1% agarose gel, and DNA fragments of approximately 2.7-kb were detected for each of adhE gene derived from *Escherichia coli* and adhE gene derived from *Clostridium thermocellum*.

The approximately 2.7-kb DNA fragment of *Escherichia coli*-derived adhE gene, that was amplified by the above-described PCR, and the above-mentioned approximately 10.6-kb DNA fragment of cloning vector pCYK21, were each cleaved by using restriction enzymes NdeI and BamHI.

The cleaved DNA fragments were linked to each other using a T4 DNA Ligase (manufactured by Takara Bio Inc.).

The approximately 2.7-kb DNA fragment of *Clostridium thermocellum*-derived adhE gene, that was amplified by the above-described PCR, and the above-mentioned approximately 10.6-kb DNA fragment of cloning vector pCYK21, were each cleaved by using restriction enzymes NdeI and PstI. The cleaved DNA fragments were linked to each other using a T4 DNA Ligase (manufactured by Takara Bio Inc.).

The obtained ligation solutions were used to transform *Hydrogenophilus thermoluteolus* TH-1 (NBRC 14978) by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture solution. Each of the plasmids was cleaved using restriction enzymes NdeI and BamHI, or NdeI and PstI, and the inserted fragments were confirmed. As a result, inserted fragment of approximately 2.7-kb in length of *Escherichia coli*-derived adhE gene or *Clostridium thermocellum*-derived adhE gene was observed in addition to an approximately 10.6-kb DNA fragment of plasmid pCYK21.

The plasmid containing *Escherichia coli*-derived adhE gene was named pC-Eco-adhE, and the plasmid containing *Clostridium thermocellum*-derived adhE gene was named pC-Cth-adhE.

The plasmids that were introduced into each transformant are shown in Table 3.

TABLE 3

Plasmids possessed by each *Hydrogenophilus thermoluteolus* recombinant strain

| Strain | Plasmid | Transgene |
|---|---|---|
| PDC01 | pC-Gox-pdc | pdc (*Gluconobacter oxydans*) |
| PDC02 | pC-Zmo-pdc | pdc (*Zymomonas mobilis*) |
| PDC03 | pC-Zpa-pdc | pdc (*Zymobacter palmae*) |
| PDC04 | pC-Apa-pdc | pdc (*Acetobacter pasteurianus*) |
| ADH01 | pC-Kpn-adhP | adhP (*Klebsiella pneumoniae*) |
| ADH02 | pC-Gtc-adhP | adhP (*Geobacillus thermocatenulatus*) |
| ADH03 | pC-Gtg-adhP | adhP (*Geobacillus thermoglucosidasius*) |
| ADH04 | pC-Gtg-adhA | adhA (*Geobacillus thermoglucosidasius*) |
| ADH05 | pC-Eco-adhE | adhE (*Escherichia coli*) |
| ADH06 | pC-Cth-adhE | adhE (*Clostridium thermocellum*) |

(4-4) Confirmation of Transgene Expression in *Hydrogenophilus Thermoluteolus* Strains into which Ethanol Producing Gene has been Introduced
Measurement of Pyruvate Decarboxylase Activity Strains PDC01, PDC02, PDC03, and PDC04 into which pyruvate decarboxylase genes (pdc genes) were introduced were inoculated using a platinum loop into test tubes containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure pyruvate decarboxylase activity by the following method. Crude enzyme solution, 250 mM sodium phosphate (pH 6.2), 1 mM $MgCl_2$, 1 mM thiamine pyrophosphate (TPP), 0.4 mM NADH, 100 mM pyruvic acid, and 0.02 mg/ml yeast alcohol dehydrogenase (Sigma-Aldrich Japan G.K.) were mixed, reacted at 50° C., and the decrease in absorbance at 340 nm coming from NADH was traced, and the initial rate of reaction was analyzed. Specific activity was calculated from the initial rate of reaction and protein concentration. The enzyme level for producing 1 μmol of acetaldehyde per minute was defined as 1 U (Unit).

As a result, 3.0 U/mg of intended pyruvate decarboxylase activity was detected in strain PDC01 into which *Gluconobacter oxydans* pdc gene was introduced.

On the other hand, no pyruvate decarboxylase activity was detected in strain PDC02 into which *Zymomonas mobilis* pdc gene was introduced, strain PDC03 into which *Zymobacter palmae* pdc gene was introduced, and strain PDC04 into which *Acetobacter pasteurianus* pdc gene was introduced.

In addition, no pyruvate decarboxylase activity was observed as a result of conducting the same experiment with regard to a wild-type strain of *Hydrogenophilus thermoluteolus* (strain TH-1 possessing only an empty vector (pCYK21)).

Measurement of Activity of Alcohol Dehydrogenase that Uses Acetaldehyde as a Substrate Each of *Hydrogenophilus thermoluteolus* strains ADH01, ADH02, ADH03, and ADH04, into which an alcohol dehydrogenase gene was introduced, was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the activity of alcohol dehydrogenase that uses acetaldehyde as a substrate by the following method. Crude enzyme solution, 50 mM Tris-HCl (pH 8.0), 0.2 mM NADH, and 90 mM acetaldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of ethanol per minute was defined as 1 U (Unit).

As a result, intended alcohol dehydrogenase activity was detected in strains ADH01 to ADH04 as shown in Table 4. *Klebsiella pneumoniae*-derived adhP gene and *Geobacillus thermoglucosidasius*-derived adhP gene showed a particularly high activity. Alcohol dehydrogenase activity was also detected with regard to *Geobacillus thermocatenulatus*-derived adhP gene and *Geobacillus thermoglucosidasius*-derived adhA gene. No alcohol dehydrogenase activity was observed as a result of conducting the same experiment with regard to *Hydrogenophilus thermoluteolus* strain TH-1 into which an empty vector (pCYK21) was introduced.

The values of the activity of alcohol dehydrogenases that use acetaldehyde as a substrate, in *Hydrogenophilus thermoluteolus* strains into which adhP gene or adhA gene has been introduced are shown in Table 4.

TABLE 4

| Strain | Plasmid | Transgene | Alcohol dehydrogenase activity (U/mg-protein) |
|---|---|---|---|
| ADH01 | pC-Kpn-adhP | adhP (*Klebsiella pneumoniae*) | 8.3 |
| ADH02 | pC-Gtc-adhP | adhP (*Geobacillus thermocatenulatus*) | 6.5 |
| ADH03 | pC-Gtg-adhP | adhP (*Geobacillus thermoglucosidasius*) | 7.8 |
| ADH04 | pC-Gtg-adhA | adhA (*Geobacillus thermoglucosidasius*) | 4.3 |
| pCYK21/TH-1 | pCYK21 | none | ND (undetectable) |

(4-5) Site-Directed Mutagenesis into adhE Gene
Construction of Plasmid for Site-Directed Mutagenesis The activity of the aldehyde-alcohol dehydrogenase encoded by adhE is inhibited under aerobic conditions. The above-described plasmid pC-Eco-adhE was used to prepare, by inverse PCR, a mutant of *Escherichia coli*-derived adhE (adhE(E568K)) in which the glutamic acid portion at position 568 (E568) was substituted by lysine (K), so that a high aldehyde-alcohol dehydrogenase activity would be shown even under aerobic conditions. The plasmid thus obtained by site-directed mutagenesis was named pC-Eco-E568K.

With regard to *Clostridium thermocellum*-derived adhE, the above-described plasmid pC-Cth-adhE was used to prepare, by inverse PCR, a mutant of *Clostridium thermocellum*-derived adhE (adhE(D575N)) in which the aspartic acid portion at position 575 (D575) was substituted by asparagine (N). The plasmid thus obtained by site-directed mutagenesis was named pC-Cth-D575N.

Inverse PCR was performed according to a conventional method using the primers described below and pC-Eco-adhE and pC-Cth-adhE as respective templates, using "DNA thermal cycler" manufactured by Life Technologies Inc., and using KOD FX Neo (manufactured by Toyobo Co., Ltd.) as a reaction reagent.
Primers for Introducing E568K Mutation of *Escherichia coli* adhE Gene (a-22)
(SEQ ID NO: 84)
5'-GAAGCTGGCGCTGCGCTTTATGGATATCCGTAAAC-3'

(b-22)
(SEQ ID NO: 85)
5'-TCGAAGTGAGTTTCCGGATGTTCGTACATAACCCA-3'

Primers for Introducing D575N Mutation of *Clostridium thermocellum* adhE ene (a-23)
(SEQ ID NO: 86)
5'-ATGGCAATGAGATTTATGGATATAAGAAAGAGAGT-3'

(b-23)
(SEQ ID NO: 87)
5'-GTTCATAAAGTCAACTTCCGGATGTTCATACATCA-3'

The produced reaction solutions were subjected to electrophoresis using a 1% agarose gel, and DNA fragments of approximately 13-kb were detected for each of E568K mutant of *Escherichia coli*-derived adhE, and D575N mutant of *Clostridium thermocellum*-derived adhE.

Each of the amplified DNA fragments was phosphorylated using a T4 Polynucleotide Kinase (manufactured by Takara Bio Inc.) and then linked (by self-ligation) using a T4 DNA Ligase (manufactured by Takara Bio Inc.).

The obtained ligation solutions were used to transform *Hydrogenophilus thermoluteolus* NBRC 14978 by electric pulse method, and the obtained transformants were applied onto A-solid medium containing kanamycin at 50 µg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C., and plasmid DNAs were extracted from the culture medium. These plasmids were cleaved by restriction enzymes NdeI and BamHI in the case of E568K mutant gene of *Escherichia coli*-derived adhE, and cleaved by restriction enzymes NdeI and PstI in the case of D575N mutant gene of *Clostridium thermocellum*-derived adhE, respectively, and the inserted fragments were confirmed. As a result, inserted fragments of approximately 2.7-kb in length were observed for each mutant in addition to approximately 10.6-kb DNA fragments of plasmid pCYK21.

The plasmids possessed by *Hydrogenophilus thermoluteolus* recombinant strains into which mutant adhE gene was introduced are shown in Table 5.

TABLE 5

| Strain | Plasmid | Transgene |
|---|---|---|
| ADH07 | pC-Eco-E568K | adhE (E568K mutation) (*Escherichia coli*) |
| ADH08 | pC-Cth-D575N | adhE (D575N mutation) (*Clostridium thermocellum*) |

(4-6) Measurement of Activity of Aldehyde-Alcohol Dehydrogenase that Uses Acetaldehyde as a Substrate Transgenic strains of *Hydrogenophilus thermoluteolus* into which aldehyde-alcohol dehydrogenase genes were introduced (ADH05, ADH06) that were produced in item (4-3), and transgenic strains of *Hydrogenophilus thermoluteolus* into which mutant aldehyde-alcohol dehydrogenase genes were introduced (ADH07, ADH08) that were produced in item (4-5), were inoculated using a platinum loop into test tubes containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells that were proliferated by culturing were collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the activity of alcohol dehydrogenase that uses acetaldehyde as a substrate, by the following method. Crude enzyme solution, 50 mM Tris-HCl (pH 8.0), 0.2 mM NADH, and 90 mM acetaldehyde were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of ethanol per minute was defined as 1 U (Unit).

As mentioned above, aldehyde-alcohol dehydrogenase encoded by adhE gene is a bifunctional enzyme that has both an aldehyde dehydrogenase activity which catalyzes the reaction of converting acetyl-CoA into acetaldehyde, and an alcohol dehydrogenase activity which catalyzes the reaction of converting acetaldehyde into ethanol. Here, the expression of adhE gene was evaluated using as an index, the reaction of producing ethanol in which acetaldehyde is used as a substrate. However, each of the above-described strains also had an aldehyde dehydrogenase activity which catalyzes the reaction of converting acetyl-CoA into acetaldehyde.

As a result, strains ADH07 and ADH08 into which mutated genes were introduced had 1.5-fold and 3.4-fold improved activity as compared to those of strains ADH05 and ADH06 into which wild-type genes were introduced, respectively, as shown in Table 6.

TABLE 6

| Strain | Plasmid | Transgene | Alcohol dehydrogenase activity (U/mg-protein) |
|---|---|---|---|
| ADH05 | pC-Eco-adhE | adhE (*Escherichia coli*) | 0.34 |
| ADH06 | pC-Cth-adhE | adhE (*Clostridium thermocellum*) | 0.26 |
| ADH07 | pC-Eco-E568K | adhE (E568K mutation) (*Escherichia coli*) | 0.52 |
| ADH08 | pC-Cth-D575N | adhE (D575N mutation) (*Clostridium thermocellum*) | 0.89 |
| pCYK21/ TH-1 | pCYK21 | None | ND (undetectable) |

(4-7) Production of Ethanol Producing Strain

The DNA fragment which contains adhP gene encoding the alcohol dehydrogenase of *Klebsiella pneumoniae* was amplified according to a conventional method using PCR, in which "DNA thermal cycler" manufactured by Life Technologies Inc. was used and KOD FX Neo (manufactured by Toyobo Co., Ltd.) was used as a reaction reagent. Plasmid pC-Kpn-adhP was used as a template DNA, and the following primer pair was used.

Primers for the Amplification of *Geobacillus thermoglucosidasius* adhP Gene (a-24)
(SEQ ID NO: 88)
5'-CGCGGTACCGGATCTGGAGGAGAAACGCATATGAA-3'

(b-24)
(SEQ ID NO: 89)
5'-CGCGGTACCTTAACGGTTGACACCGATGGTTAAAA-3'

A KpnI restriction site has been added to primers (a-24) and (b-24).

The produced reaction solution was subjected to electrophoresis using a 1% agarose gel, and as a result, a DNA fragment of approximately 1.0-kb was detected which corresponds to *Geobacillus thermoglucosidasius*-derived adhP gene.

The approximately 1.0-kb DNA fragment of *Klebsiella pneumoniae* adhP gene that was amplified by the above-mentioned PCR, and the approximately 12.3-kb DNA fragment of plasmid pC-Gox-pdc that contains *Gluconobacter oxydans* pdc gene, were each cleaved by restriction enzyme KpnI. The cleaved DNA fragments were linked to each other using a T4 DNA Ligase (manufactured by Takara Bio Inc.).

The obtained ligation solution was used to transform *Hydrogenophilus thermoluteolus* NBRC 14978 by electric pulse method, and the obtained transformant was applied onto A-solid medium containing kanamycin at 50 μg/ml, and incubated at 50° C. for 60 hours in a chamber that was filled with a mixed gas of $H_2:O_2:CO_2=7.5:1:1.5$.

Viable strains on the A-solid medium were inoculated using a platinum loop into a test tube containing 5 ml of A-liquid medium containing kanamycin at 50 μg/ml. The test tube was filled with a mixed gas of $H_2:O_2:CO_2=7.5:1:1.5$, and subjected to shaking culture at 50° C., and plasmid DNA was extracted from the culture medium. The plasmid was cleaved by restriction enzyme KpnI, and the inserted fragment was confirmed. As a result, an approximately 1.0-kb inserted fragment of *Klebsiella pneumoniae* adhP gene was observed in addition to an approximately 12.3-kb DNA fragment of plasmid pC-Gox-pdc.

The plasmid containing *Geobacillus thermoglucosidasius* adhP gene downstream of *Gluconobacter oxydans* pdc gene, was named pC-Gox-pdc&Kpn-adhP.

The strain possessing this plasmid was named *Hydrogenophilus thermoluteolus* strain ETH-1.

(4-8) Production of Ethanol

*Hydrogenophilus thermoluteolus* strain (strain ETH-1) into which an ethanol producing gene was introduced, which was obtained in the above item (4-7), was inoculated using a platinum loop into A-liquid medium containing kanamycin at 50 μg/ml, and subjected to shaking culture at 50° C. for 30 hours while supplying a mixed gas of $H_2:O_2:CO_2=7.5:1:1.5$ accompanying incubation.

Following incubation, the culture supernatant was obtained by centrifugation (4° C., 15,000 rpm, 1 minute), and as a result of quantification of the ethanol therein, production of 10 mM of ethanol was confirmed in the culture supernatant.

(5) Production of Transformant Having Alanine Producing Ability (5-1) Preparation of Genomic DNA Genomic DNA was extracted from *Geobacillus stearothermophilus* ATCC 12980 according to a conventional method. In addition, genomic DNA of *Thermus thermophilus* strain HB8 (ATCC 27634) was purchased from Takara Bio Inc.

(5-2) Cloning of DNA Fragment Containing alaD Gene

DNA fragments containing alanine dehydrogenase genes were amplified by PCR using each of the genomic DNA of *Geobacillus stearothermophilus* ATCC 12980 and the genomic DNA of *Thermus thermophilus* strain HB8 (ATCC 27634) as templates, and using the following primer pairs. PCR was performed according to a conventional method using "DNA thermal cycler" manufactured by Life Technologies Inc., and using KOD FX Neo (manufactured by Toyobo Co., Ltd.) as a reaction reagent.

Primers for the Amplification of *Geobacillus stearothermophilus* alaD1 Gene (a-25)
(SEQ ID NO: 90)
5'-TCCGGCGGGCATATGAAGATCGGCATTCCAAAAGA-3'

(b-25)
SEQ ID NO: 91)
5'-AAGAATTCCAGCGGCTCATATACGATACCGTTCGG-3'

An NdeI restriction site has been added to primer (a-25), and an EcoRI restriction site has been added to primer (b-25).

Primers for the Amplification of *Geobacillus stearothermophilus* alaD2 Gene

```
(a-26)
                                       (SEQ ID NO: 92)
5'-TCCGGCGGGCATATGATTATTGGAGTGCCAAAGGA-3'

(b-26)
                                       (SEQ ID NO: 93)
5'-AAGAATTCTTAGTTGGCAGCCAACGTTTTCCCGAG-3'
```

An NdeI restriction site has been added to primer (a-26), and an EcoRI restriction site has been added to primer (b-26).

Primers for the Amplification of *Thermus thermophilus* alaD1 Gene

```
(a-27)
                                       (SEQ ID NO: 94)
5'-CCGGCGGGCATATGGTGATCGGCGTGCCGAAGGAG-3'

(b-27)
                                       (SEQ ID NO: 95)
5'-AAGAATTCTCACCCCCTCAAGGCCTCCTCGGGAGG-3'
```

An NdeI restriction site has been added to primer (a-27), and an EcoRI restriction site has been added to primer (b-27).

Primers for the Amplification of *Thermus thermophilus* alaD2 Gene

```
(a-28)
                                       (SEQ ID NO: 96)
5'-CGGCGGGCATATGgagttcggcgtgcccagagaac-3'

(b-28)
                                       (SEQ ID NO: 97)
5'-AAGAATTCtcattctaggtggcctcctttctcgcc-3'
```

An NdeI restriction site has been added to primer (a-28), and an EcoRI restriction site has been added to primer (b-28).

The produced reaction solutions were subjected to electrophoresis using a 1% agarose gel, and a DNA fragment of approximately 1.6-kb was detected in the case of *Geobacillus stearothermophilus* alaD1 gene, and DNA fragments of approximately 1.1-kb were detected in each of the cases of *Geobacillus stearothermophilus* alaD2 gene, *Thermus thermophilus* alaD1 gene, and *Thermus thermophilus* alaD2 gene.

Each of the approximately 1.6-kb DNA fragment of *Geobacillus stearothermophilus* alaD1 gene, the approximately 1.1-kb DNA fragment of *Geobacillus stearothermophilus* alaD2 gene, the approximately 1.1-kb DNA fragment of *Thermus thermophilus* alaD1 gene, and the approximately 1.1-kb DNA fragment of *Thermus thermophilus* alaD2 gene, which was amplified by the above-described PCR, were cleaved by restriction enzymes NdeI and EcoRI. The approximately 10.6-kb DNA fragment of the above-described cloning vector pCYK21 was also cleaved by restriction enzymes NdeI and EcoRI. Each of the cleaved 1.6-kb or 1.1-kb DNA fragments and the 10.6-kb DNA fragment were linked to each other using a T4 DNA Ligase (manufactured by Takara Bio Inc.).

The obtained ligation solutions were used to transform *Hydrogenophilus thermoluteolus* NBRC 14978 by electric pulse method, and the obtained transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C., and plasmid DNAs were extracted from the culture solutions. These plasmids were each cleaved by restriction enzymes NdeI and EcoRI, and the inserted fragments were confirmed. As a result, an inserted fragment of approximately 1.6-kb in length in the case of *Geobacillus stearothermophilus* alaD1 gene, and inserted fragments of approximately 1.1-kb in length in each of the cases of *Geobacillus stearothermophilus* alaD2 gene, *Thermus thermophilus* alaD1 gene, and *Thermus thermophilus* alaD2 gene, were observed in addition to an approximately 10.6-kb DNA fragment of plasmid pCYK21.

The plasmid containing *Geobacillus stearothermophilus* alaD1 gene was named pC-Gst-alaD1, the plasmid containing *Geobacillus stearothermophilus* alaD2 gene was named pC-Gst-alaD2, the plasmid containing *Thermus thermophilus* alaD1 gene was named pC-Tth-alaD1, and the plasmid containing *Thermus thermophilus* alaD2 gene was named pC-Tth-alaD2. The plasmids that are possessed by these recombinant strains of *Hydrogenophilus thermoluteolus* are shown in Table 7.

TABLE 7

| Strain | Plasmid | Transgene |
|---|---|---|
| ALA01 | pC-Gst-alaD1 | alaD1 (*Geobacillus stearothermophilus*) |
| ALA02 | pC-Gst-alaD2 | alaD2 (*Geobacillus stearothermophilus*) |
| ALA03 | pC-Tth-alaD1 | alaD1 (*Thermus thermophilus*) |
| ALA04 | pC-Tth-alaD2 | alaD2 (*Thermus thermophilus*) |

(5-3) Measurement of Alanine Dehydrogenase Activity

Each of strains ALA01, ALA02, ALA03, and ALA04, which are *Hydrogenophilus thermoluteolus* strains into which alanine dehydrogenase gene has been introduced, was inoculated using a platinum loop into a test tube containing 5 ml of A-liquid medium containing kanamycin at 50 μg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure alanine dehydrogenase activity by the following method. Crude enzyme solution, 100 mM Tris-HCl (pH 8.5), 100 mM $NH_4Cl$, 0.1 mM NADH, and 60 mM pyruvic acid were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 μmol of alanine per minute was defined as 1 U (Unit).

The values of the activity of alanine dehydrogenases that were produced by the alaD gene-introduced strains of *Hydrogenophilus thermoluteolus* are shown in Table 8.

TABLE 8

| Strain | Plasmid | Transgene | Alanine dehydrogenase activity (U/mg-protein) |
|---|---|---|---|
| ALA01 | pC-Gst-alaD1 | alaD1 (*Geobacillus stearothermophilus*) | 15.5 |
| ALA02 | pC-Gst-alaD2 | alaD2 (*Geobacillus stearothermophilus*) | 35.1 |
| ALA03 | pC-Tth-alaD1 | alaD1 (*Thermus thermophilus*) | 3.7 |
| ALA04 | pC-Tth-alaD2 | alaD2 (*Thermus thermophilus*) | 0.5 |
| pCYK21/TH-1 | pCYK21 | None | ND (undetectable) |

As shown in Table 8, alanine dehydrogenase activity of interest was detected in strains ALA01, ALA02, ALA03, and ALA04. *Geobacillus stearothermophilus*-derived alaD2 gene showed a particularly high activity. On the other hand, no alanine dehydrogenase activity was observed as a result of conducting the same experiment with regard to *Hydrogenophilus thermoluteolus* strain TH-1 into which an empty vector (pCYK21) was introduced.

(5-4) Addition of Polypeptide to the N Terminus for the Improvement of Gene Expression Level Preparation of DNA Fragment Encoding Polypeptide to be Added Each of the following pairs of oligonucleotides was synthesized in order to prepare DNA fragments which encode polypeptides to be added. Sequences of each of the pair of oligonucleotides are complementary with one another.

Polypeptide of Sequence MKIEEGKLVIH (SEQ ID NO: 37) (Sequence of the N Terminus of Maltose-Binding Protein)

(a-29)
(SEQ ID NO: 98)
5'-TATGAAAATCGAAGAAGGTAAACTGGTAATCCA-3'

(b-29)
(SEQ ID NO: 99)
5'-TATGGATTACCAGTTTACCTTCTTCGATTTTCA-3'

Polypeptide of Sequence MSKIKH (SEQ ID NO: 100) [Journal of Bioscience and Bioengineering, 123, 540-546 (2017)]

(a-30)
(SEQ ID NO: 101)
5'-TATGAGCAAGATCAAACA-3'

(b-30)
(SEQ ID NO: 102)
5'-TATGTTTGATCTTGCTCA-3'

Polypeptide of Sequence MDFPVAEDRRH (SEQ ID NO: 103) (Sequence of the N Terminus of Glutathione S-Transferase)

(a-31)
(SEQ ID NO: 104)
5'-TATGTCGCCGATCCTCGGCTACTGGAAAATCCA-3'

(b-31)
(SEQ ID NO: 105)
5'-TATGGATTTTCCAGTAGCCGAGGATCGGCGACA-3'

Polypeptide of Sequence MTENAEKFLWH (SEQ ID NO: 106) (Sequence of the N Terminus of β-Glucosidase)

(a-32)
(SEQ ID NO: 107)
5'-TATGACCGAGAACGCCGAAAAATTCCTTTGGCA-3'

(b-32)
(SEQ ID NO: 108)
5'-TATGCCAAAGGAATTTTTCGGCGTTCTCGGTCA-3'

Equimolar (mol) amounts of each of the oligonucleotides (a-29) and (b-29), (a-30) and (b-30), (a-31) and (b-31), (a-32) and (b-32), were mixed, and the mixed solutions were gradually cooled from 98° C. to 20° C. As a result of annealing of the oligonucleotides, double-stranded DNA fragments encoding polypeptide sequences were prepared. Both ends of these DNA fragments are equivalent to the cohesive end generated from cleavage by restriction enzyme NdeI.

In addition, in order to prepare a DNA fragment which consists of a base sequence encoding the sequence of MGKDHLIHNVHKEEHAHAHNKH (SEQ ID NO: 109) (HAT sequence), PCR was performed using a primer pair described below, using "DNA thermal cycler" manufactured by Life Technologies Inc., and using KOD FX Neo (manufactured by Toyobo Co., Ltd.) as a reaction reagent. No template DNA was included since extension was carried out using each primer as the other's template.

Primers for Preparing HAT Sequence (a-33)
(SEQ ID NO: 110)
5'-CGCATATGGGCAAGGATCATCTCATCCACAATGTCCACAAAGAGG-3'

(b-33)
(SEQ ID NO: 111)
5'-CGCATATGCTTGTTGTGGGCATGAGCGTGCTCCTCTTTGTGGACA-3'

The base sequences of the 3' end of primers (a-33) and (b-33) are complementary to each other. An NdeI restriction site has been added to primers (a-33) and (b-33).

The produced reaction solution was subjected to electrophoresis using a 1% agarose gel, and as a result, a DNA fragment of approximately 0.1-kb which corresponds to the HAT sequence was detected. The approximately 0.1-kb DNA fragment of the HAT sequence that was amplified was cleaved by restriction enzyme NdeI.

Construction of Expression Vector for Polypeptide-Fused Protein

Plasmid pC-Gst-alaD2 which contains *Geobacillus stearothermophilus* alaD2 gene was cleaved by restriction enzyme NdeI. This plasmid and each of the above-described DNA fragments which have an overhang on both ends due to cleavage by restriction enzyme NdeI (the 5-kind double-stranded DNA fragments that were prepared in item "Preparation of DNA fragment encoding polypeptide to be added") were mixed, and were linked to each other using a T4 DNA Ligase (manufactured by Takara Bio Inc.).

The obtained ligation solutions were used to transform *Hydrogenophilus thermoluteolus* NBRC 14978 by electric pulse method, and the transformants were applied onto A-solid medium containing kanamycin at 50 μg/ml, and incubated at 50° C. for 60 hours in a chamber that was filled with a mixed gas of $H_2:O_2:CO_2=7.5:1:1.5$.

Each of the viable strains on the A-solid medium was inoculated using a platinum loop into a test tube containing 5 ml of A-liquid medium containing kanamycin at 50 µg/ml. The test tubes were filled with a mixed gas of $H_2:O_2:CO_2=7.5:1:1.5$, and subjected to shaking culture at 50° C. Plasmid DNAs were extracted from the culture solutions, and each of the plasmids were cleaved using restriction enzyme NdeI, and inserted fragments were confirmed.

The plasmid for adding the N terminus sequence of maltose-binding protein to generate a fusion peptide was named pMBP-Gst-alaD2, the plasmid for adding the sequence MSKIKH to generate a fusion peptide was named pSKIK-Gst-alaD2, the plasmid for adding the N terminus sequence of glutathione S-transferase to generate a fusion peptide was named pGST-Gst-alaD2, the plasmid for adding the N terminus sequence of R-glucosidase to generate a fusion peptide was named pGlu-Gst-alaD2, and the plasmid for adding the HAT tag sequence to generate a fusion peptide was named pHAT-Gst-alaD2.

The plasmids possessed by the recombinant strains are shown in Table 9.

TABLE 9

| Strain | Plasmid | N terminus-fused peptide |
|---|---|---|
| ALA02 | pC-Gst-alaD2 | None |
| ALA05 | pMBP-Gst-alaD2 | N terminus sequence of maltose-binding protein |
| ALA06 | pSKIK-Gst-alaD2 | Sequence MSKIKH |
| ALA07 | pGST-Gst-alaD2 | N terminus sequence of glutathione S-transferase |
| ALA08 | pGlu-Gst-alaD2 | N terminus sequence of β-glucosidase |
| ALA09 | pHAT-Gst-alaD2 | HAT tag sequence |

(5-5) Effect of Polypeptide Fusion at N Terminus Side on Expression of alaD2 Gene Transgenic strains of *Hydrogenophilus thermoluteolus* into which polypeptide-fused alanine dehydrogenase genes were introduced that were produced in item (5-4), were inoculated using a platinum loop into test tubes containing 5 ml of A-liquid medium containing kanamycin at 50 µg/ml. The test tubes were filled with a mixed gas of $H_2:O_2:CO_2=7.5:1:1.5$, and subjected to shaking culture at 50° C. for 20 hours.

Bacterial cells that were proliferated by culturing were each collected by centrifugation (4° C., 15,000 rpm, 1 minute). The bacterial cells were disrupted by sonication, and subsequently centrifuged (4° C., 15,000 rpm, 5 minutes) to obtain a cell disruption supernatant. The cell disruption supernatant was used as a crude enzyme solution to measure the alanine dehydrogenase activity by the following method. Crude enzyme solution, 100 mM Tris-HCl (pH 8.5), 100 mM $NH_4Cl$, 0.1 mM NADH, and 60 mM pyruvic acid were mixed, reacted at 50° C., and decrease in absorbance at 340 nm coming from NADH was traced, and the initial rate of reaction was analyzed. Specific activity was calculated from the initial rate of reaction and protein concentration. The enzyme level for producing 1 µmol of alanine per minute was defined as 1 U (Unit).

The activities of alanine dehydrogenases that were produced by alaD transgenic strains of *Hydrogenophilus thermoluteolus* are shown in Table 10.

TABLE 10

| Strain | Plasmid | N terminus-fused peptide | Alanine dehydrogenase activity (U/mg-protein) |
|---|---|---|---|
| ALA02 | pC-Gst-alaD2 | None | 35.1 |
| ALA05 | pMBP-Gst-alaD2 | N terminus sequence of maltose-binding protein | 144.6 |
| ALA06 | pSKIK-Gst-alaD2 | Sequence MSKIKH | 11.7 |
| ALA07 | pGST-Gst-alaD2 | N terminus sequence of glutathione S-transferase | 10.9 |
| ALA08 | pGlu-Gst-alaD2 | N terminus sequence of β-glucosidase | 2.7 |
| ALA09 | pHAT-Gst-alaD2 | HAT tag sequence | 31.2 |

As shown in Table 10, only strain ALA05 showed a higher alanine dehydrogenase activity as compared to that of the strain into which *Geobacillus stearothermophilus* alaD2 gene was introduced (strain ALA02).

(5-6) Production of Alanine

Transgenic strain ALA05 of *Hydrogenophilus thermoluteolus* into which an alanine dehydrogenase gene was introduced, was inoculated using a platinum loop into A-liquid medium containing kanamycin at 50 µg/ml, and subjected to shaking culture at 50° C. for 30 hours while supplying a mixed gas of $H_2:O_2:CO_2=7.5:1:1.5$ during incubation.

Following incubation, the culture supernatant was obtained by centrifugation (4° C., 15,000 rpm, 1 minute), and as a result of quantification of the alanine therein, production of 5 mM of alanine was confirmed in the culture supernatant.

(6) Deposited Strains

Each of the strains shown in the following Table 11 was deposited to NITE Patent Microorganisms Depositary, National Institute of Technology and Evaluation (2-5-8 Kazusakamatari, Kisarazu-shi, Chiba, Japan (postal code 292-0818)). The date of acceptance and the accession numbers are shown in Table 11. Accordingly, these strains are available to the public.

TABLE 11

| Deposited strain | Date of acceptance | Accession number |
|---|---|---|
| *Hydrogenophilus thermoluteolus* IBU-1 | Apr. 18, 2018 | NITE BP-02696 |
| *Hydrogenophilus thermoluteolus* ETH-1 | Apr. 18, 2018 | NITE BP-02697 |
| *Hydrogenophilus thermoluteolus* ADH05 | Apr. 18, 2018 | NITE P-02691 |
| *Hydrogenophilus thermoluteolus* ADH07 | Apr. 18, 2018 | NITE P-02692 |
| *Hydrogenophilus thermoluteolus* ADH08 | Apr. 18, 2018 | NITE P-02693 |
| *Hydrogenophilus thermoluteolus* ALA02 | Apr. 18, 2018 | NITE P-02694 |
| *Hydrogenophilus thermoluteolus* ALA05 | Apr. 18, 2018 | NITE BP-02695 |

Furthermore, all strains (including ATCC strains and NBRC strains) that are described in the present specification are internationally deposited under the Budapest Treaty, or are possessed by organizations that furnish the strains without any terms or conditions, or are marketed, and therefore, the strains are all available to the public.

INDUSTRIAL APPLICABILITY

The transformant of the present invention effectively produces isobutanol, ethanol, or alanine using carbon dioxide as a sole carbon source, and therefore, the two problems of global warming due to carbon dioxide increase and difficulty in securing food, feed, and fuel, can both be solved.

The invention claimed is:

1. A transformant obtained by introducing an alanine dehydrogenase gene into a bacterium of genus *Hydrogenophilus*, wherein the alanine dehydrogenase gene is a DNA of (e1), (e2), (e4), (e5), (e6), (e7), (e8), (e9), (e10), or (e11) below:
   - (e1) DNA which comprises a base sequence of SEQ ID NO: 29, 30, 31, or 32;
   - (e2) DNA which comprises a base sequence having 90% or more identity with SEQ ID NO: 29, 30, the DNA encoding a polypeptide having alanine dehydrogenase activity;
   - (e4) DNA which encodes a polypeptide comprising an amino acid sequence of SEQ ID NO: 33, 34, 35, or 36;
   - (e5) DNA which encodes a polypeptide comprising an amino acid sequence having 90% or more identity with SEQ ID NO: 33, 34, the polypeptide having alanine dehydrogenase activity;
   - (e6) DNA which encodes a polypeptide comprising an amino acid sequence having a deletion, substitution, or addition of one to five of amino acids in the amino acid sequence of SEQ ID NO: 33, 34, 35, or 36, the polypeptide having alanine dehydrogenase activity;
   - (e7) DNA which encodes a polypeptide comprising an amino acid sequence in which an amino acid sequence of SEQ ID NO: 37 is added to the N terminus of the amino acid sequence of SEQ ID NO: 33, 34;
   - (e8) DNA which encodes a polypeptide comprising an amino acid sequence in which the amino acid sequence of SEQ ID NO: 37 is added to the N terminus of the amino acid sequence having 90% or more identity with SEQ ID NO: 33, 34, the polypeptide having alanine dehydrogenase activity;
   - (e9) DNA which encodes a polypeptide comprising an amino acid sequence in which the amino acid sequence of SEQ ID NO: 37 is added to an N terminus of the amino acid sequence having a deletion, substitution, or addition of one to five of amino acids in the amino acid sequence of SEQ ID NO: 33, 34, the polypeptide having alanine dehydrogenase activity;
   - (e10) DNA which comprises a base sequence in which a base sequence of SEQ ID NO: 38 is added to the 5' end of the base sequence of SEQ ID NO: 29, 30;
   - (e11) DNA which comprises a base sequence in which the base sequence of SEQ ID NO: 38 is added to the 5' end of a base sequence having 90% or more identity with SEQ ID NO: 29, 30, the 2 DNA encoding a polypeptide having alanine dehydrogenase activity.

2. A method for producing alanine comprising a step of culturing the transformant according to claim 1, while using carbon dioxide.

3. The transformant according to claim 1, wherein the bacterium of the genus *Hydrogenophilus* is *Hydrogenophilus thermoluteolus*.

4. The transformant according to claim 1, wherein the alanine dehydrogenase gene comprises a modified alanine dehydrogenase gene, in which a polynucleotide comprising a base sequence of SEQ ID NO: 38 is added to the 5' end of the alanine dehydrogenase gene.

5. The transformant according to claim 4, wherein the bacterium of the genus *Hydrogenophilus* is *Hydrogenophilus thermoluteolus*.

6. A method for producing alanine comprising a step of culturing the transformant according to claim 4, while using carbon dioxide.

7. The transformant according to claim 4, wherein the modified alanine dehydrogenase gene comprises a base sequence of SEQ ID NO: 40.

8. The transformant according to claim 7, wherein the bacterium of the genus *Hydrogenophilus* is *Hydrogenophilus thermoluteolus*.

9. A method for producing alanine comprising a step of culturing the transformant according to claim 7, while using carbon dioxide.

10. The transformant according to claim 1, wherein the alanine dehydrogenase gene comprises a base sequence of SEQ ID NO: 29, 30, 31, or 32.

11. The transformant according to claim 1, wherein the alanine dehydrogenase gene comprises a base sequence having 90% or more identity with SEQ ID NO: 29, 30.

12. The transformant according to claim 1, wherein the alanine dehydrogenase gene comprises a DNA which encodes a polypeptide comprising an amino acid sequence of SEQ ID NO: 33, 34.

13. The transformant according to claim 1, wherein the alanine dehydrogenase gene comprises a DNA which encodes a polypeptide comprising an amino acid sequence having 90% or more identity with SEQ ID NO: 33, 34.

14. The transformant according to claim 1, wherein the alanine dehydrogenase gene comprises a DNA which encodes a polypeptide comprising an amino acid sequence in which an amino acid sequence of SEQ ID NO: 37 is added to the N terminus of the amino acid sequence of SEQ ID NO: 33, 34.

15. The transformant according to claim 1, wherein the alanine dehydrogenase gene comprises a DNA which encodes a polypeptide comprising an amino acid sequence in which an amino acid sequence of SEQ ID NO: 37 is added to the N terminus of the amino acid sequence having 90% or more identity with SEQ ID NO: 33, 34.

16. The transformant according to claim 1, wherein the alanine dehydrogenase gene comprises a base sequence in which a base sequence of SEQ ID NO: 38 is added to the 5' end of the base sequence of SEQ ID NO: 29, 30.

17. The transformant according to claim 1, wherein the alanine dehydrogenase gene comprises a base sequence in which the base sequence of SEQ ID NO: 38 is added to the 5' end of a base sequence having 90% or more identity with SEQ ID NO: 29, 30.

18. A transformant obtained by introducing an alanine dehydrogenase gene into a bacterium of genus *Hydrogenophilus*, wherein the alanine dehydrogenase gene comprises (i) a base sequence having 90% or more identity with SEQ ID NO: 29, or (ii) a DNA which encodes a polypeptide comprising an amino acid sequence having 90% or more identity with SEQ ID NO: 33.

19. A transformant obtained by introducing an alanine dehydrogenase gene into a bacterium of genus *Hydrogenophilus*, wherein the alanine dehydrogenase comprises (i) a base sequence having 90% or more identity with SEQ ID NO: 30, or (ii) a DNA which encodes a polypeptide comprising an amino acid sequence having 90% or more identity with SEQ ID NO: 34.

* * * * *